(12) United States Patent
Kim

(10) Patent No.: US 11,364,237 B2
(45) Date of Patent: Jun. 21, 2022

(54) COMPOSITION FOR INHIBITING CANCER METASTASIS AND TREATING CANCER

(71) Applicant: ONCOCROSS CO., LTD., Seoul (KR)

(72) Inventor: Yi-Rang Kim, Sejong (KR)

(73) Assignee: ONCOCROSS CO., LTD., Seoul (KR)

( * ) Notice: Subject to any disclaimer, the term of this patent is extended or adjusted under 35 U.S.C. 154(b) by 43 days.

(21) Appl. No.: 16/484,305

(22) PCT Filed: Feb. 6, 2018

(86) PCT No.: PCT/KR2018/001549
§ 371 (c)(1),
(2) Date: Aug. 7, 2019

(87) PCT Pub. No.: WO2018/147612
PCT Pub. Date: Aug. 16, 2018

(65) Prior Publication Data
US 2019/0374538 A1    Dec. 12, 2019

(30) Foreign Application Priority Data

Feb. 7, 2017  (KR) .................. 10-2017-0016587
Feb. 6, 2018  (KR) .................. 10-2018-0014306

(51) Int. Cl.
| A61K 31/4965 | (2006.01) |
| A61P 35/00 | (2006.01) |
| A61K 31/085 | (2006.01) |
| A61K 31/195 | (2006.01) |
| A61K 31/4706 | (2006.01) |

(52) U.S. Cl.
CPC ........ *A61K 31/4965* (2013.01); *A61K 31/085* (2013.01); *A61K 31/195* (2013.01); *A61K 31/4706* (2013.01); *A61P 35/00* (2018.01)

(58) Field of Classification Search
CPC ............. A61K 31/047; A61K 31/085; A61K 31/4706; A61K 31/4965
See application file for complete search history.

(56) References Cited

U.S. PATENT DOCUMENTS 3,214,336 A * 10/1965 Parker .................... A61K 31/27
514/489

8,901,137 B2 * 12/2014 Aftab ...................... A61P 35/00
514/264.11
2013/0023488 A1    1/2013 Wu
2015/0361077 A1 * 12/2015 Simpson ................. A01N 43/42
514/249

FOREIGN PATENT DOCUMENTS

| CN | 105616411 A | * | 6/2016 |
| KR | 10-2014-0004771 A | | 1/2014 |
| WO | 2011-132171 A1 | | 10/2011 |

OTHER PUBLICATIONS

Spencer et al. (Proceedings of the Society for Experimental Biology and Medicine, 1972, 40, 1156-1161) (Year: 1972).*
Spencer et al. (Proceedings of the Society of Experimental Biology and Medicine vol. 140 pp. 1156-1161. Published 1972. NPL Entry 3 in IDS of Aug. 7, 2019). (Year: 1972).*
Liang et al. (Cell and Bioscience vol. 4 pp. 1-11. Published 2014). (Year: 2014).*
Jiang et al (Biomedicine and Pharmacotherapy vol. 64 pp. 609-614. Published 2010) (Year: 2010).*
Ewens etal (Anticancer Research vol. 25 p. 3905-3915. Published 2005) (Year: 2005).*
Chlorphenesin (Pubchem published Mar. 26, 2005) (Year: 2005).*
Hannelore Maes et al., "Tumor Vessel Normalization by Chloroquine Independent of Autophagy", Cancer Cell, Aug. 11, 2014, pp. 190-206, vol. 26, No. 2.
T. Giraldi et al., "Neutral Proteinase Inhibitors and Antimetastatic Effects in Mice", European Journal of Cancer, 1980, pp. 449-454, vol. 16, No. 4.
H. J. Spencer et al., "Attenuation of Certain Neoplasias by Chlorphenesin (36631)", Proceedings of the Society for Experimental Biology and Medicine, 1972, pp. 1156-1161, vol. 140, No. 4.
International Search Report of PCT/KR2018/001549 dated Jun. 25, 2018 [PCT/ISA/210].
Written Opinion of PCT/KR2018/001549 dated Jun. 25, 2018 [PCT/ISA/237].

* cited by examiner

*Primary Examiner* — Theodore R. Howell
*Assistant Examiner* — George W Kosturko
(74) *Attorney, Agent, or Firm* — Sughrue Mion, PLLC

(57) ABSTRACT

The present invention relates to an anticancer and metastasis inhibiting effect by treatment with chlorphenesin, chloroquine, and chloropyrazine alone or in combination. Chlorphenesin, chloroquine, or chloropyrazine show the effect of killing cancer cells and inhibiting proliferation, and metastasis of cancer cells and particularly, a combination thereof is identified to have synergism. Cancer can be effectively prevented or treated by administering chlorphenesin, chloroquine, and chloropyrazine alone or in combination thereof.

5 Claims, 61 Drawing Sheets

[Figure 1]
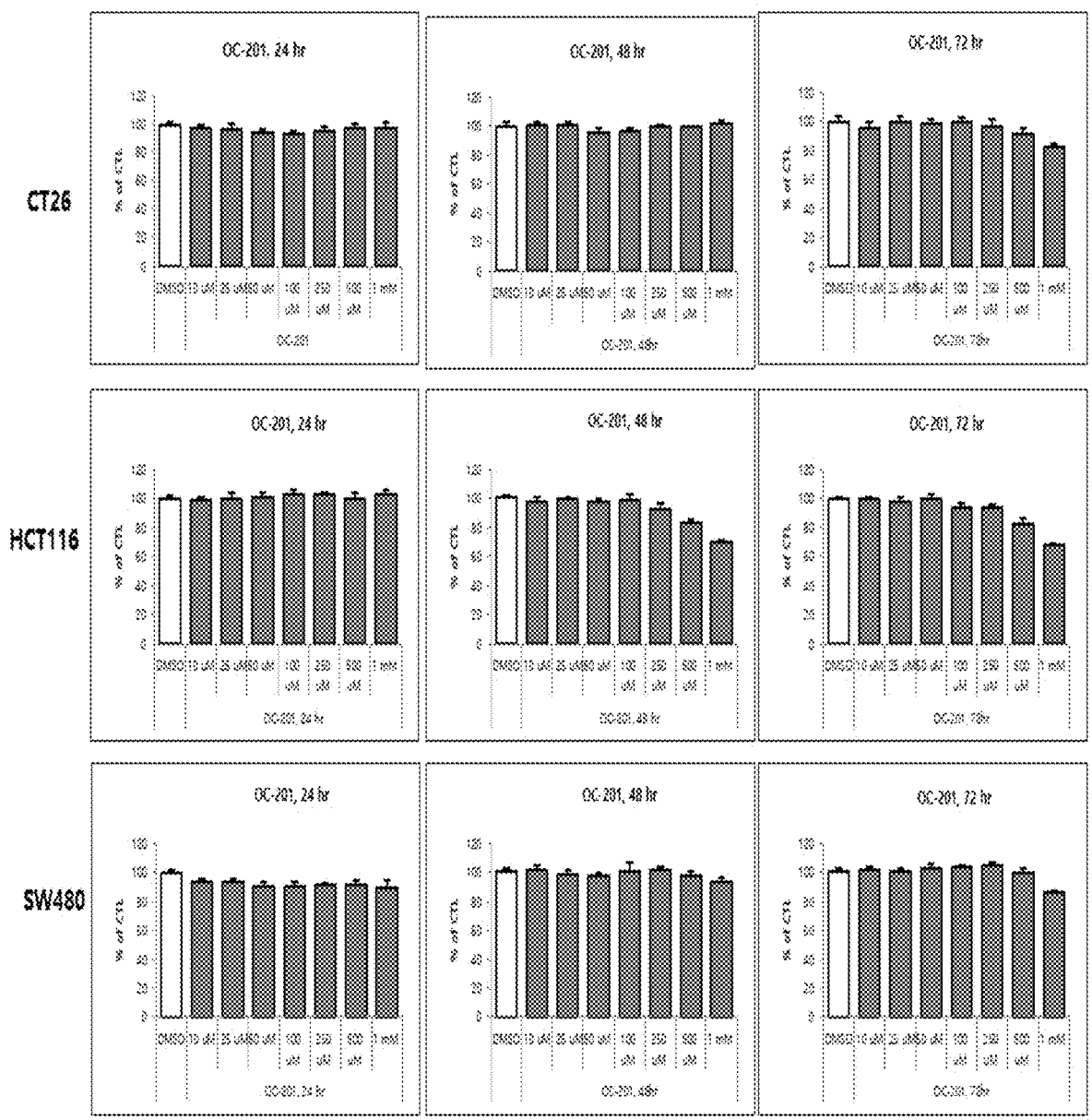

[Figure 2]
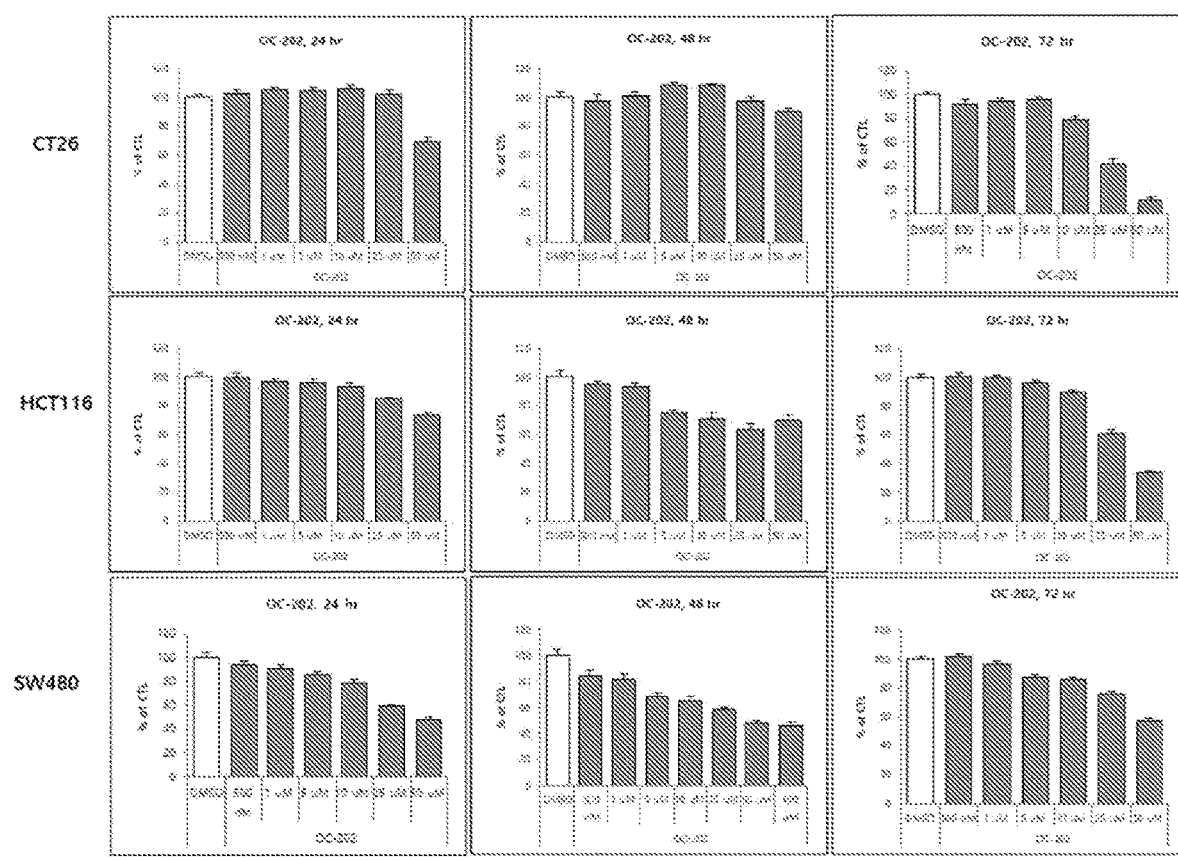

[Figure 3]
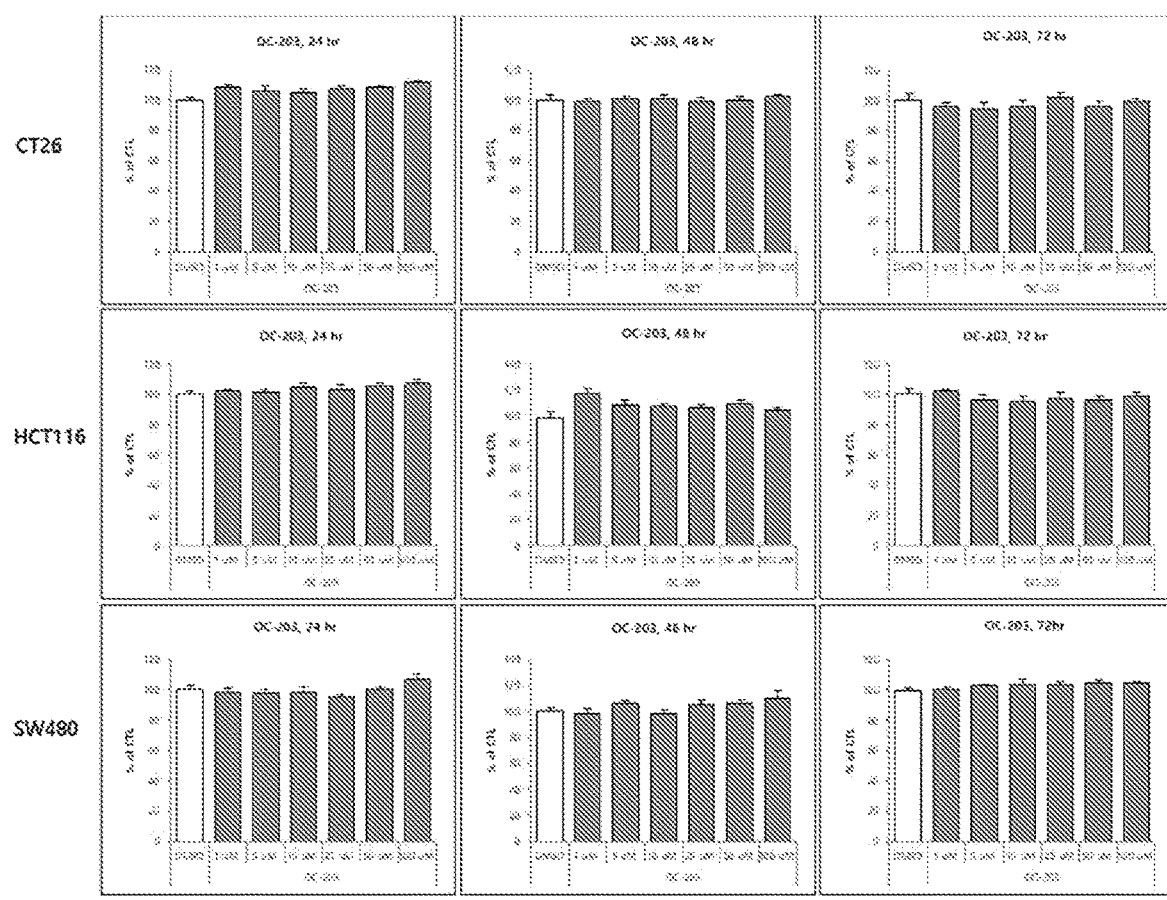

[Figure 4]
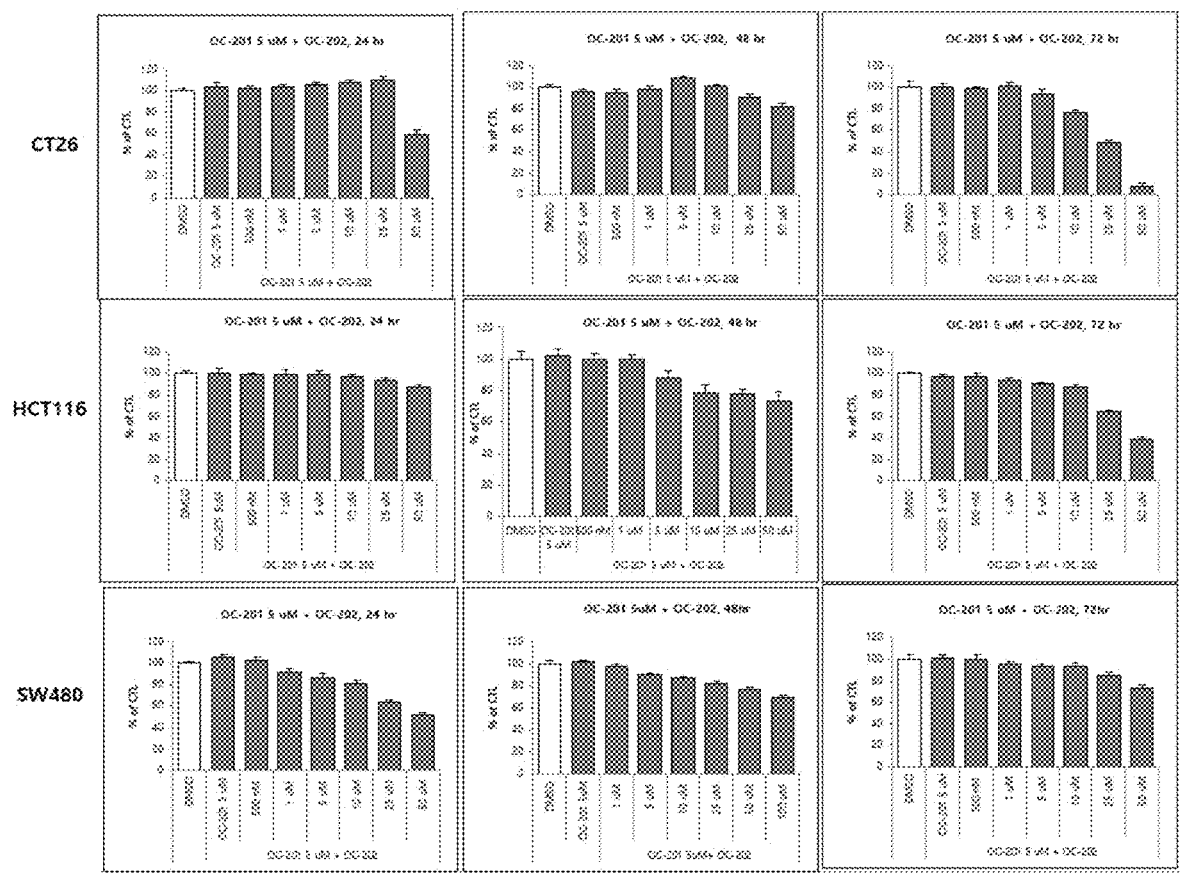

[Figure 5]
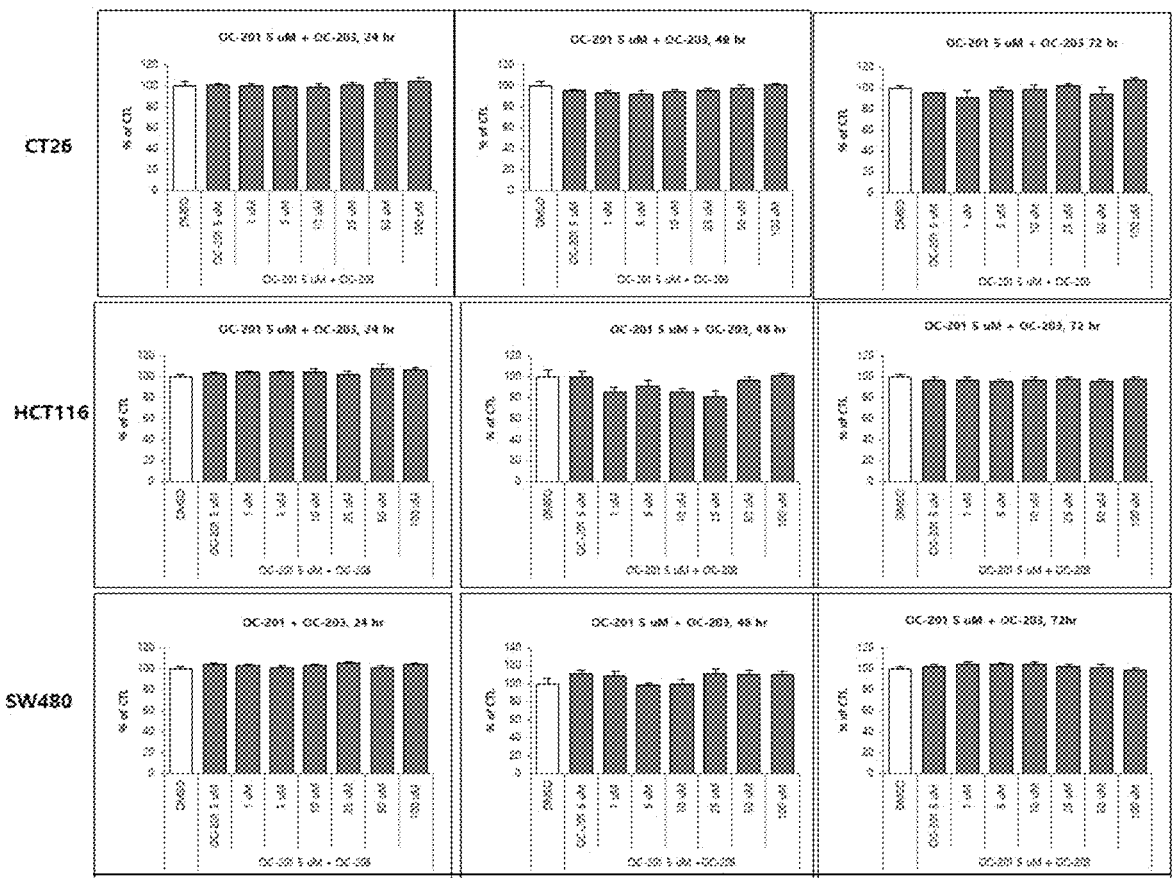

[Figure 6]
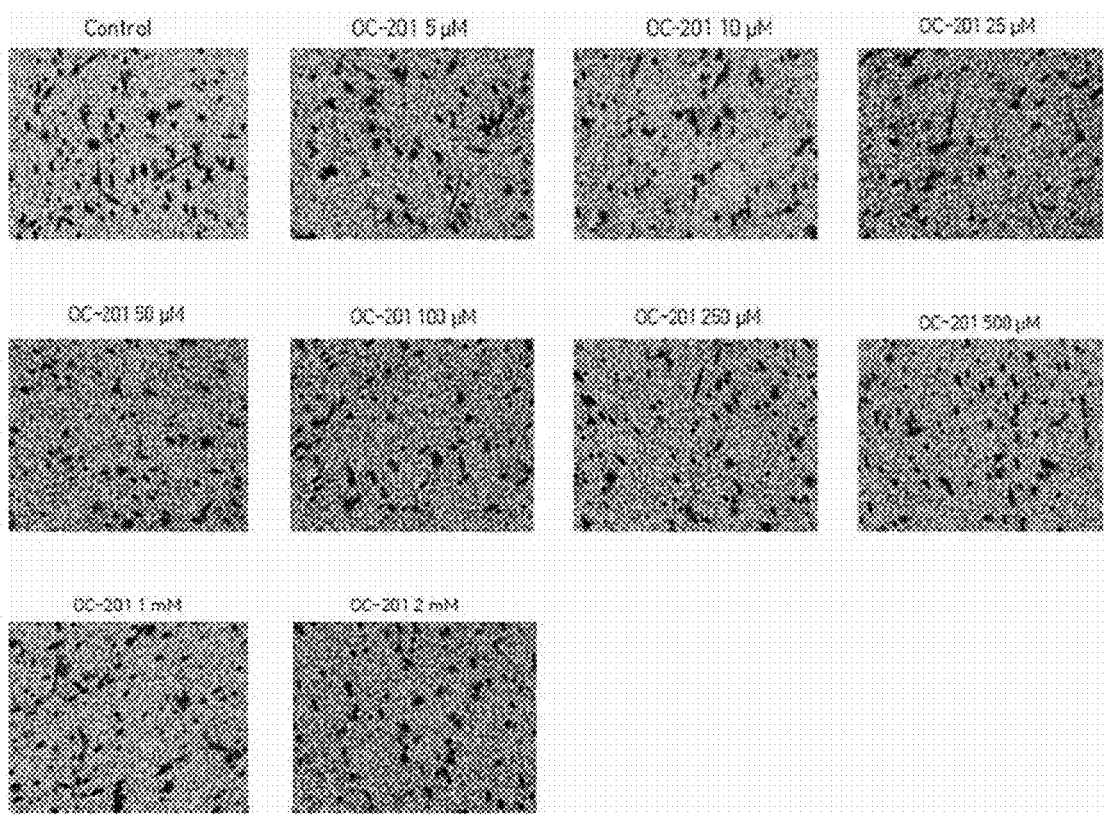

[Figure 7]
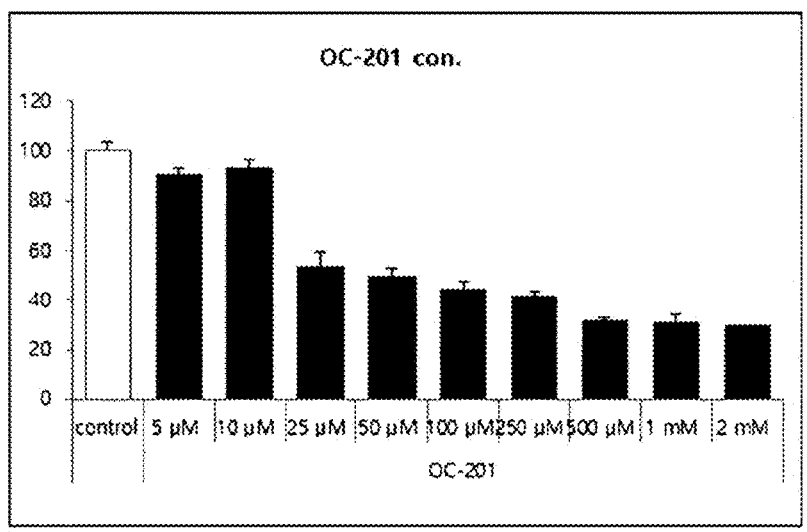

[Figure 8]
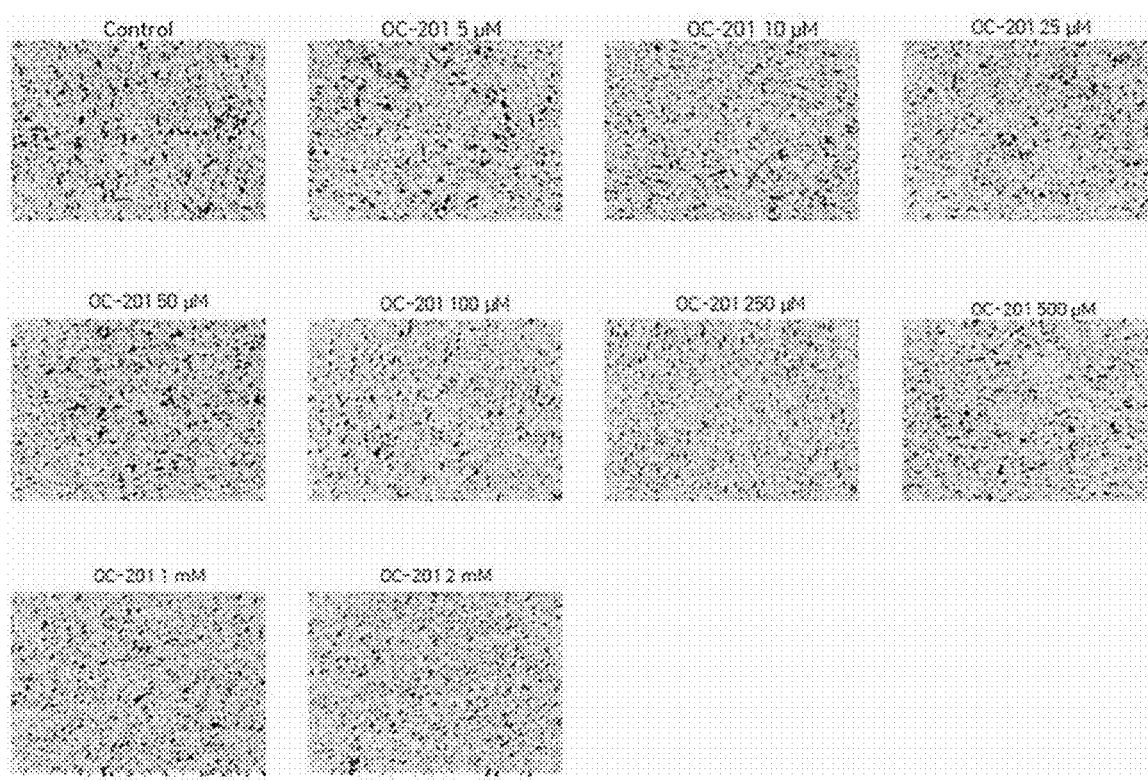

[Figure 9]
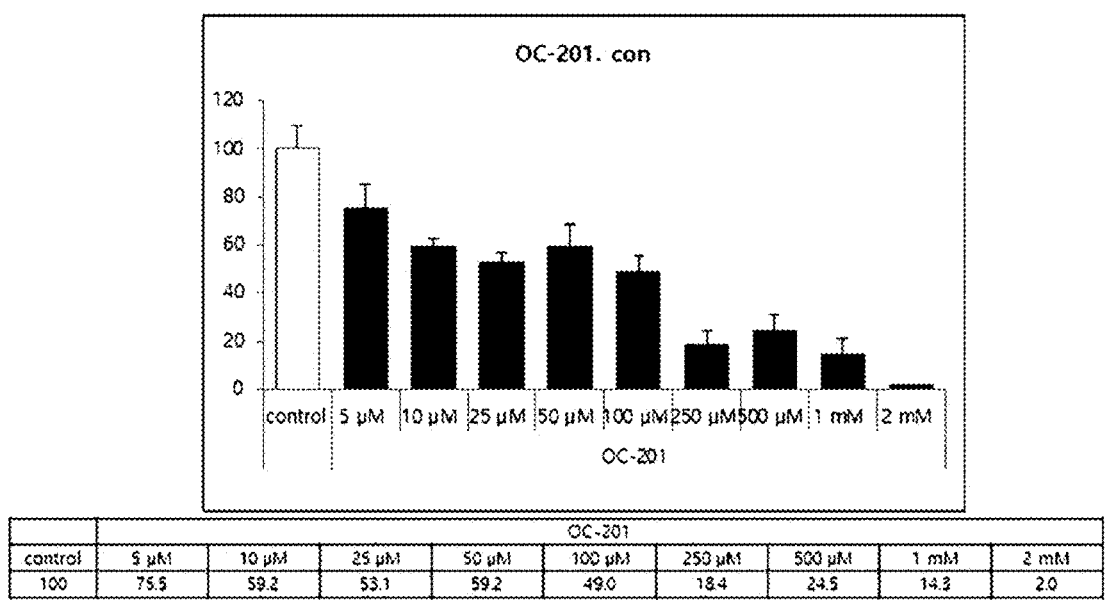

[Figure 10]
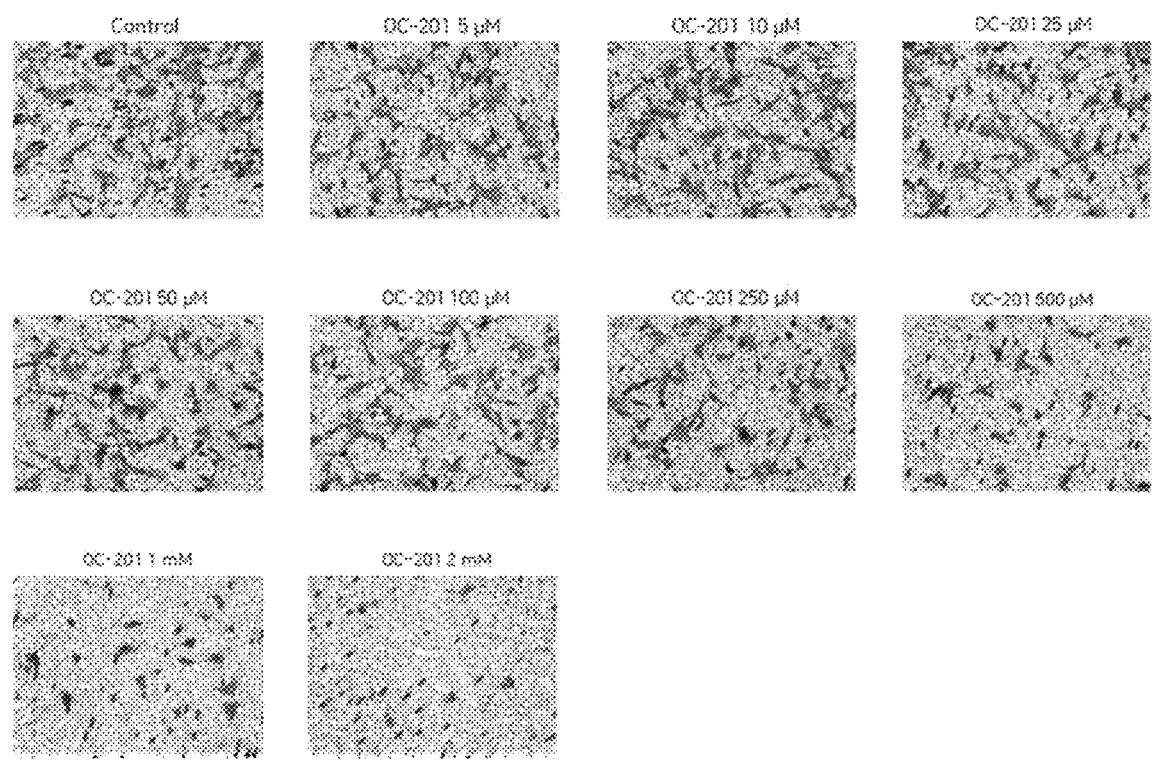

[Figure 11]
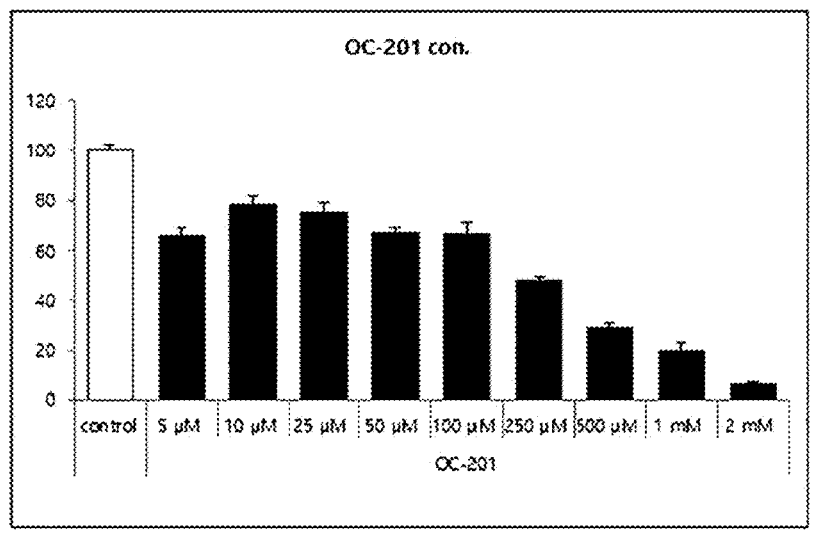

[Figure 12]
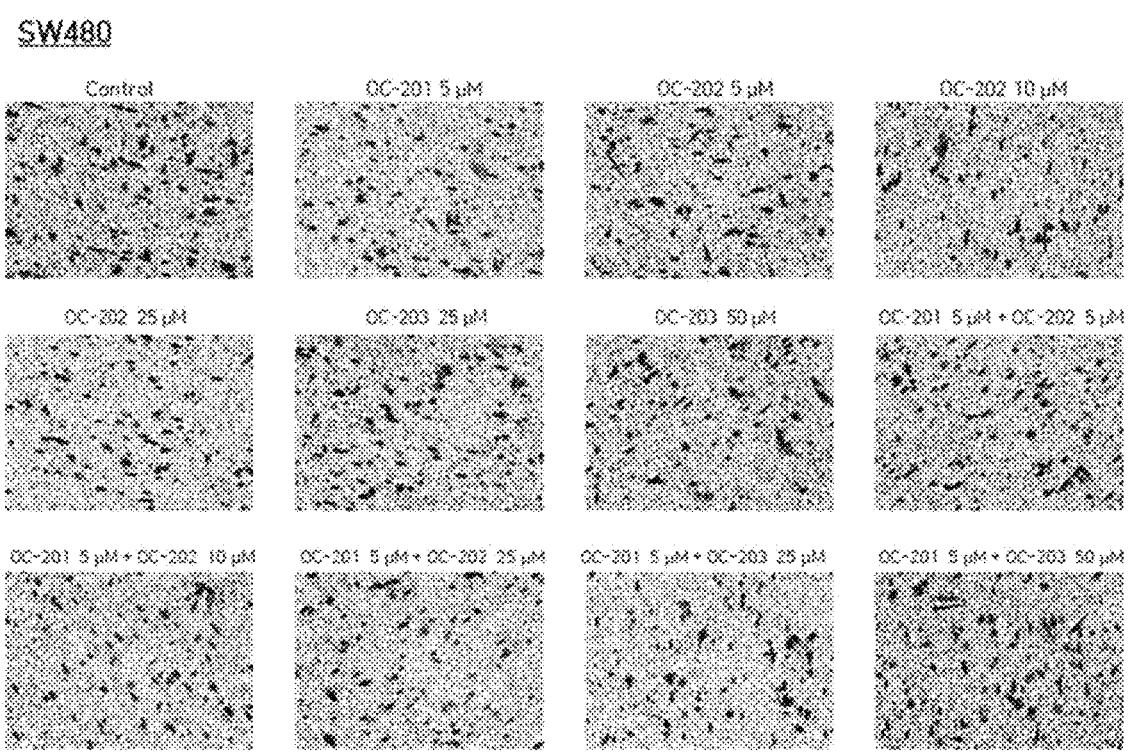

[Figure 13]
SW480
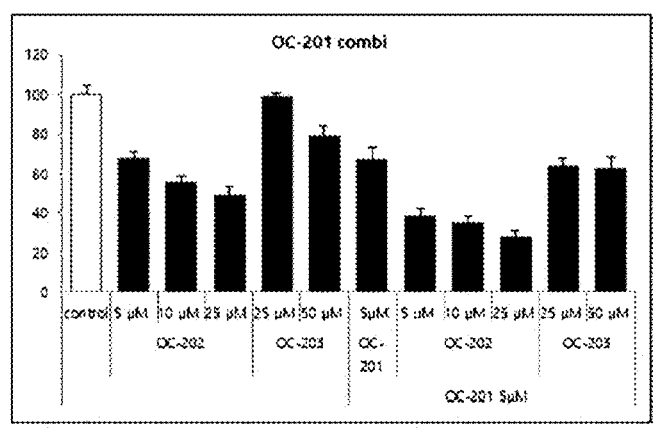
| | OC-202 | | | OC-203 | | OC-201 | OC-201 5μM | | | | |
|---|---|---|---|---|---|---|---|---|---|---|---|
| | | | | | | | OC-202 | | | OC-203 | |
| control | 5 μM | 10 μM | 25 μM | 25 μM | 50 μM | 5μM | 5 μM | 10 μM | 25 μM | 25 μM | 50 μM |
| 100 | 67.9 | 55.2 | 48.5 | 98.5 | 79.1 | 67.2 | 38.1 | 35.1 | 27.6 | 64.2 | 82.7 |

[Figure 14]
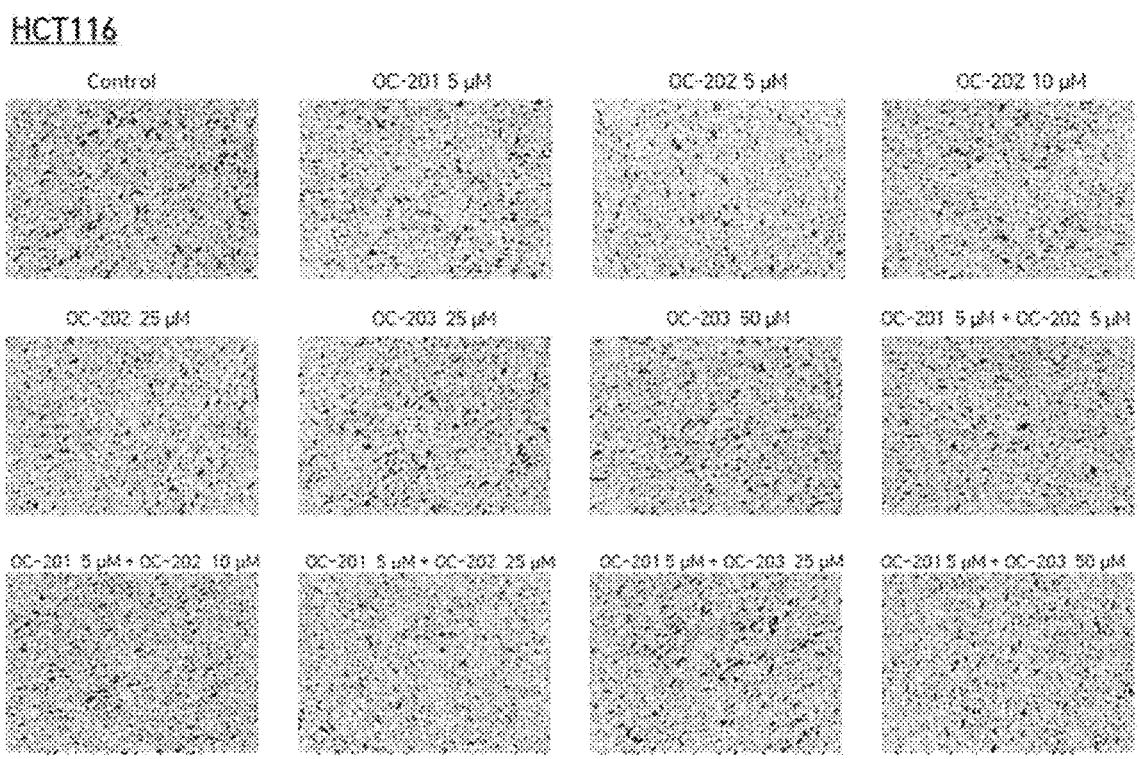

[Figure 15]
HCT116
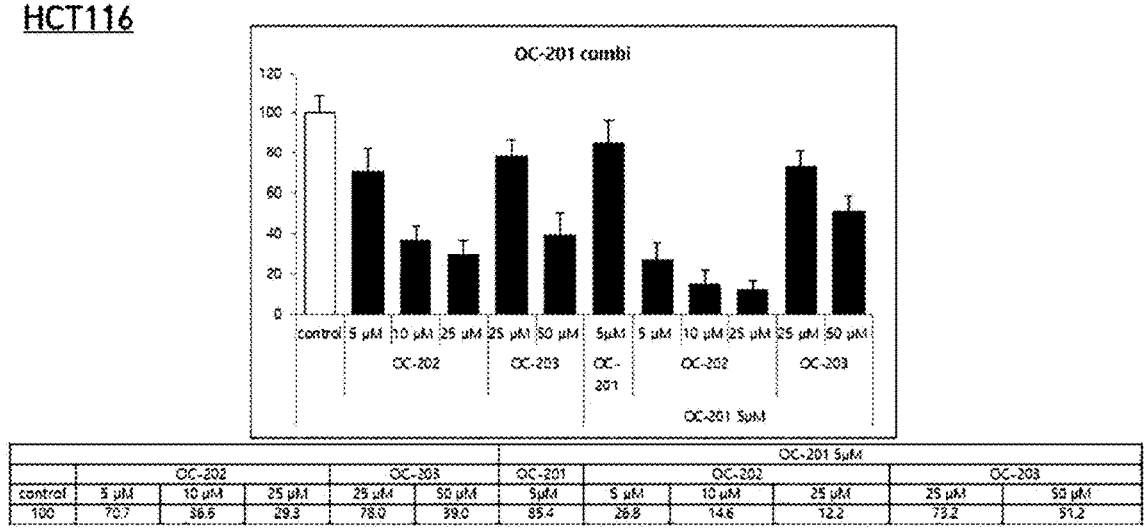

[Figure 16]
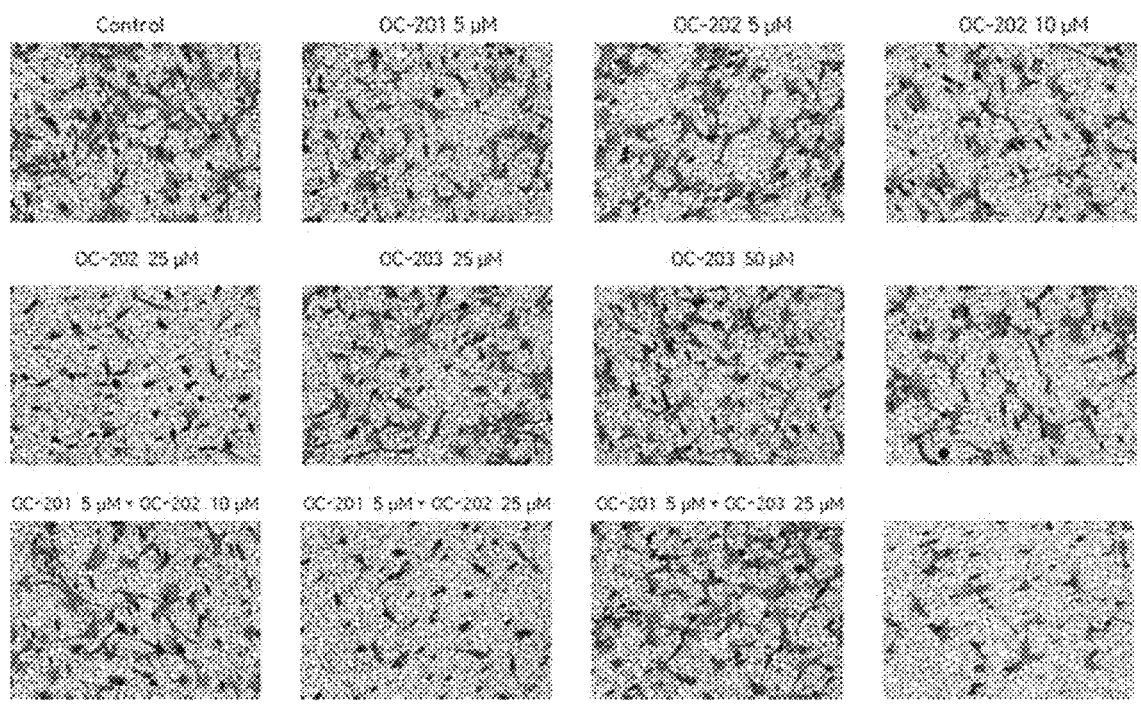

[Figure 17]
CT26
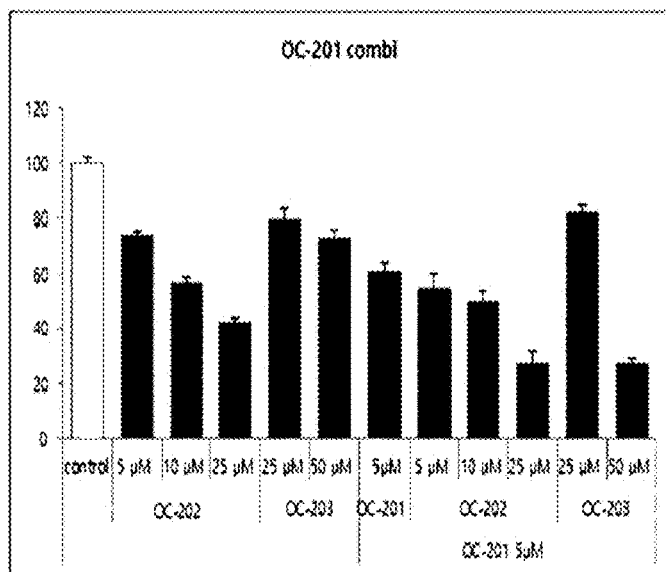
| | OC-202 | | | OC-203 | | OC-201 5μM | | | | | |
|---|---|---|---|---|---|---|---|---|---|---|---|
| | | | | | | | OC-201 | OC-202 | | | OC-203 |
| control | 5 μM | 10 μM | 25 μM | 25 μM | 50 μM | 5μM | 5 μM | 10 μM | 25 μM | 25 μM | 50 μM |
| 100 | 74.0 | 56.8 | 41.9 | 79.3 | 72.7 | 61.2 | 55.1 | 49.8 | 26.9 | 82.4 | 26.9 |

[Figure 18]

[Figure 19]
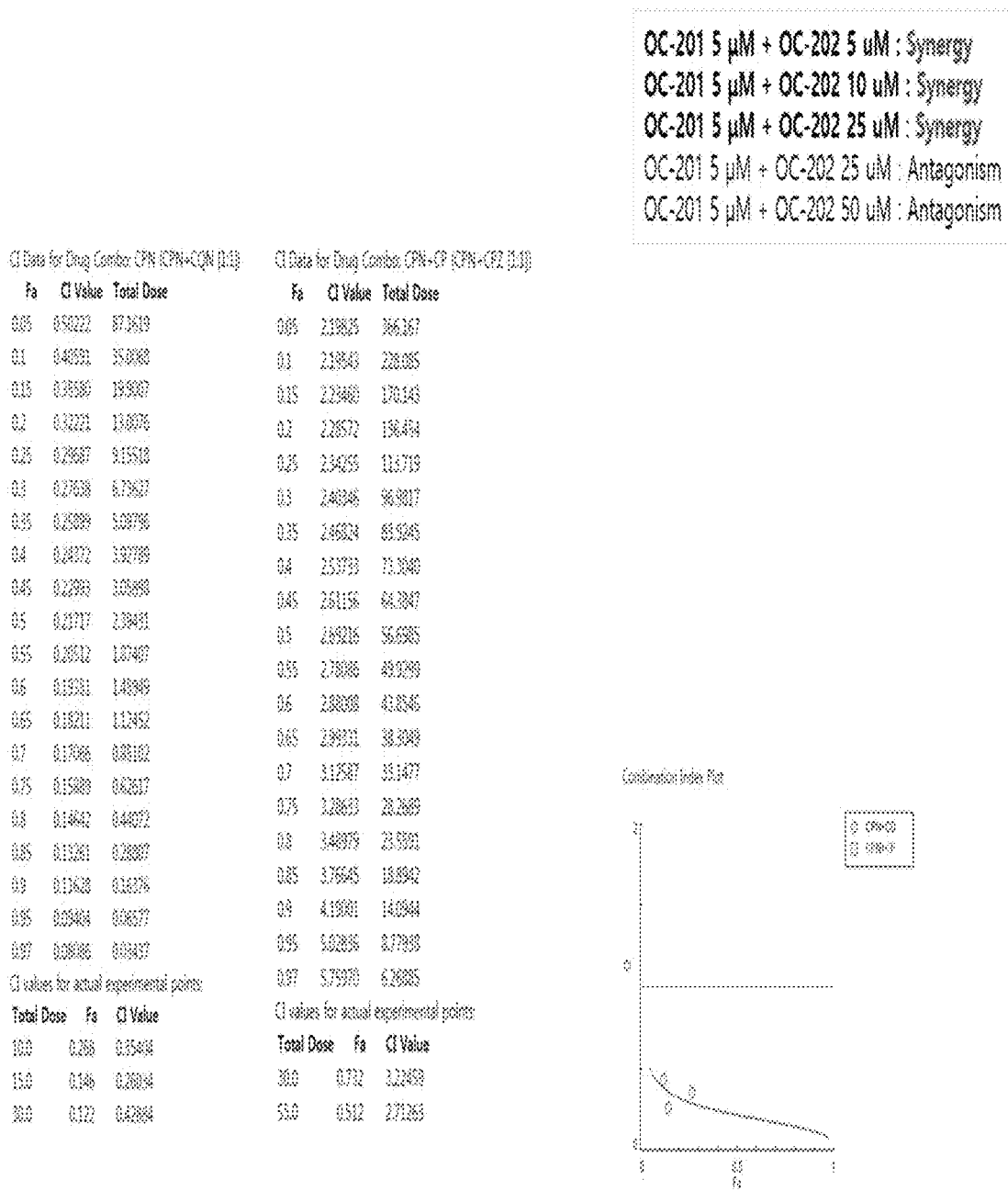

[Figure 20]
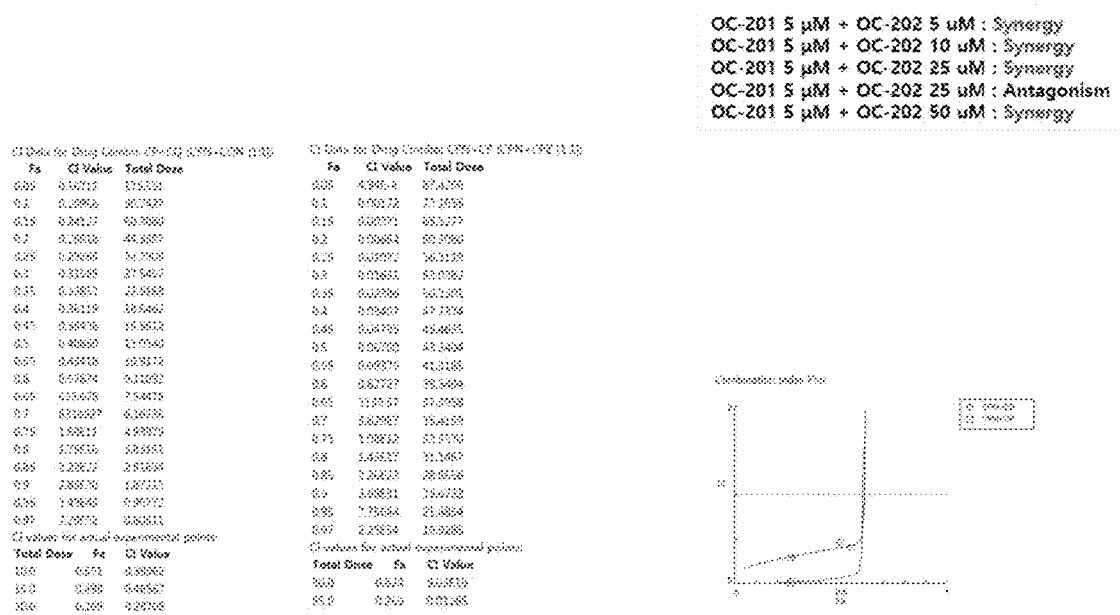

[Figure 21]
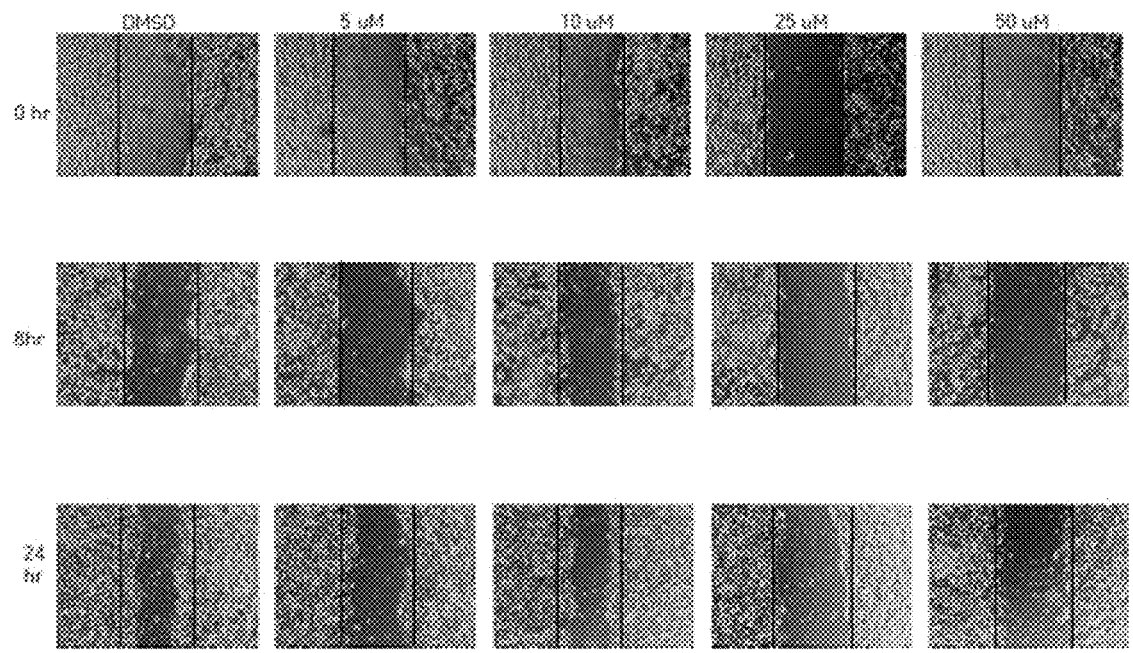

[Figure 22]
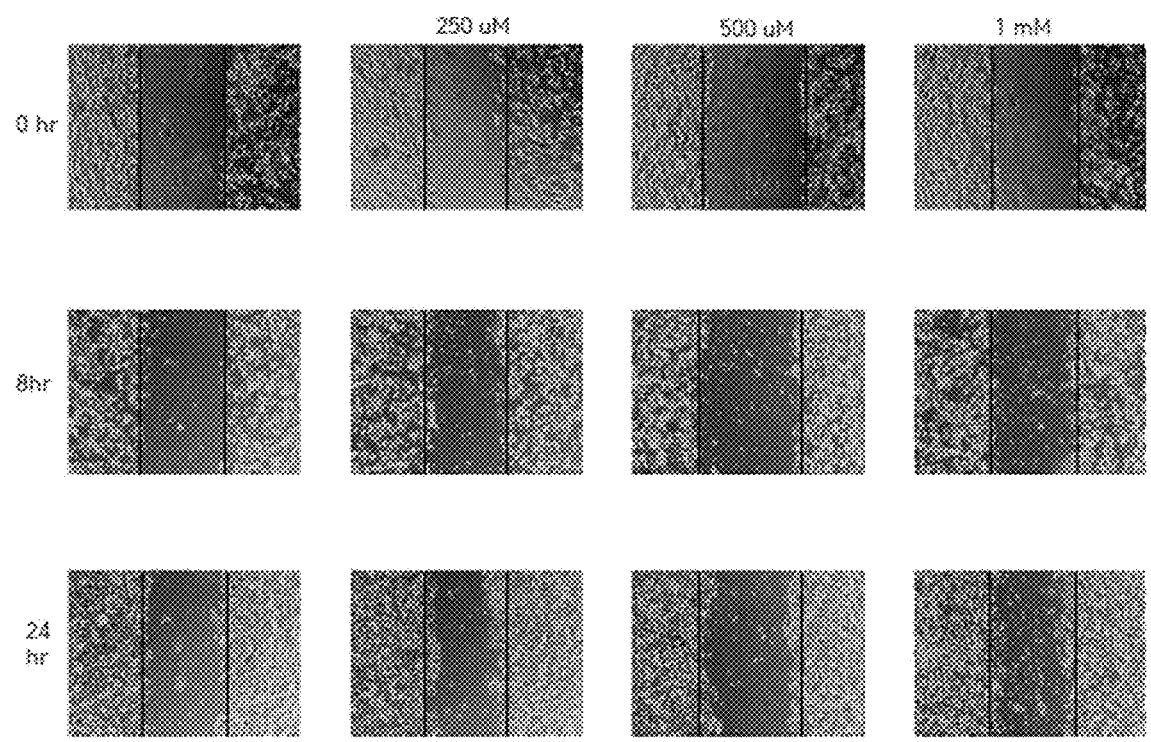

[Figure 23]
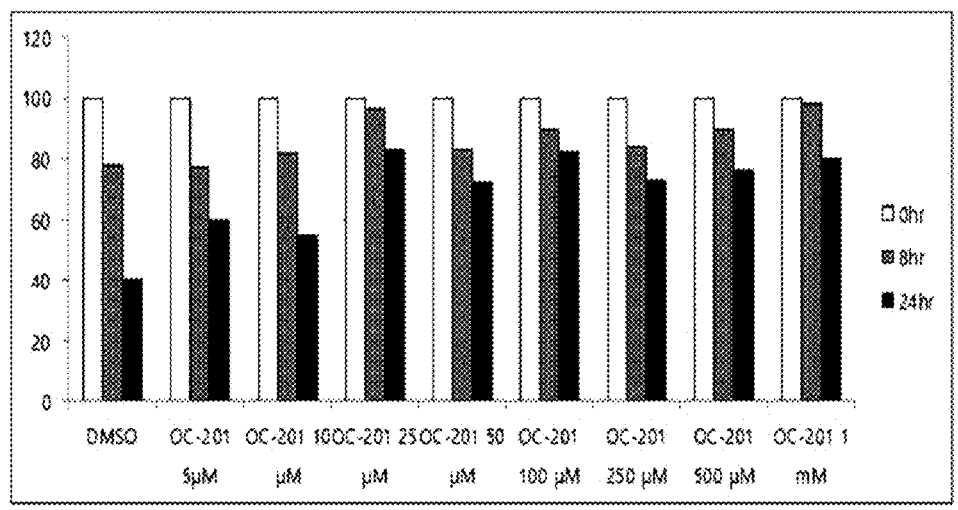
Migration rate = (mean area occupied by cells / mean original area) x 100

[Figure 24]
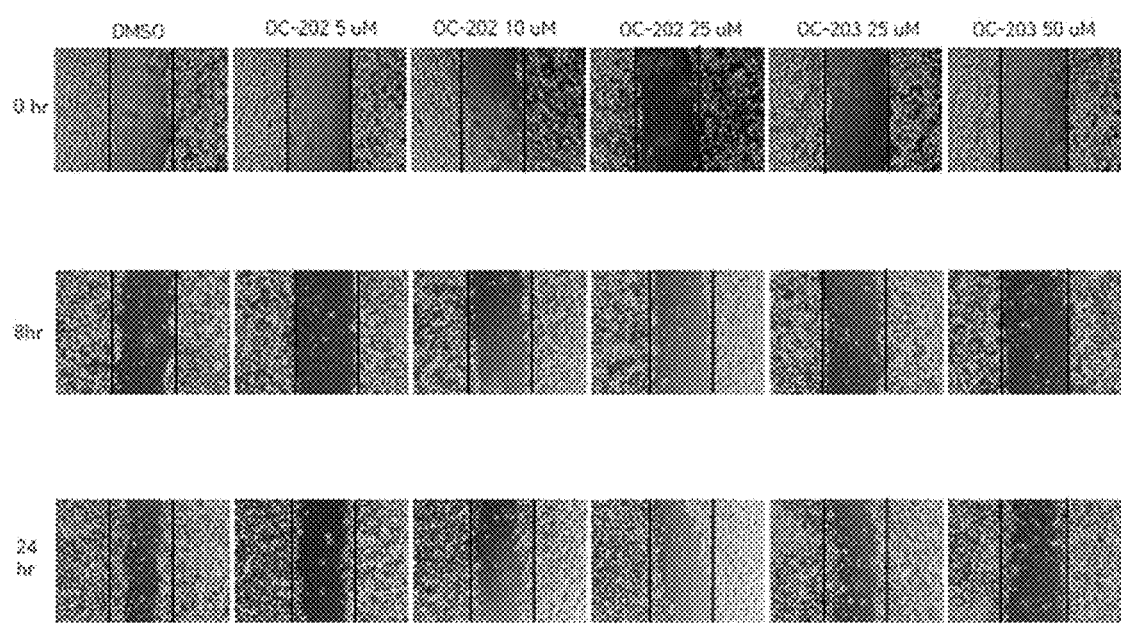

[Figure 25]
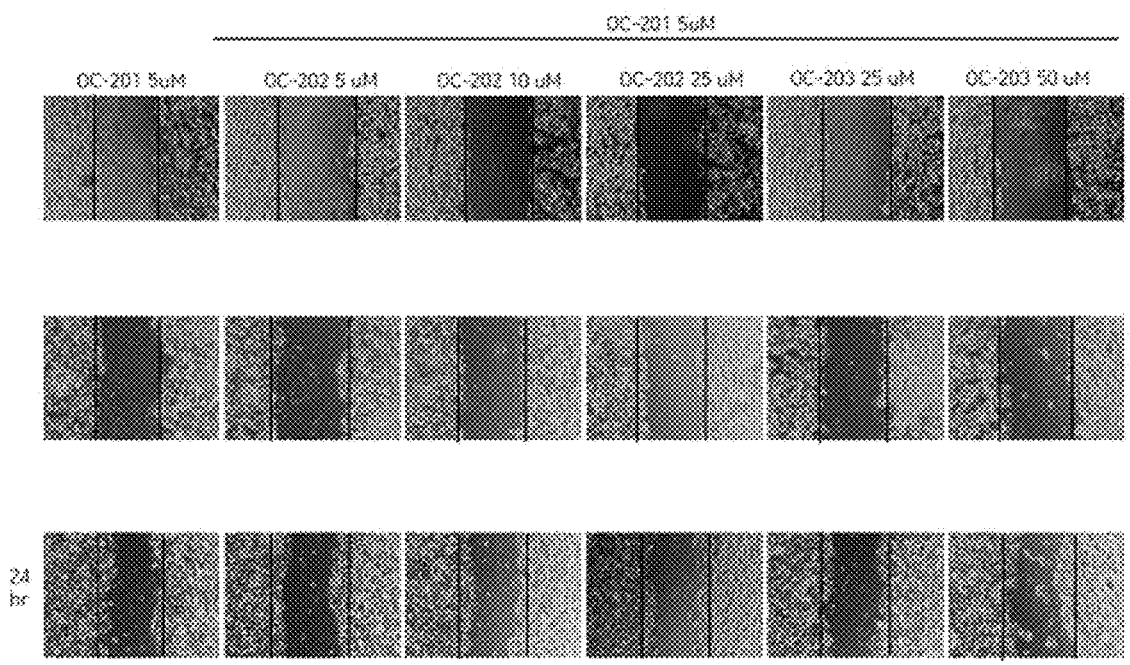

[Figure 26]
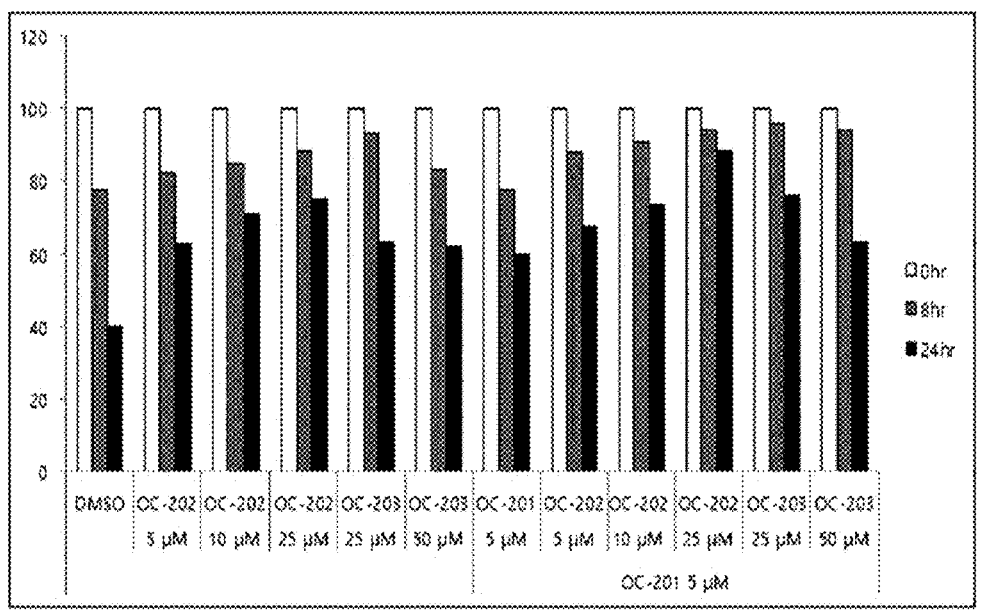

[Figure 27]
HCT116
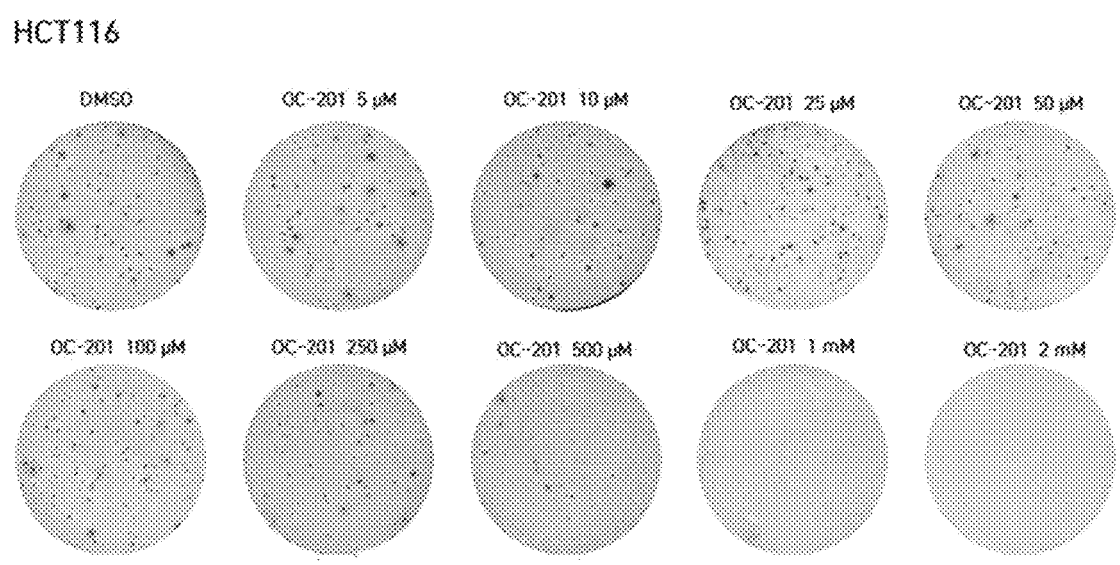

[Figure 28]
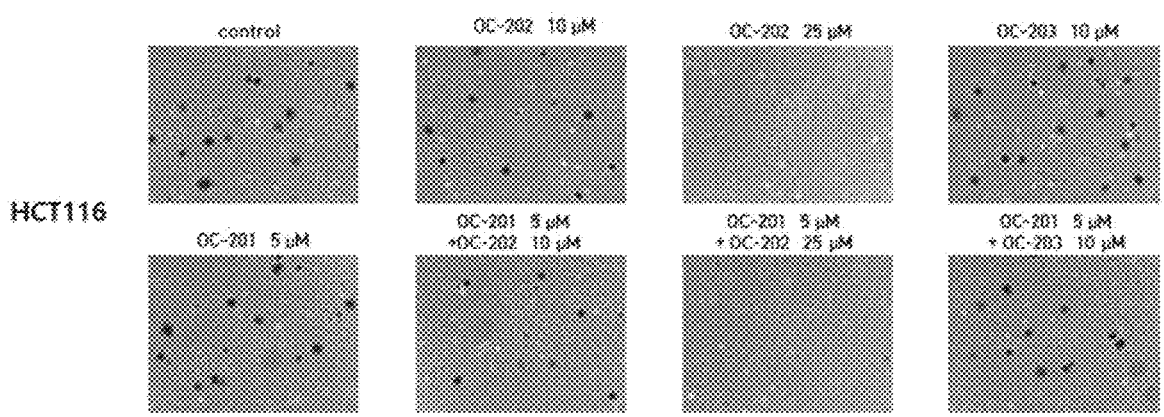

[Figure 29]
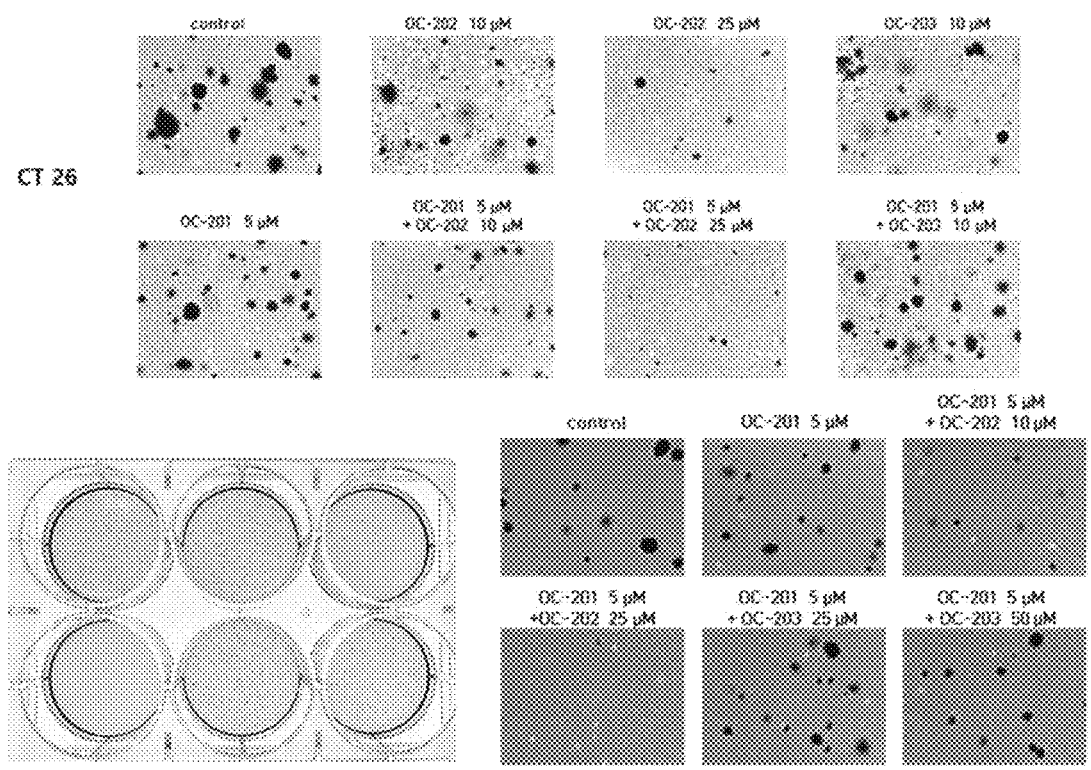

[Figure 30]
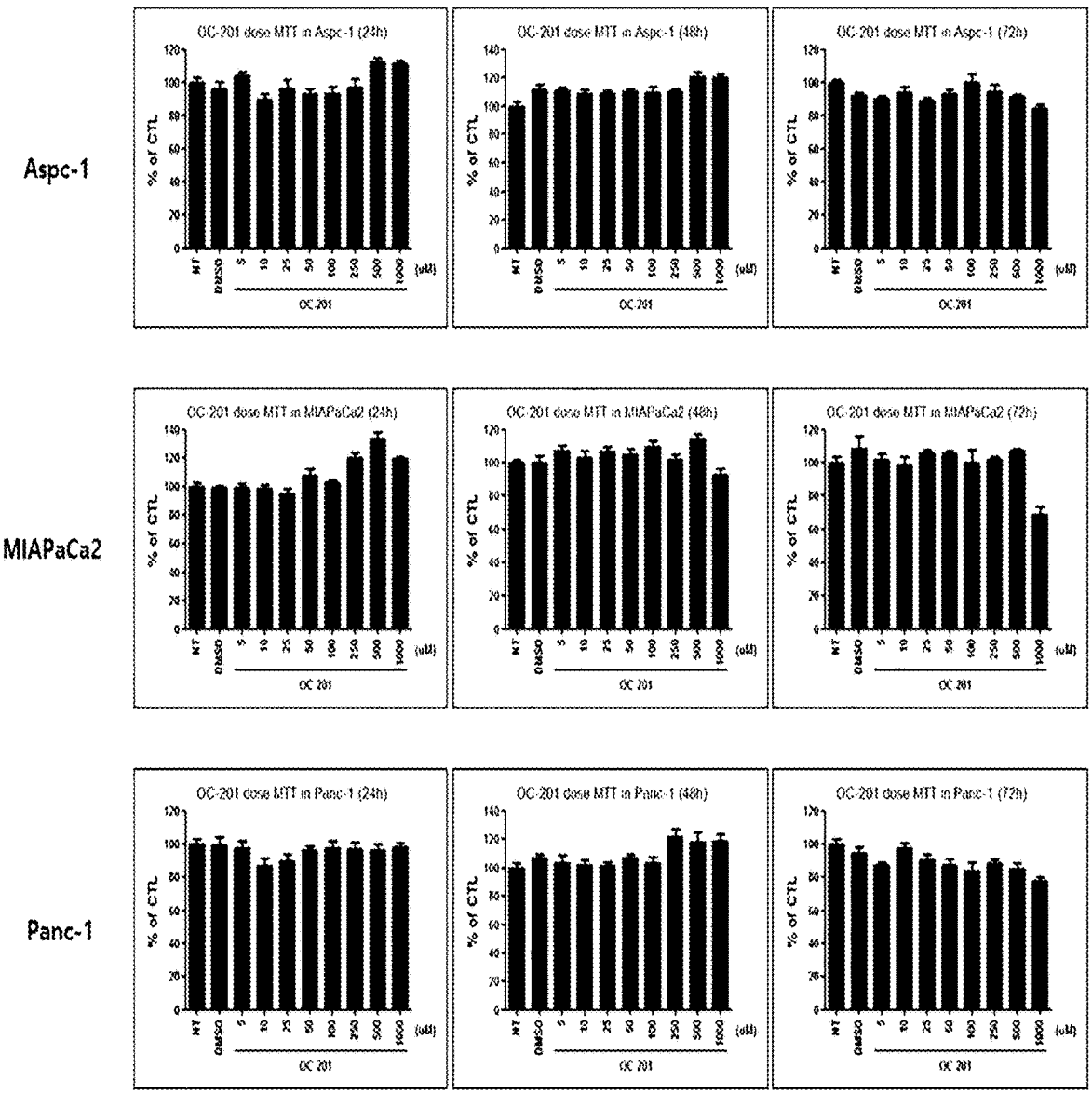

[Figure 31]
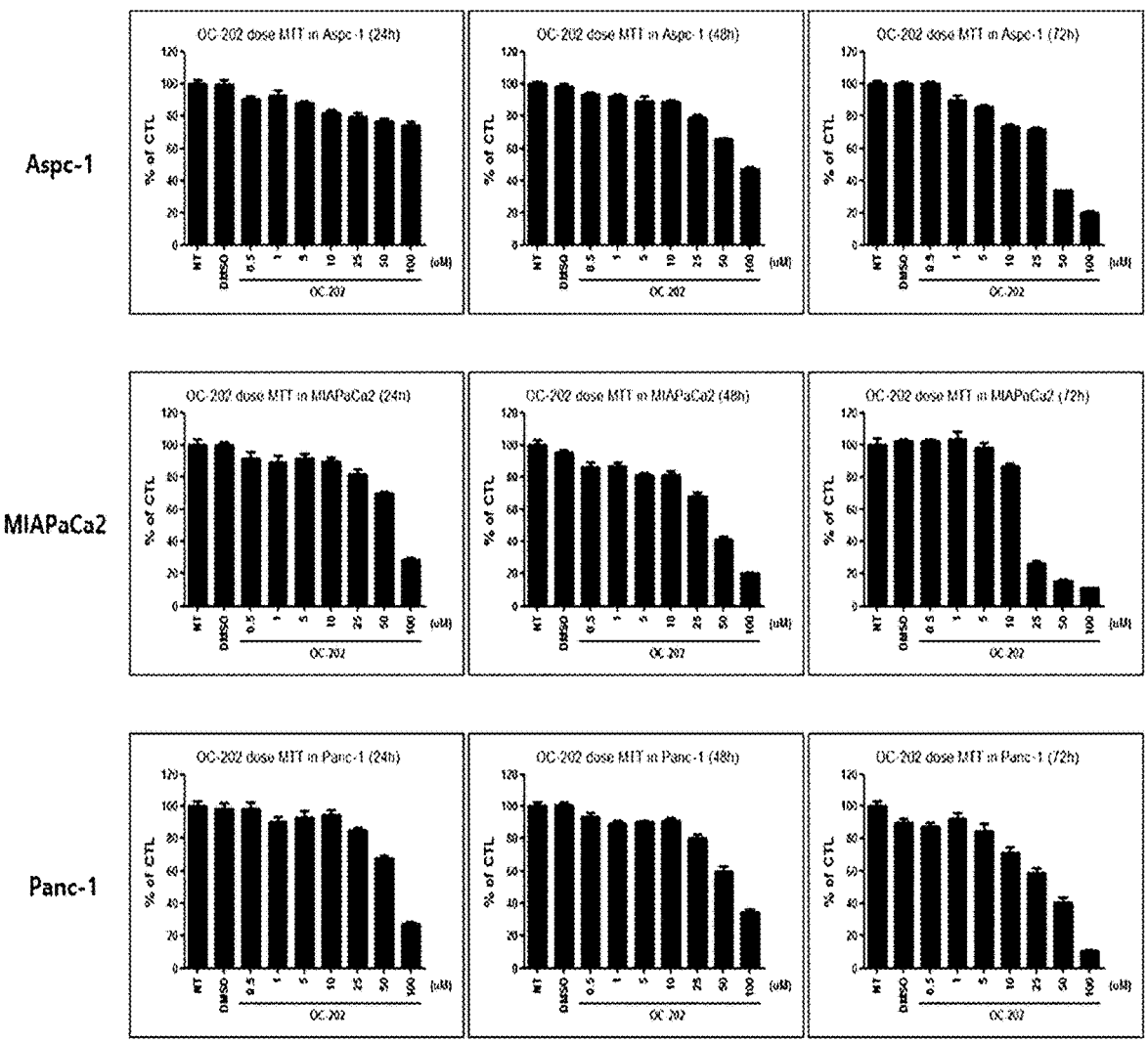

[Figure 32]
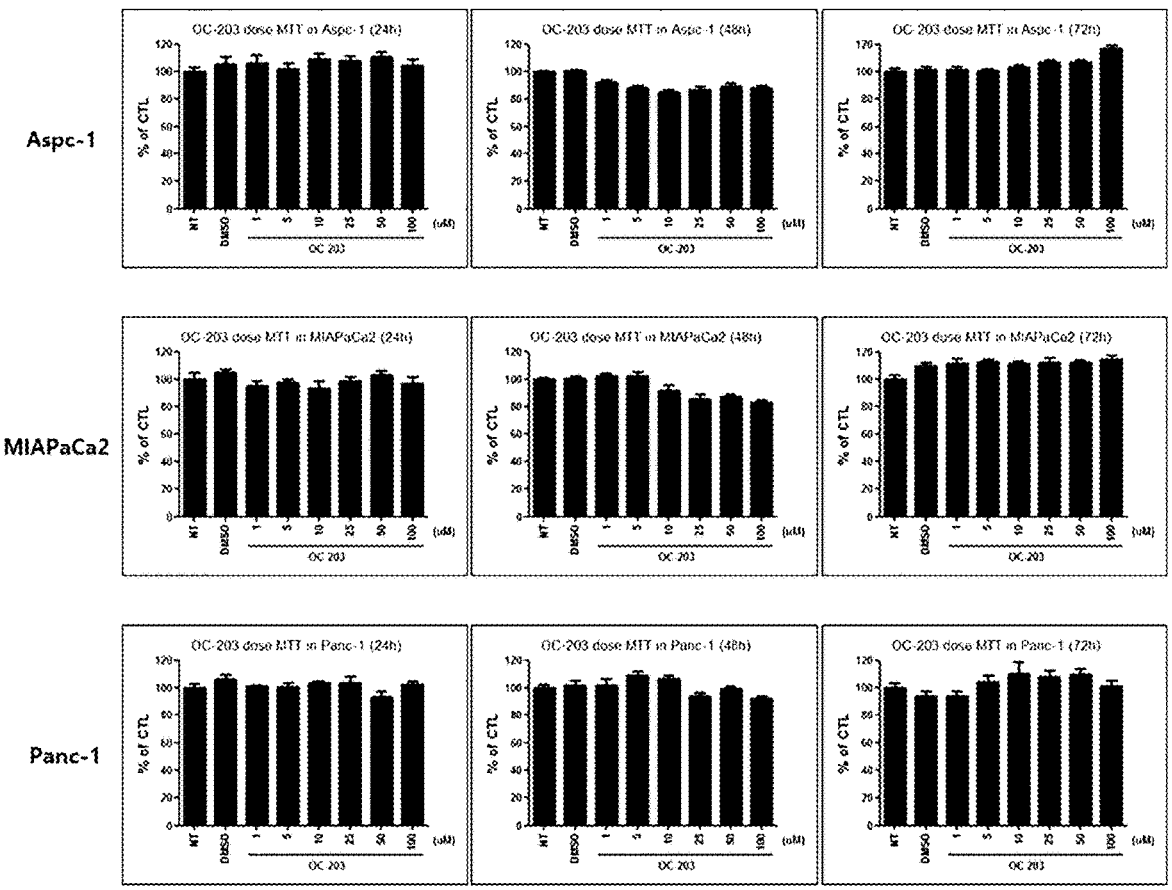

[Figure 33]
<Aspc-1>
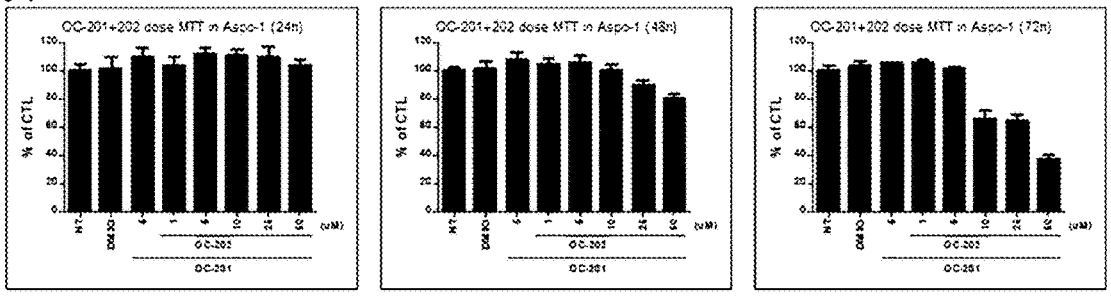
<MIAPaCa2>
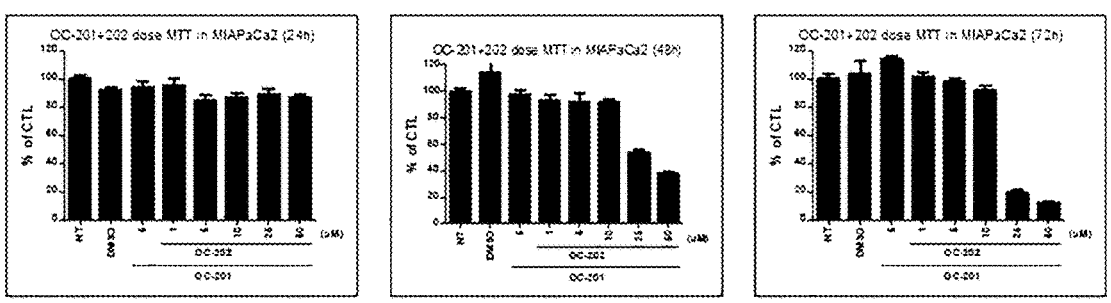
<Panc-1>
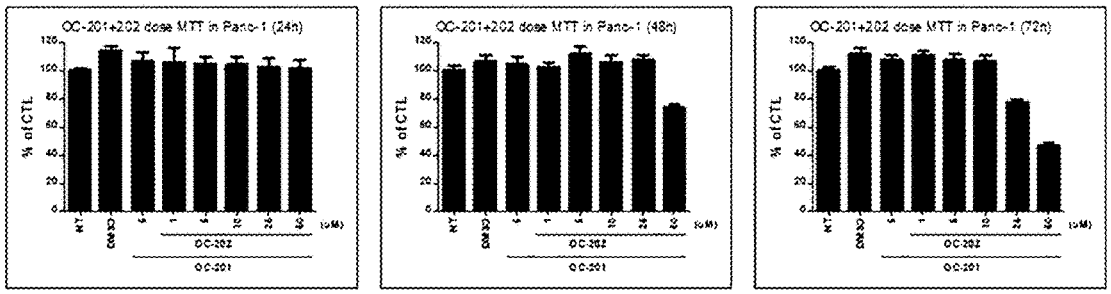

[Figure 34]
Aspc-1
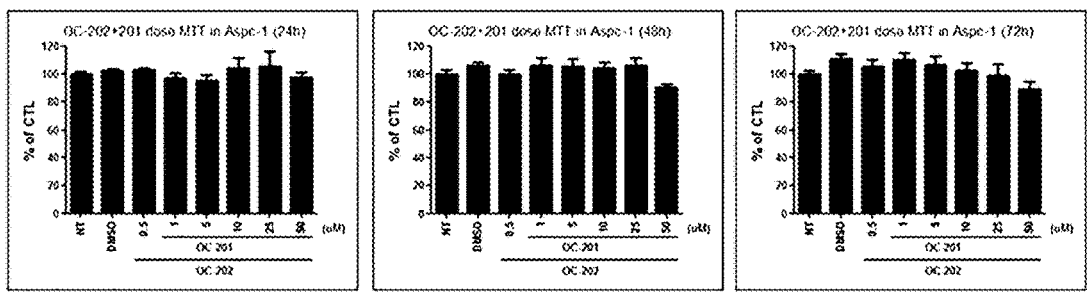
MIAPaCa2
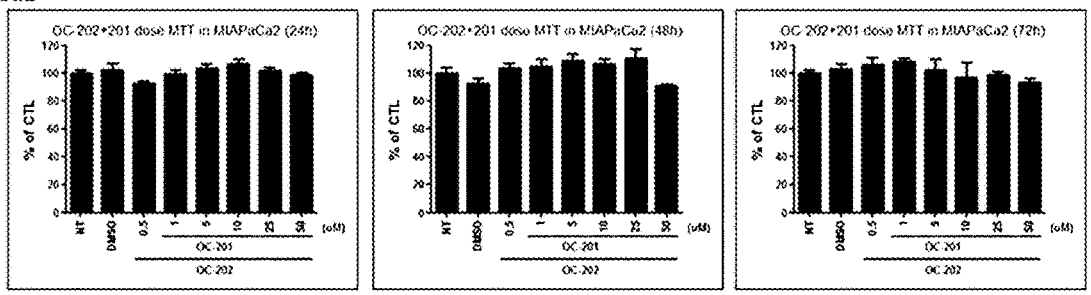
Panc-1
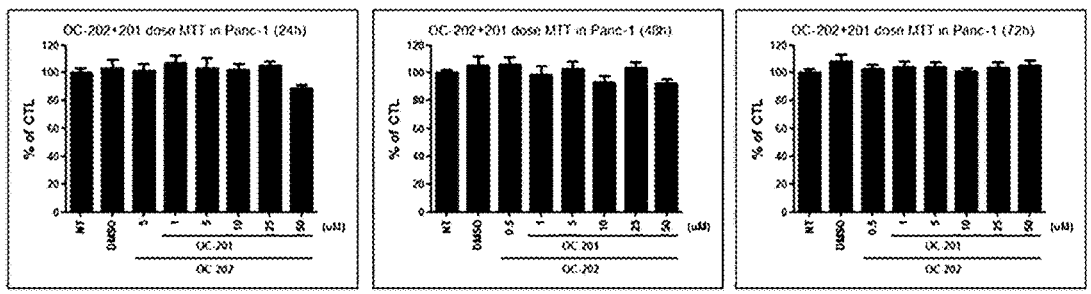

[Figure 35]
Aspc-1
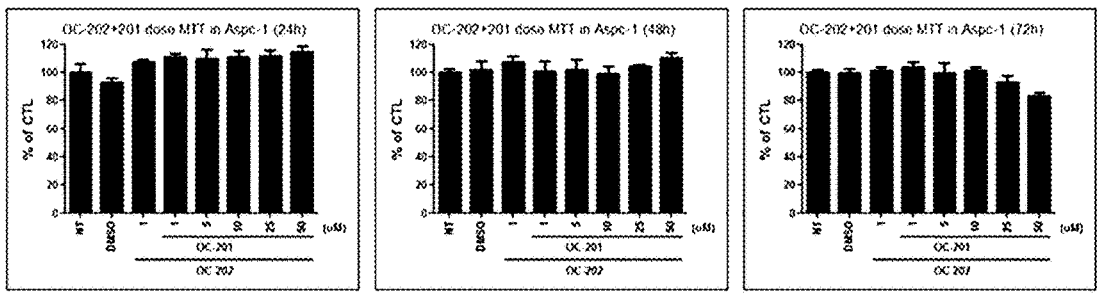
MIAPaCa2
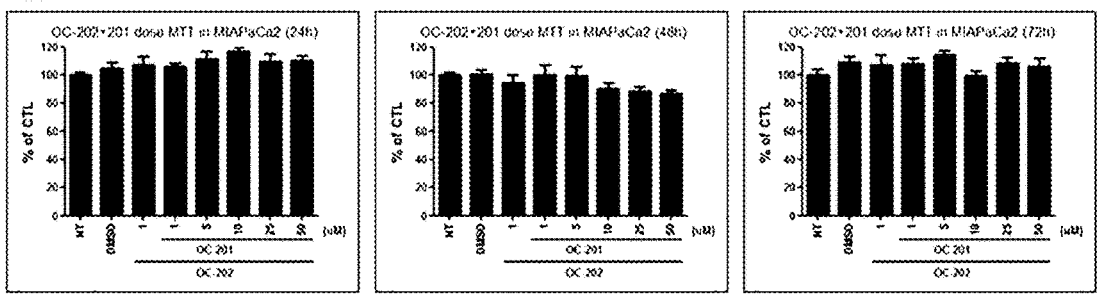
Panc-1
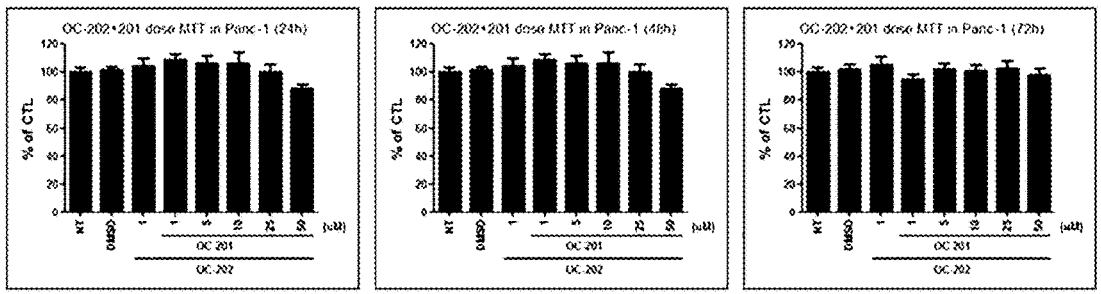

[Figure 36]
Aspc-1
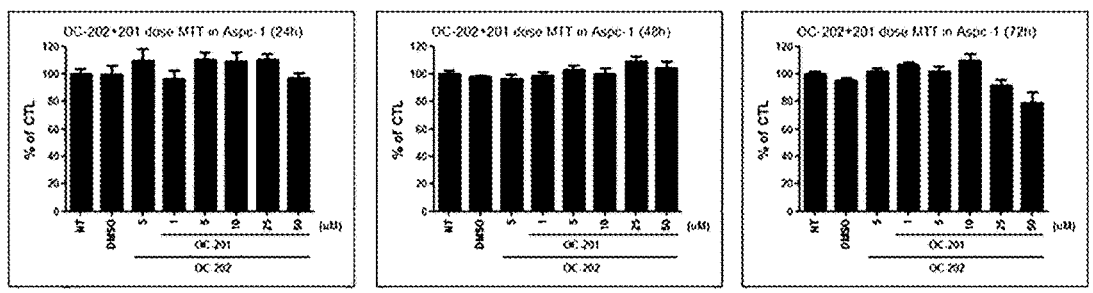
MIAPaCa2
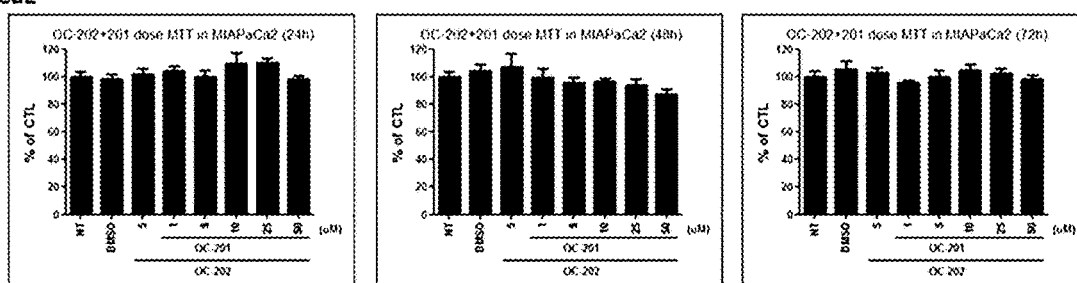
Panc-1
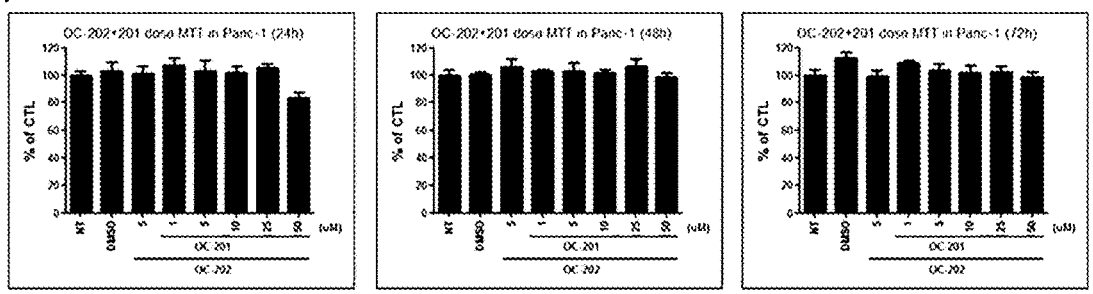

[Figure 37]
<Aspc-1>
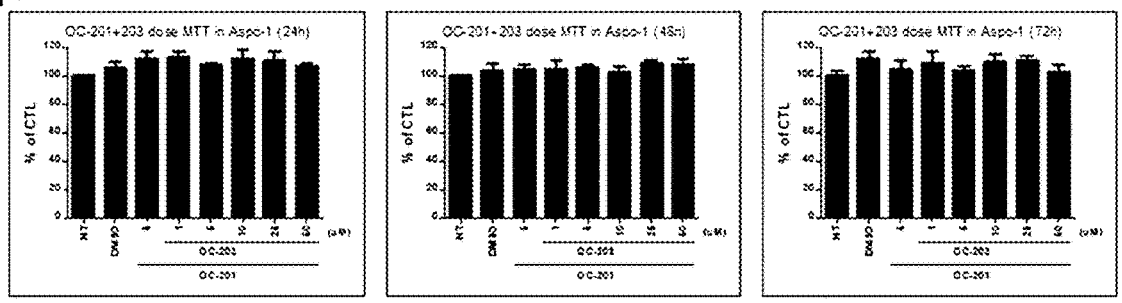
<MIAPaCa2>
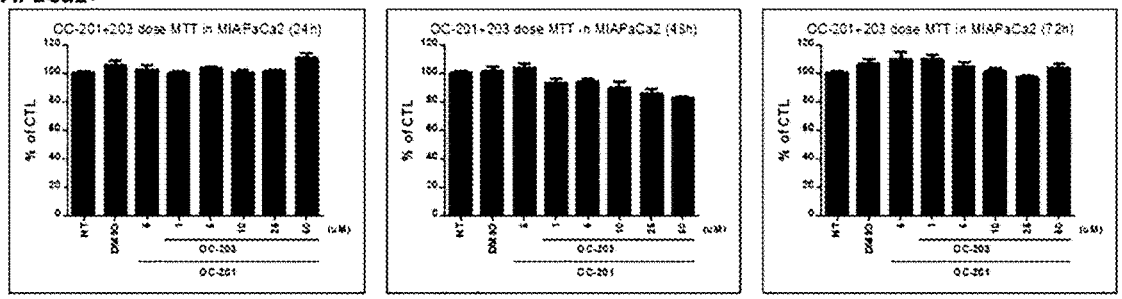
<Panc-1>
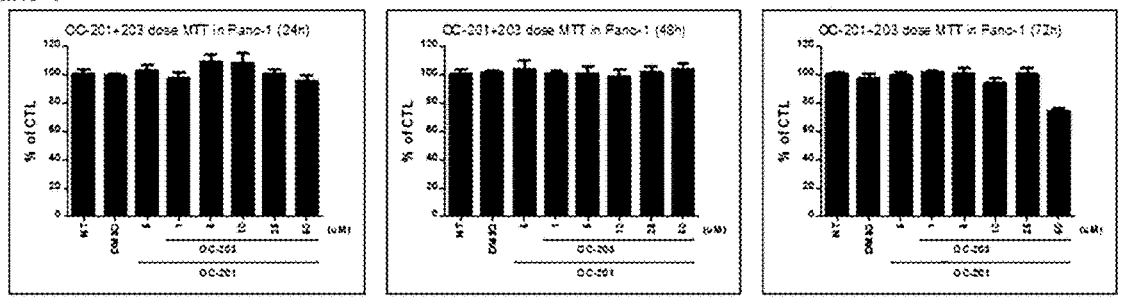

[Figur 38]
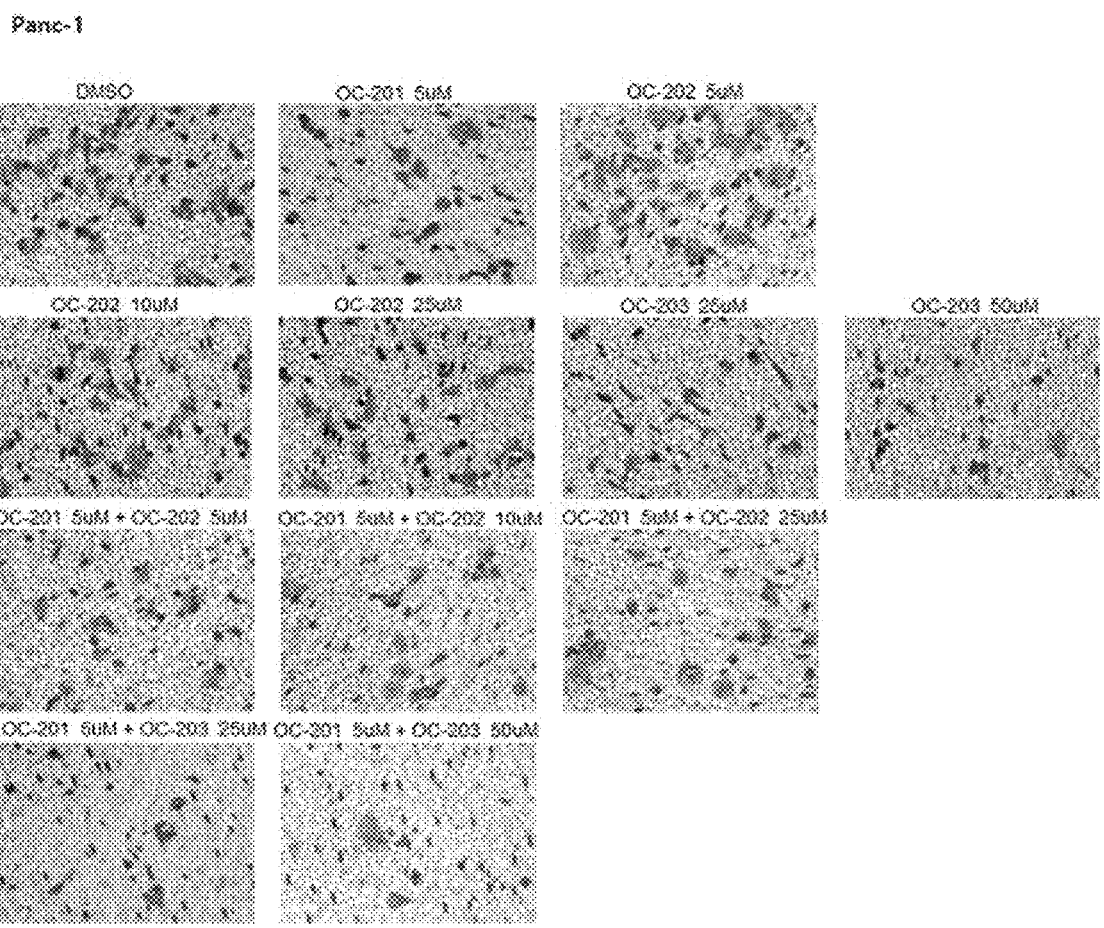

[Figure 39]
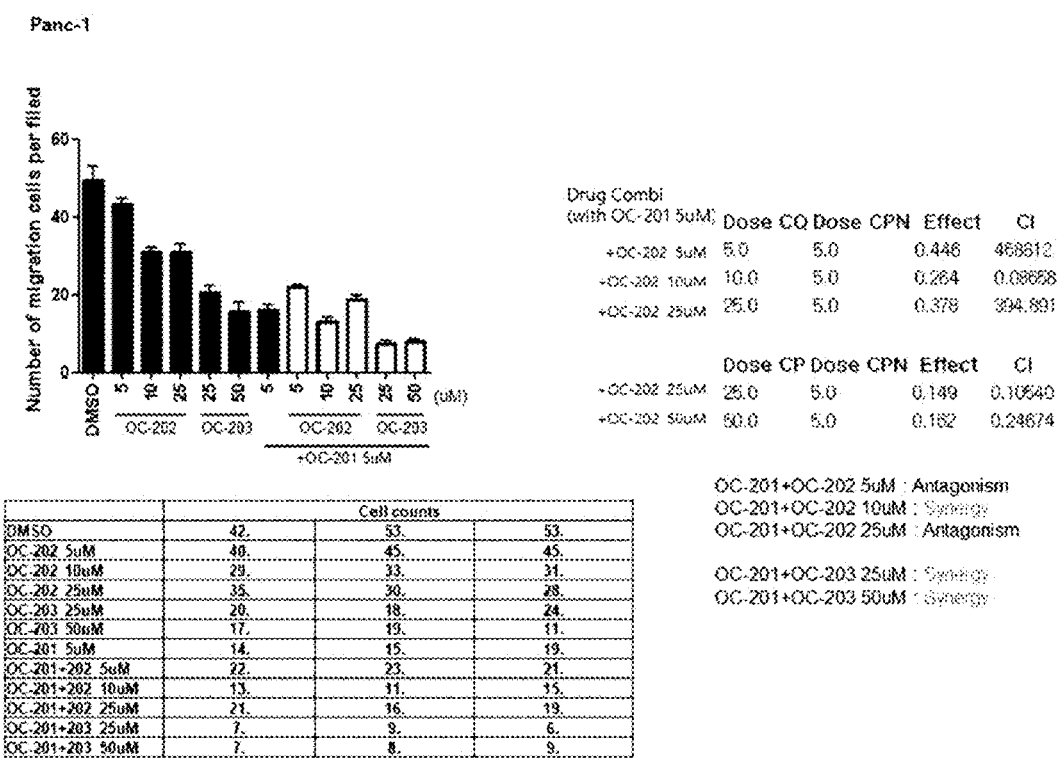

[Figure 40]
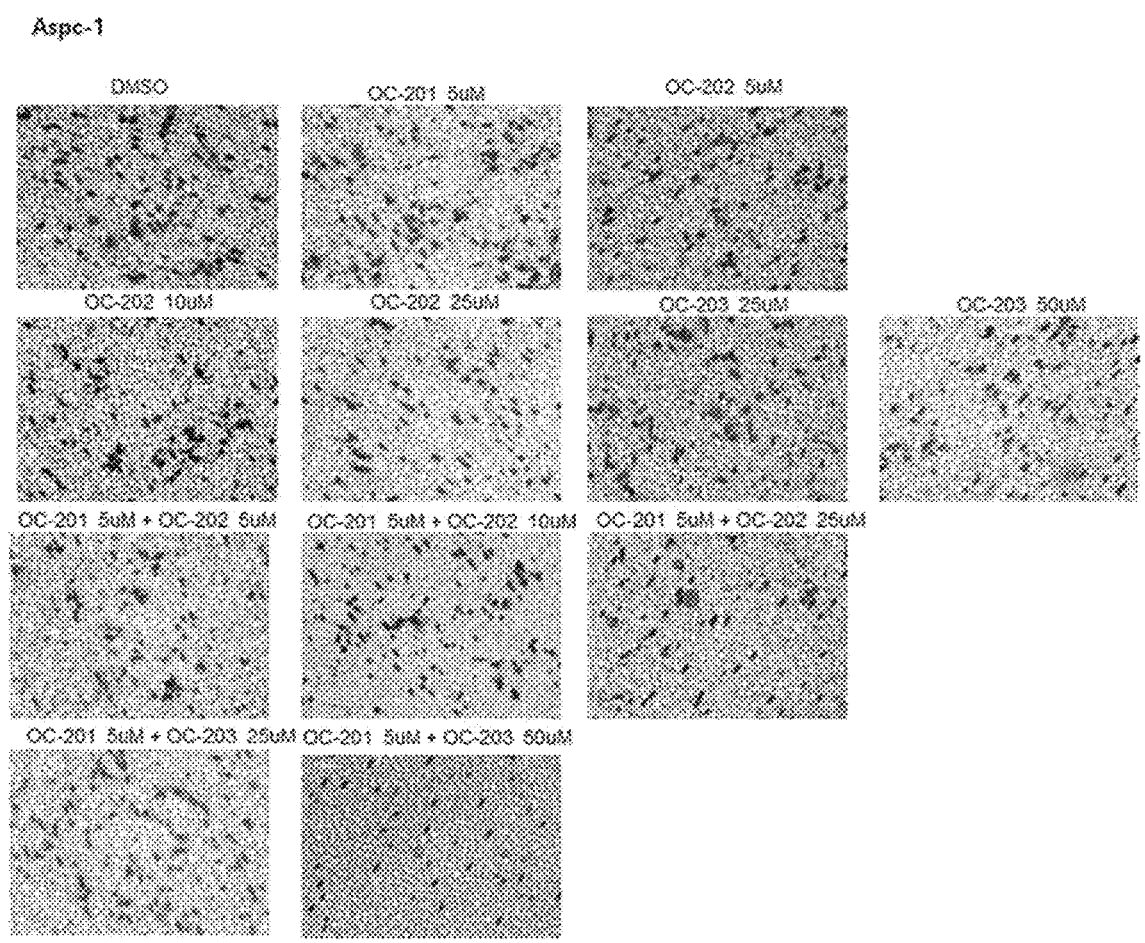

[Figure 41]
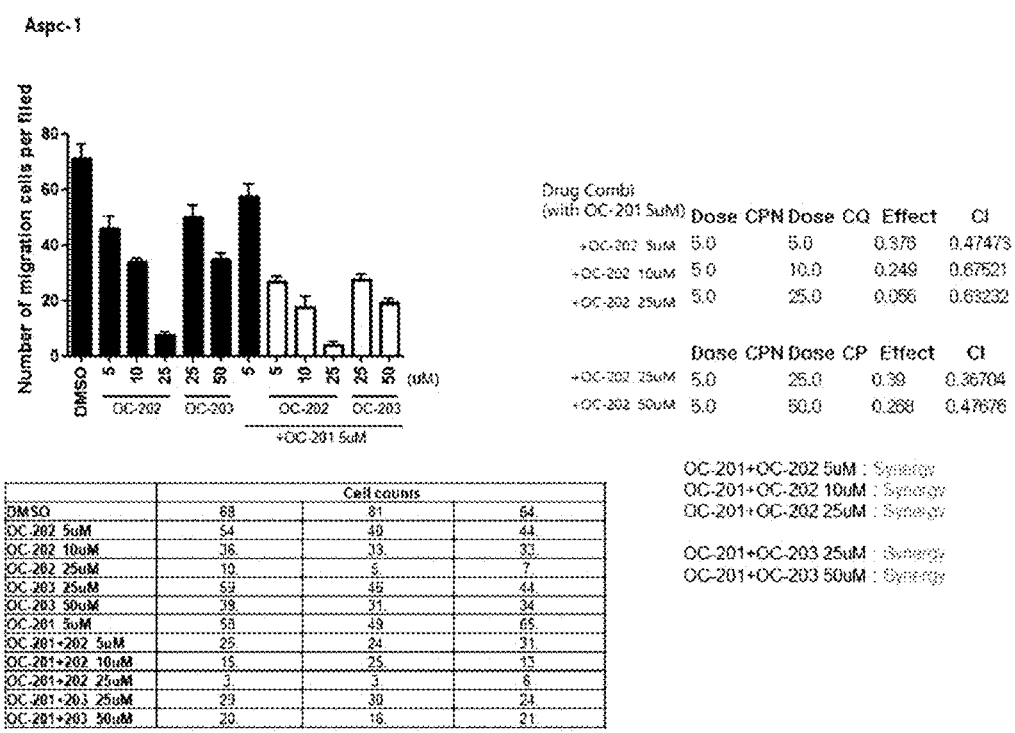

[Figure 42]
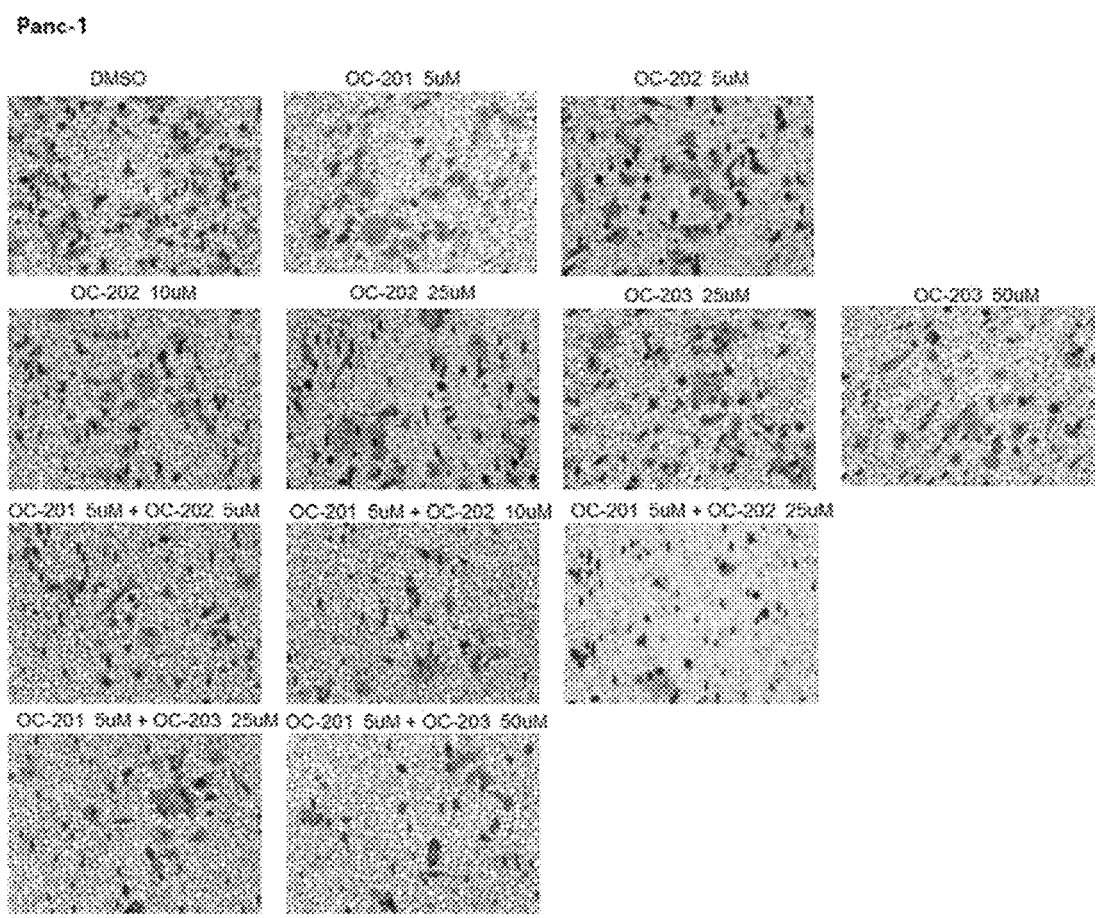

[Figure 43]
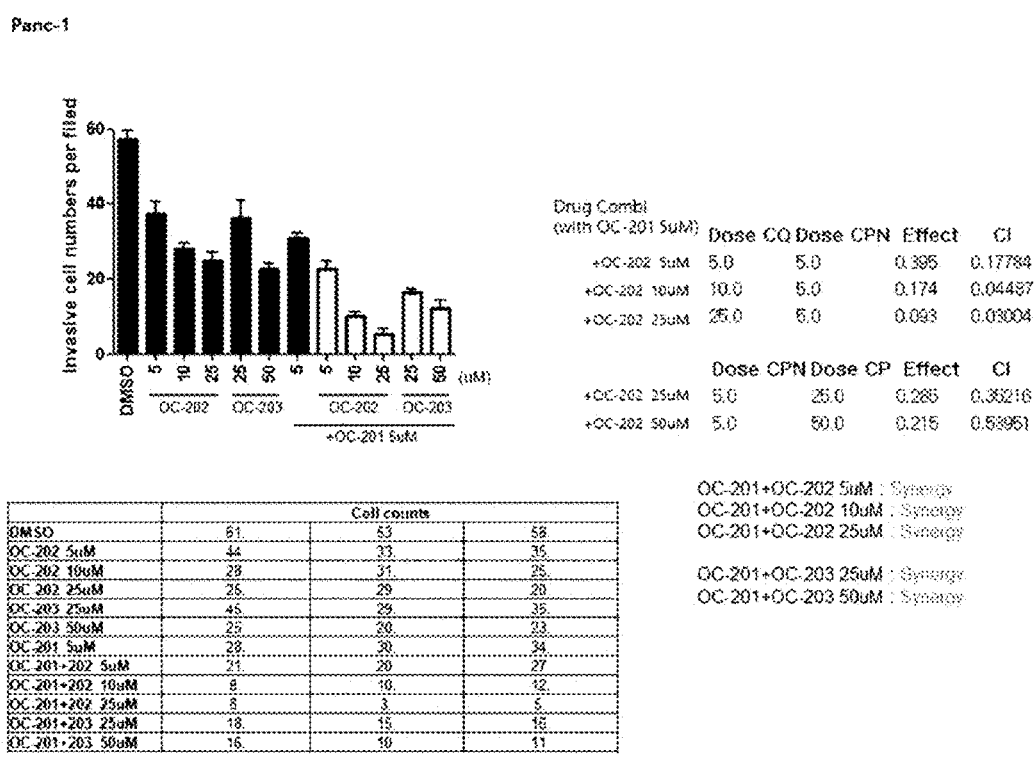

[Figure 44]
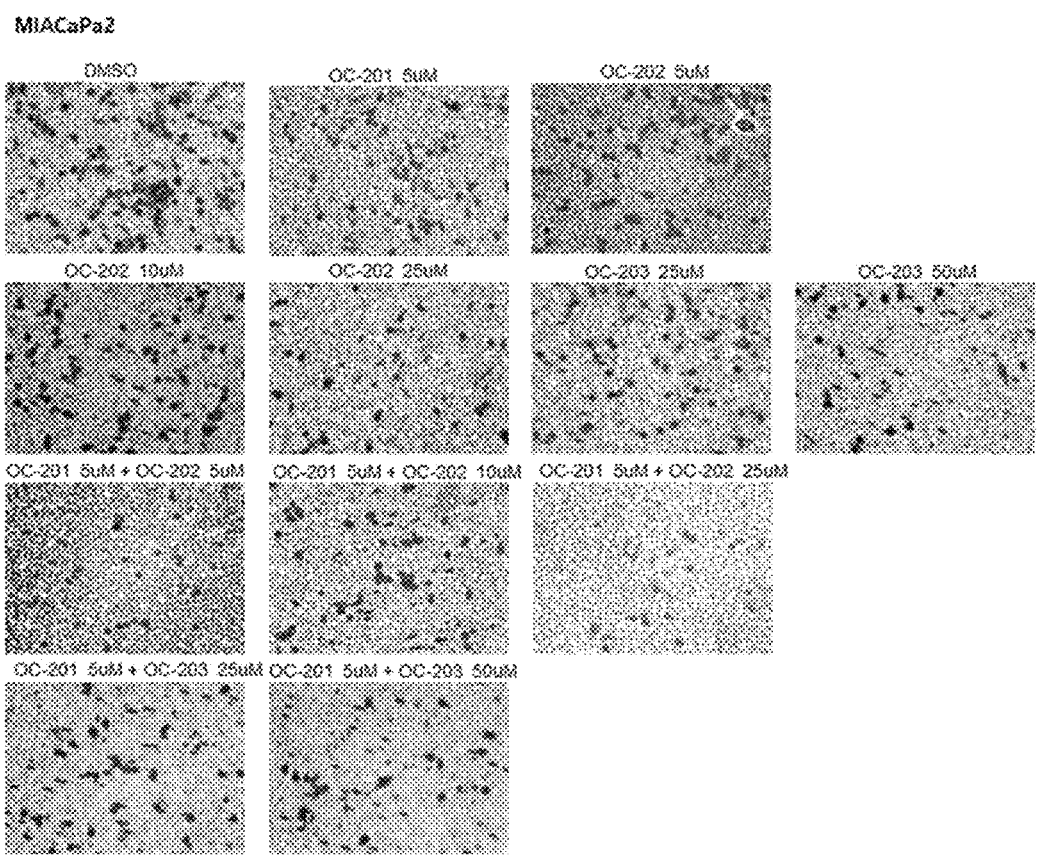

[Figure 45]
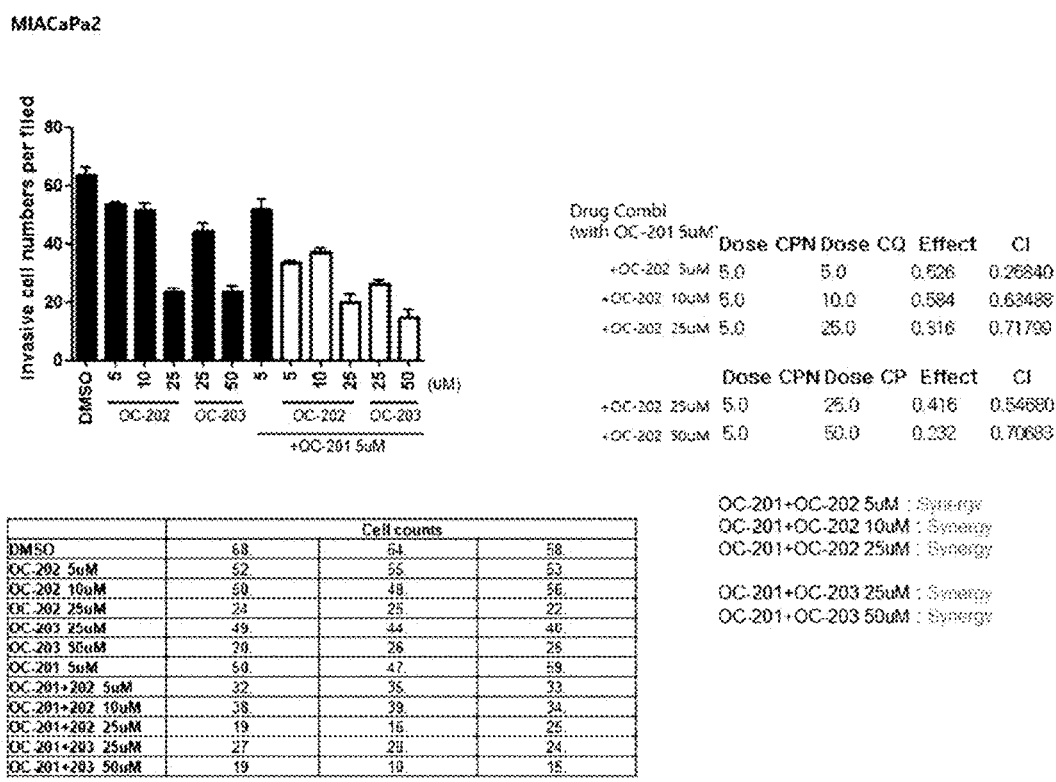

[Figure 46]
SNU1079
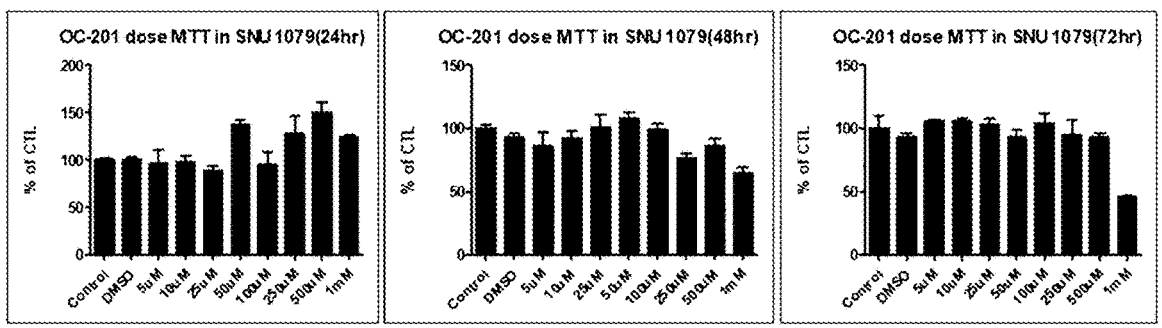
SNU308
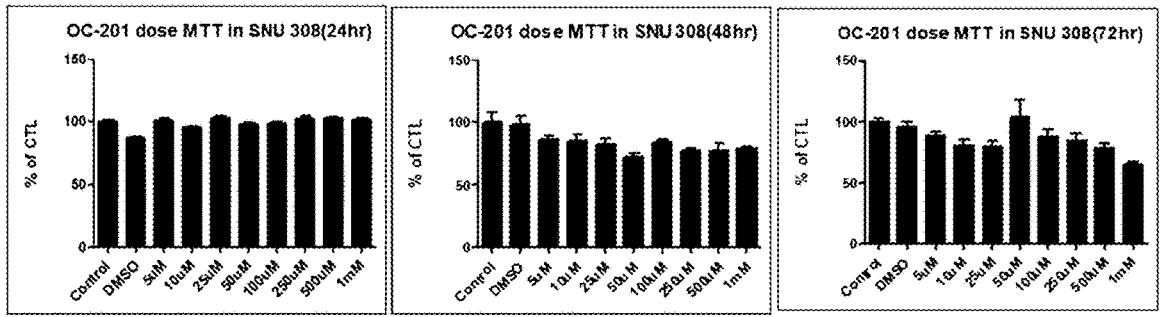

[Figure 47]
SNU1079
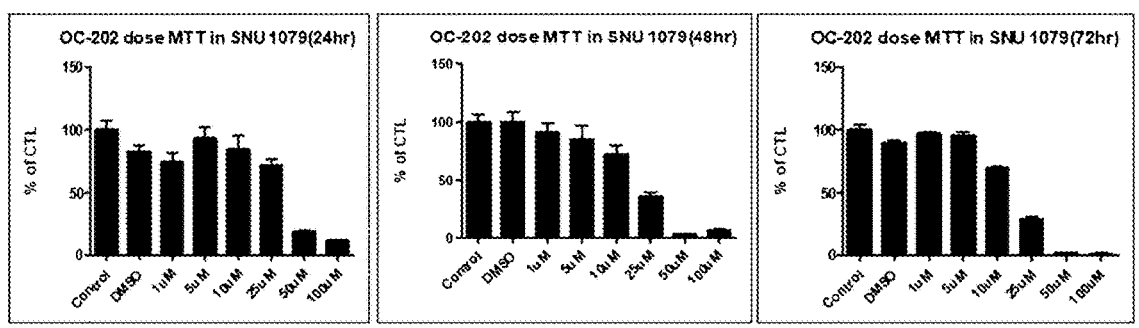
SNU308
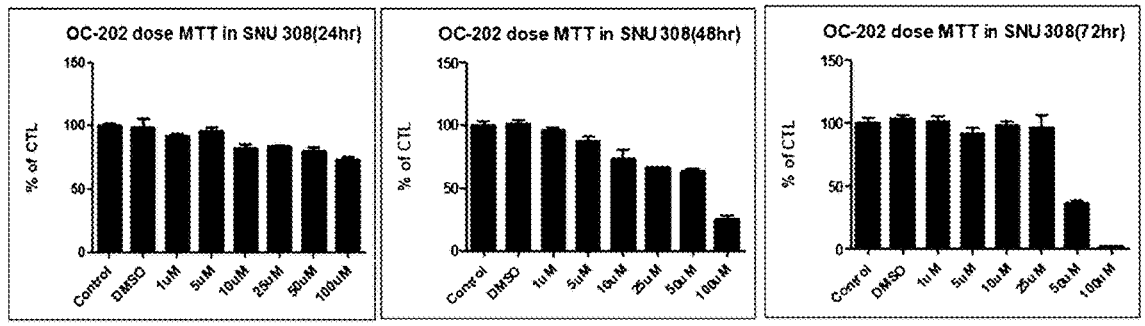

[Figure 48]
SNU1079
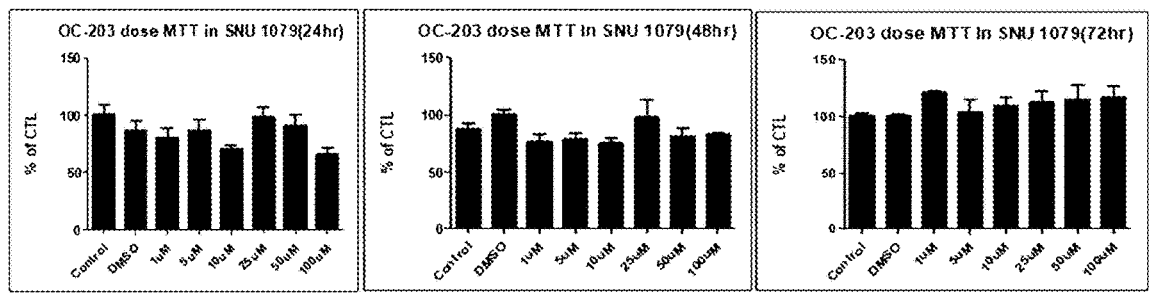
SNU308
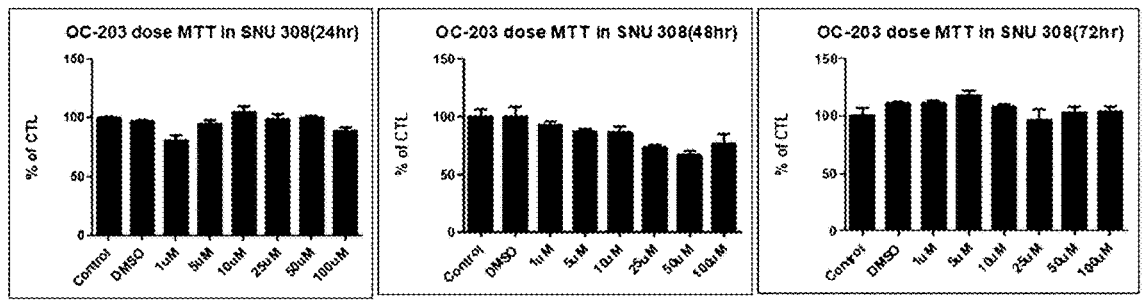

[Figure 49]
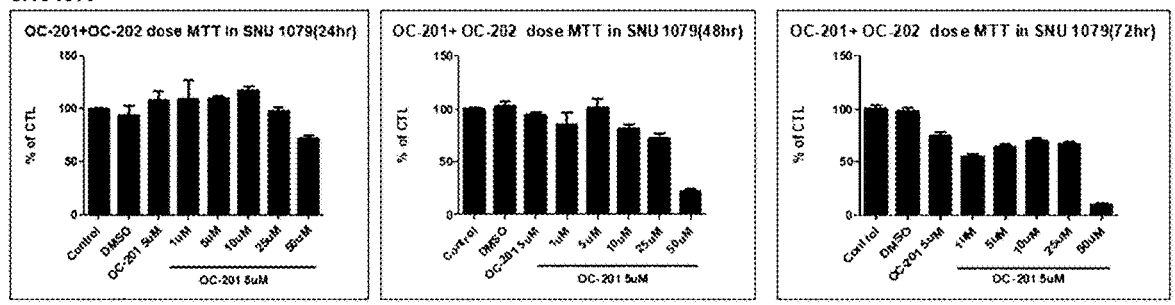
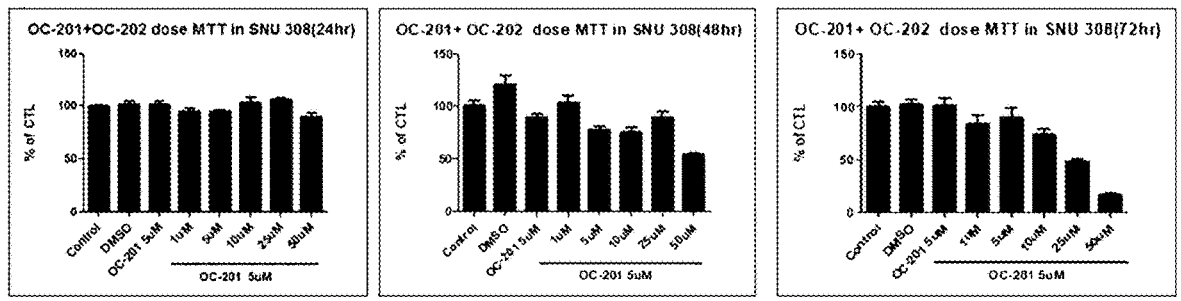

[Figure 50]
SNU1079
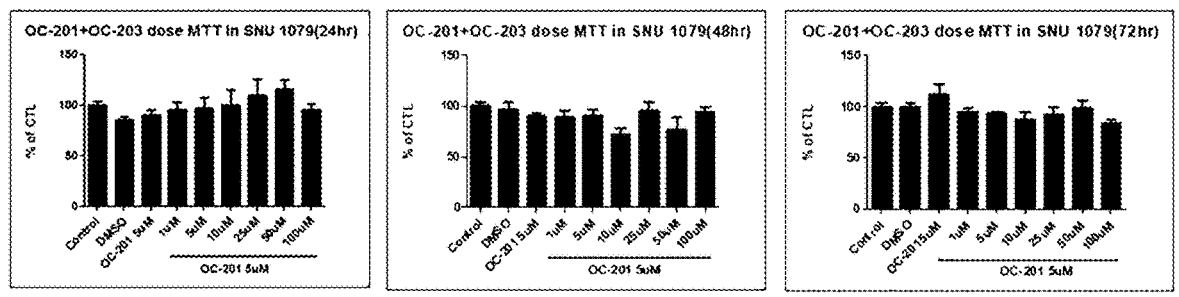
SNU308
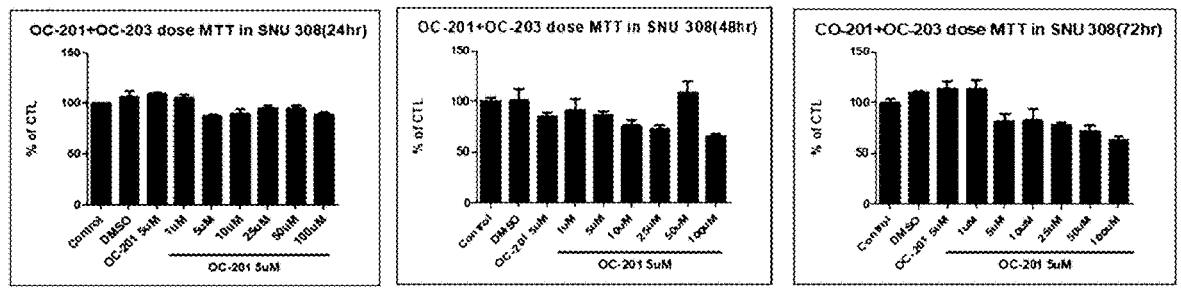

[Figure 51]
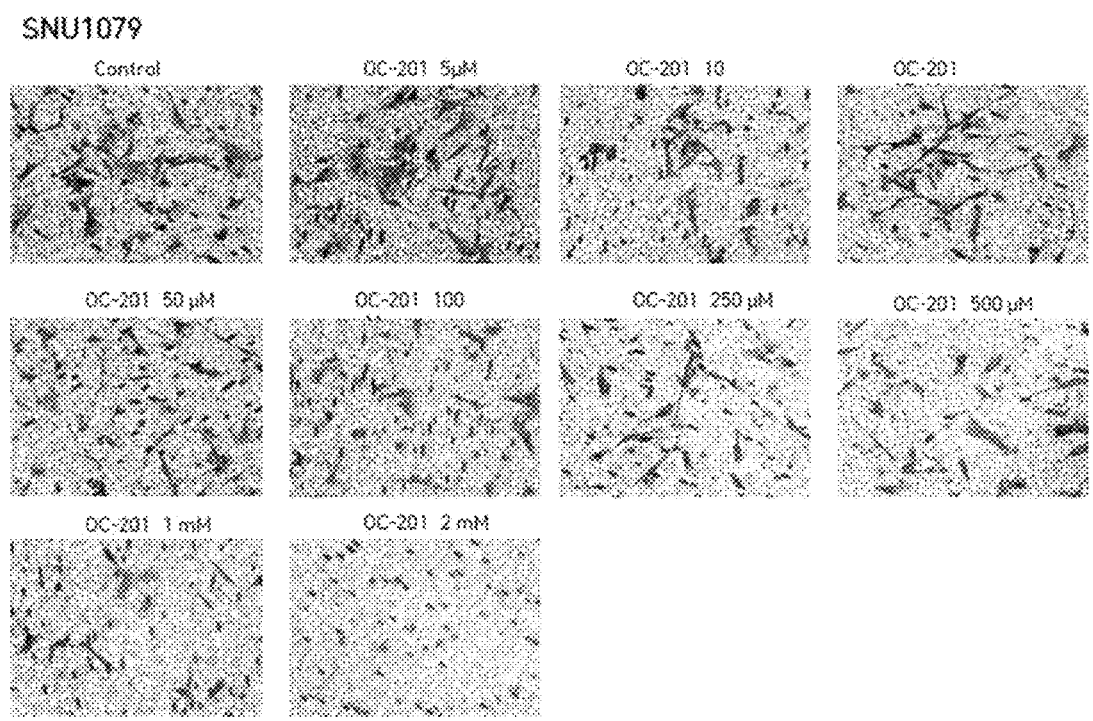

[Figure 52]
SNU1079
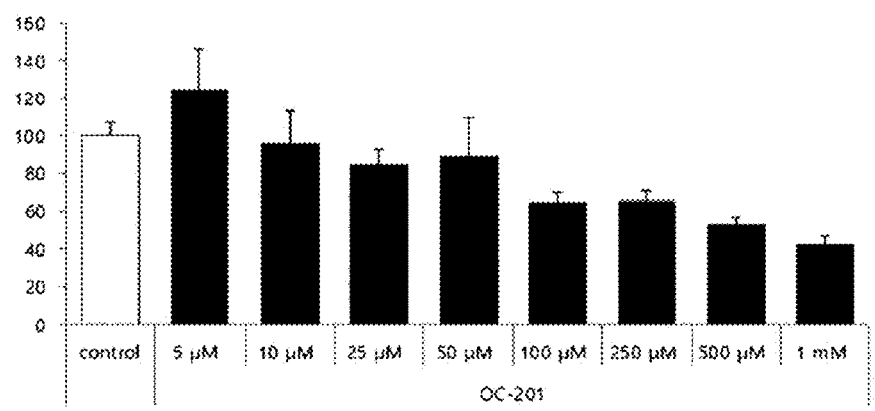

[Figure 53]
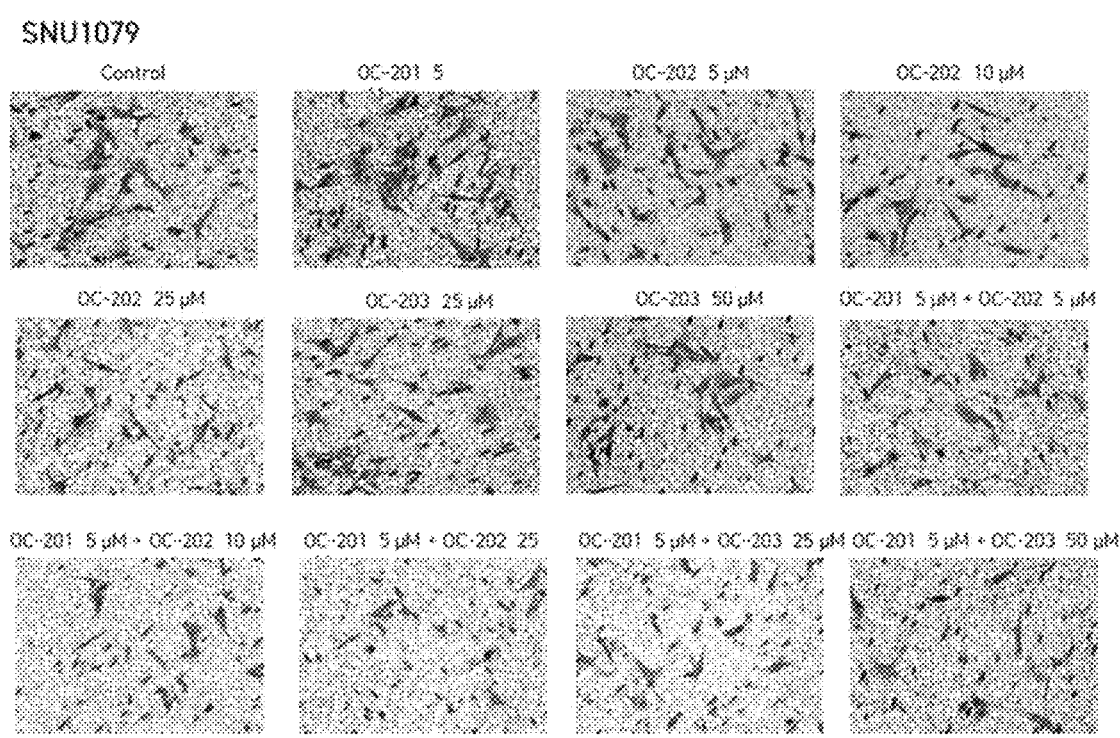

[Figure 54]
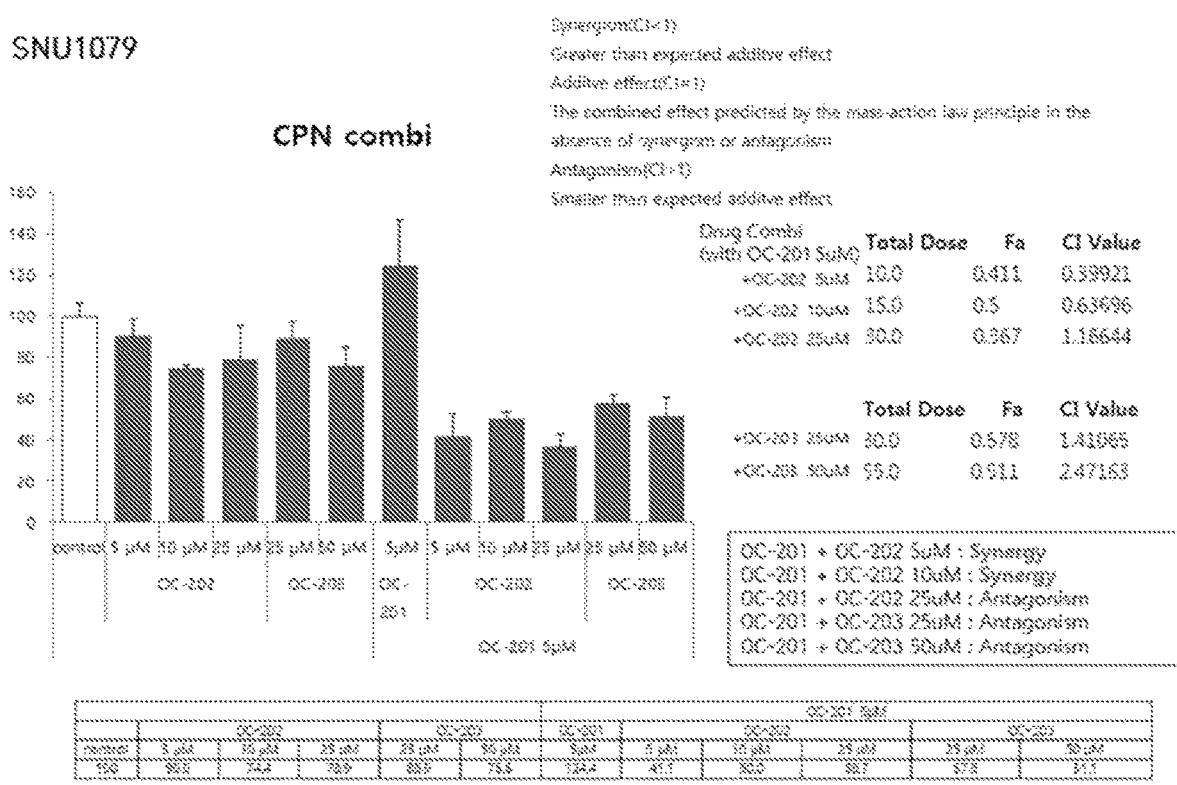

[Figure 55]
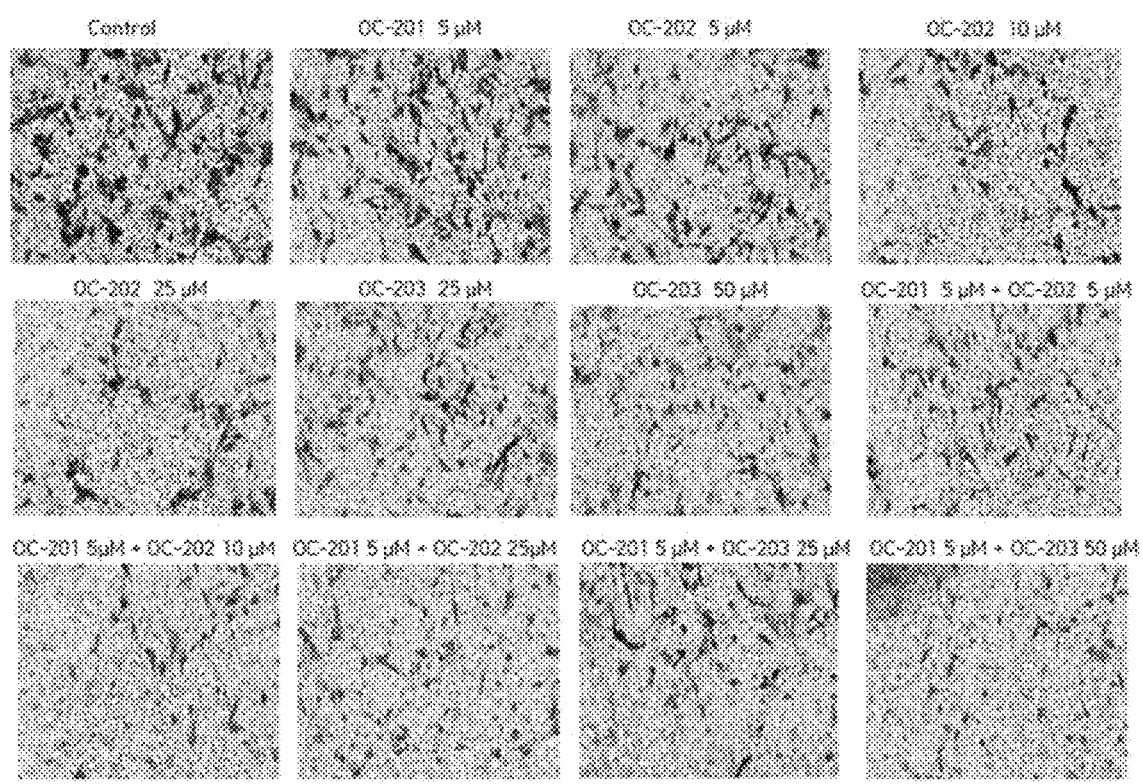

[Figure 56]
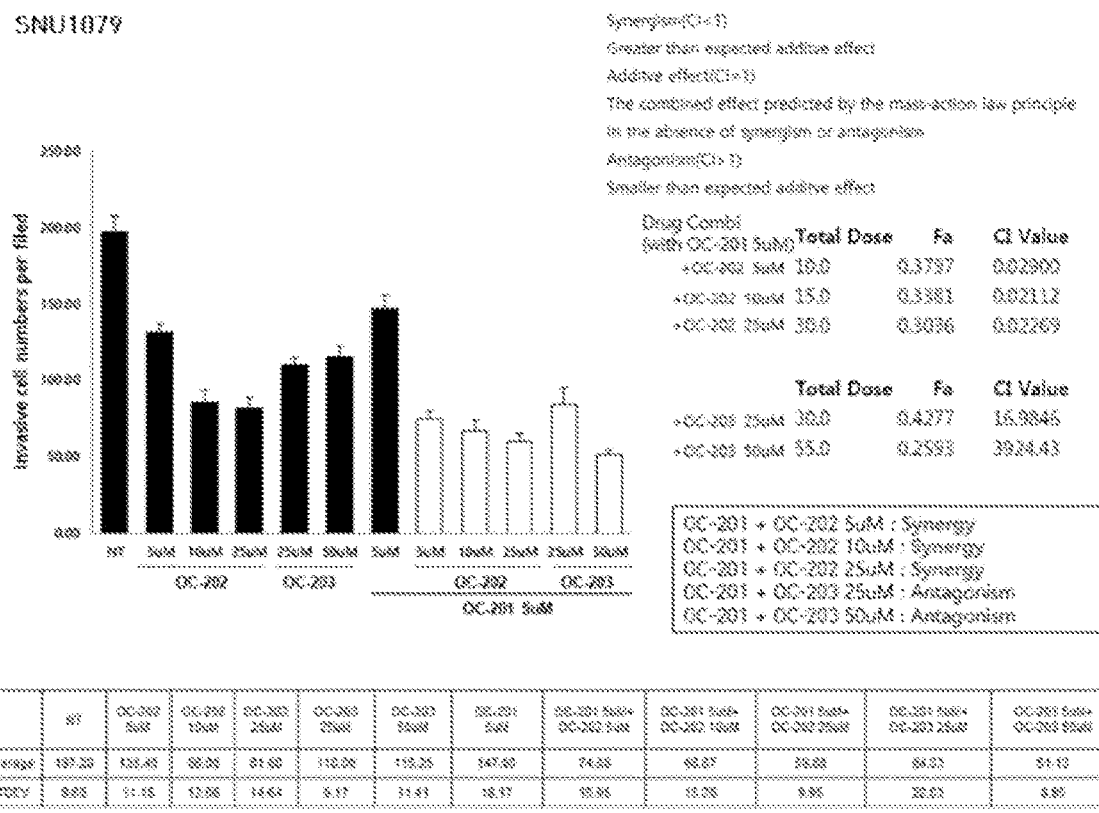

[Figure 57]
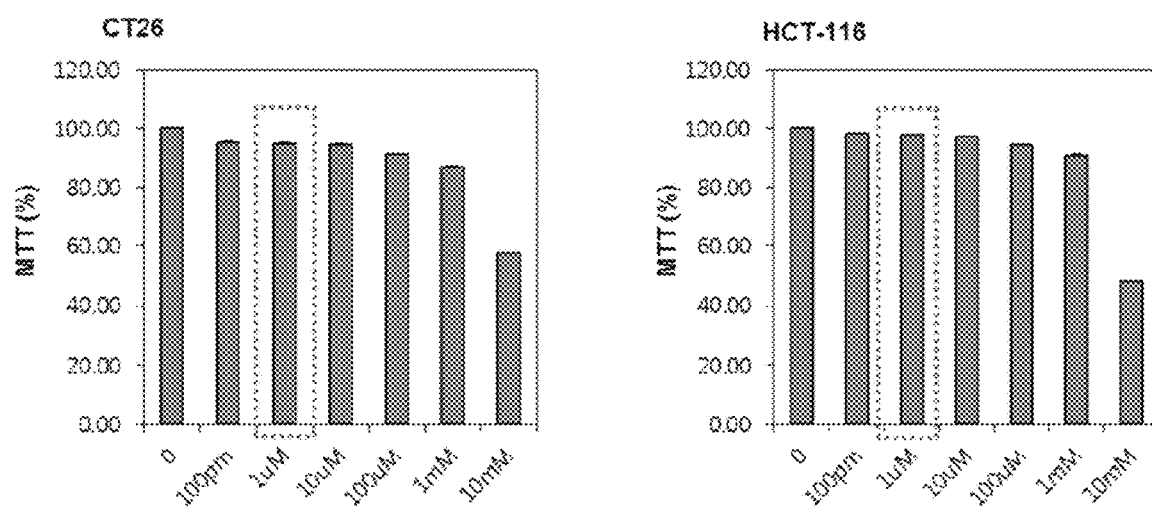

[Figure 58]
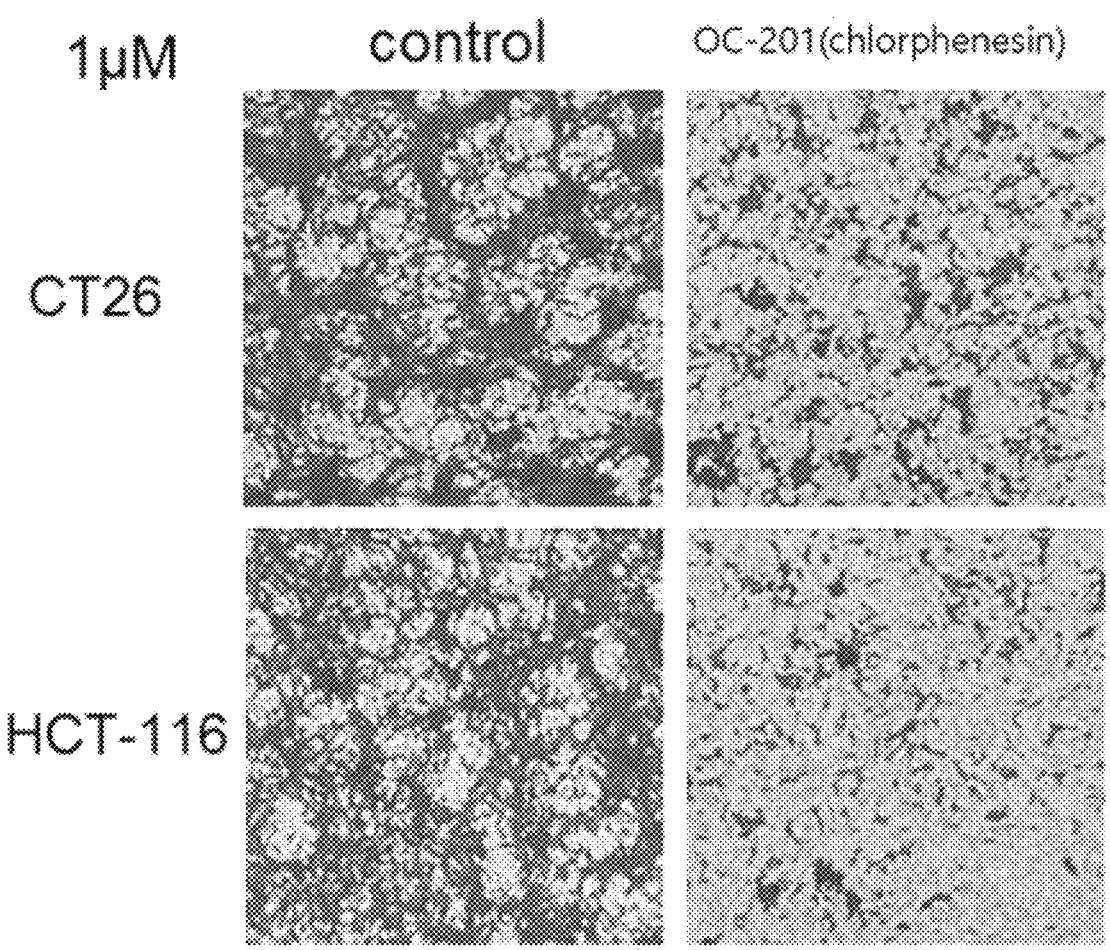

[Figure 59]
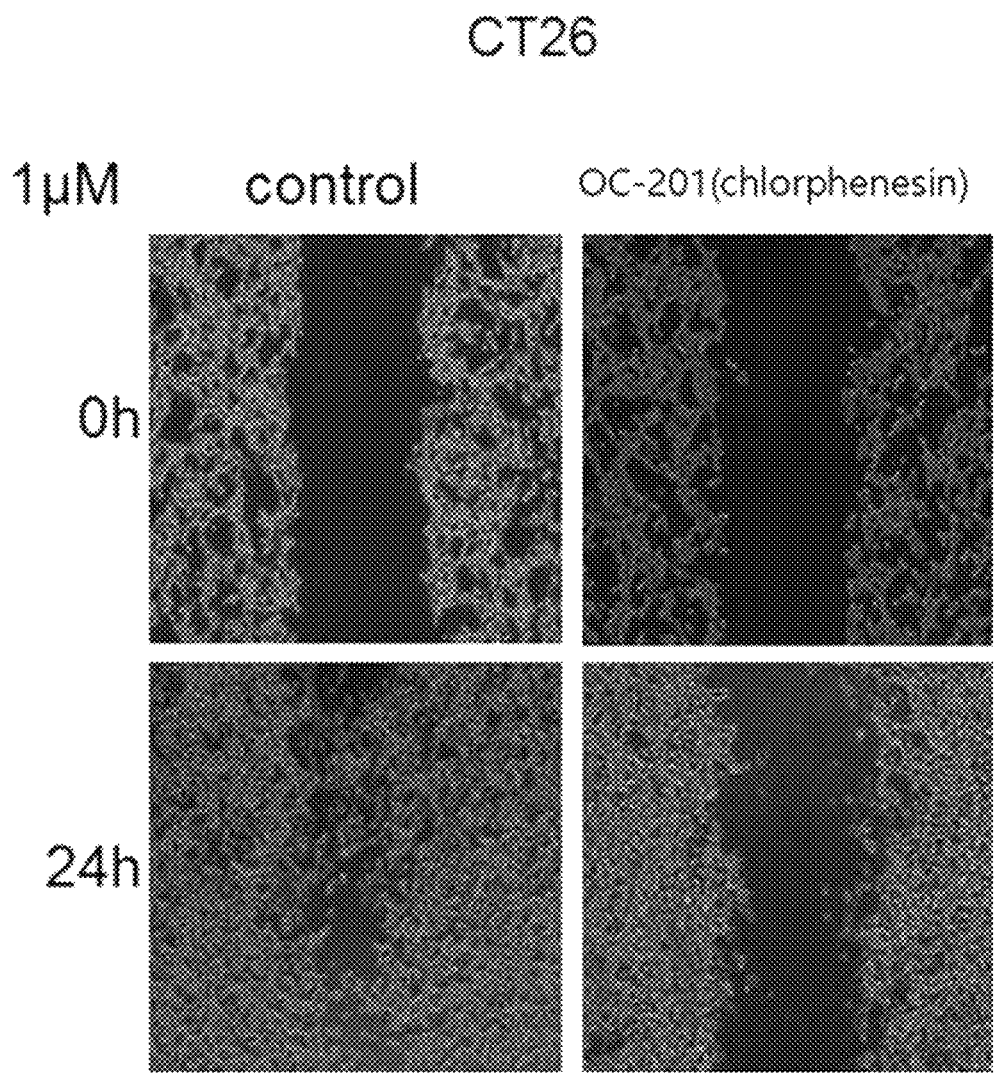

[Figure 60]
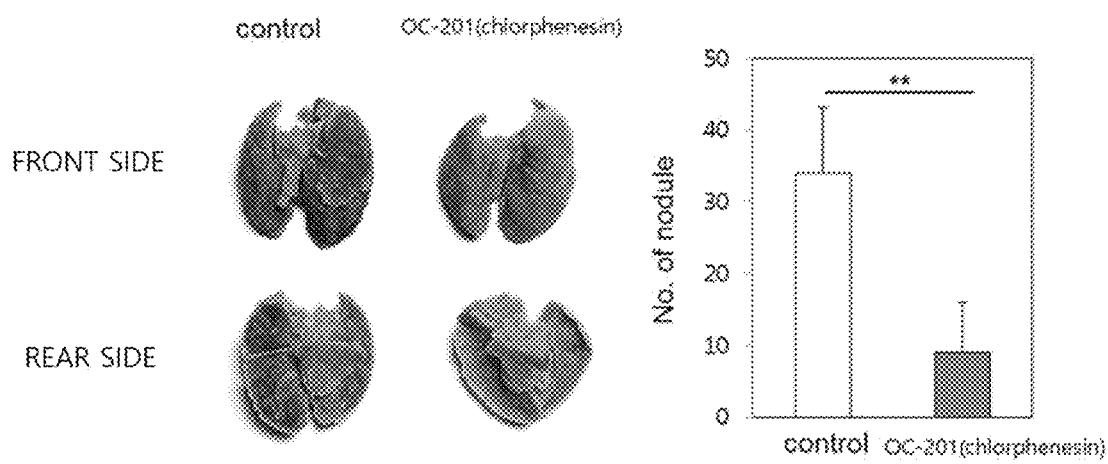

[Figure 61]
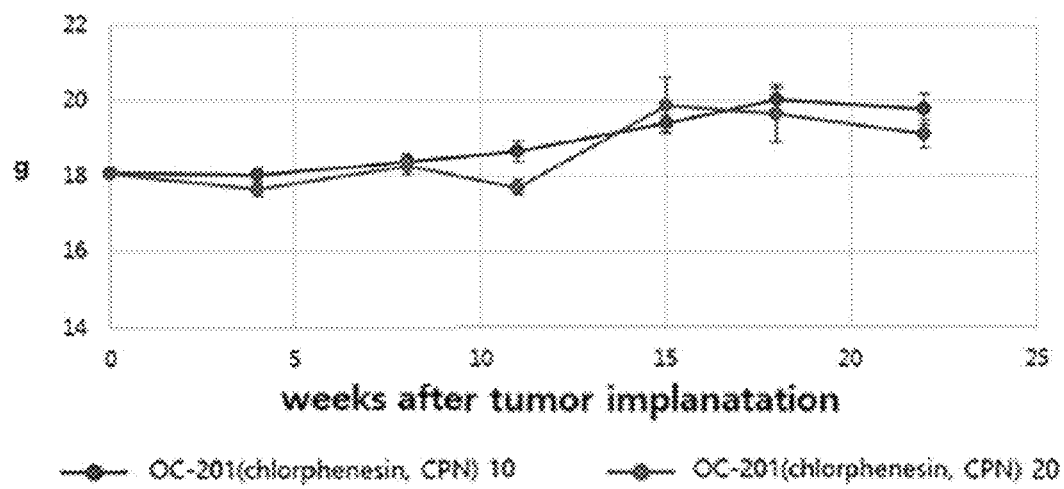
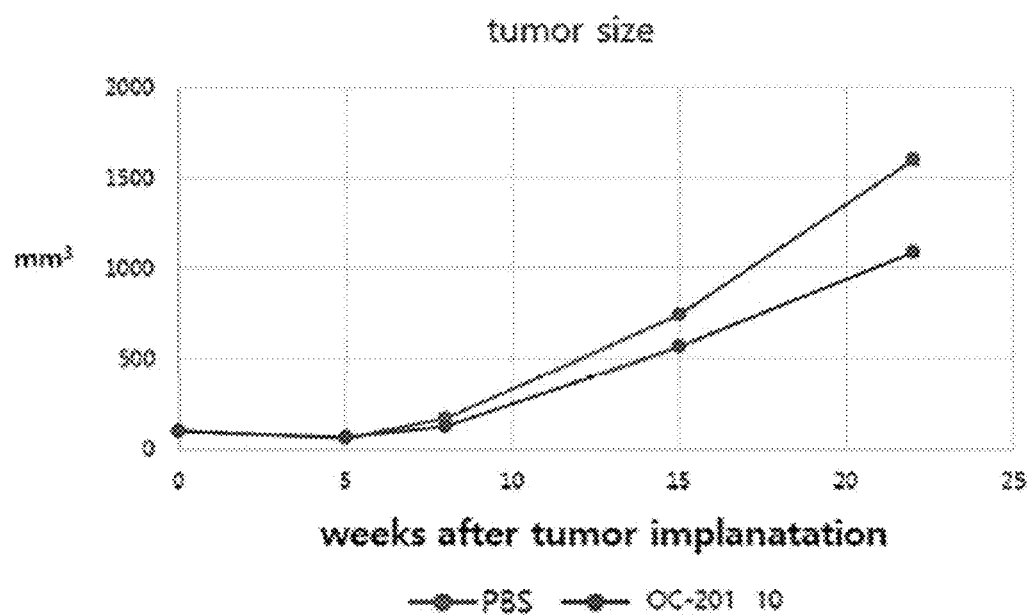

COMPOSITION FOR INHIBITING CANCER METASTASIS AND TREATING CANCER

CROSS REFERENCE TO RELATED APPLICATIONS

This application is a National Stage of International Application No. PCT/KR2018/001549, filed Feb. 6, 2018, claiming priority to Korean Patent Application No. 10-2017-0016587, filed Feb. 7, 2017 and KR 10-2018-0014306, filed Feb. 6, 2018, the entire disclosures of which are incorporated herein by reference.

TECHNICAL FIELD

The present invention relates to a composition for treating cancer and inhibiting cancer metastasis, and anticancer and metastasis inhibiting effects by treatment with chlorphenesin, chloroquine, or chloropyrazine alone or in combination thereof.

BACKGROUND ART

A cell is the smallest unit constituting a human body. The normal cells maintain constant cell numbers with their own regulating function such as cell growth, division, and death. If the cell is damaged from a certain cause, it is repaired to serve as a normal cell, or when the cell has not been recovered, it dies by itself. However, if a mutation occurs in normal cells due to several reasons, then this mutation results in immature cells that do not regulate the cell cycle. Accordingly, the cell will continue to divide, which is defined as cancer. In addition, the cancer cells have features that they invade and destroy surrounding tissues or organs, as well as spread to other parts of body. Cancer is the number one cause of death in Korea, and its death rate has been increasing every year. Though there has been a considerable progress in medical treatments in certain cancers, the five-year survival rate for all cancers has improved only about 10 percent for the past 20 years. Cancers or malignancies tend to spread and grow faster in an unregulated way, so it is extremely difficult to detect and treat them on time.

The large intestine (colon, large bowel) is a long tube-shaped digestive organ that connects the small intestine (ileum) to the rectum. Colorectal cancer happens when tumorous growths develop in the parts. The colorectal cancer is divided into colon and rectum cancers depending on the parts where the tumors growths are developed. The patients with colorectal cancer usually have symptoms such as a change in bowel habit, bloody stool or mucous stool, narrow stool, weight loss, abdominal pain, fatigue, inappetence, etc. Colorectal cancer is commonly spread to the liver or lung, and about more than 50 percent of patients experience cancer metastasis. The colorectal cancer is treated by surgery or radiotherapy or targeted chemotherapy or conventional chemotherapy. Cetuximab (Erbitux) injection is a represented targeted therapy for colorectal cancer. Cetuximab is a monoclonal antibody to target the epidermal growth factor receptors (EGFR), which specifically binds to with EGFR on the surface of colorectal cancer cells to suppress the overall proliferation of cancer cells by inhibiting a certain process in signal transduction causing the cancer cell growth.

Pancreatic cancer has the highest mortality rate of all major cancers. In the U. S, more than 40 thousand people are diagnosed with pancreatic cancer, and less than 5 percent of them is alive five years or more after diagnosis. The low survival rate is attributable to the fact that most pancreatic cancers are often difficult to diagnose until the cancers have spread to surrounding tissues or organs. As the patients have no symptom at an early stage, and the symptoms are non-specific and varied at a terminal stage, it makes it harder to early diagnose. And, the treatment options for the pancreatic cancer are limited. At an early stage, the pancreatic cancer is treated with surgery and radiation therapy. However, the options are not effective for advanced or recurrent pancreatic cancer. Gemcitabine that is given by infusion through a vein (intravenously, by IV) is effective once a day to treat pancreatic cancer, which was approved by FDA in U. S. in 1998. Gemcitabine is most commonly used in the treatment of pancreatic cancer, which is combined with other medication such as oxalate or 5-FU (5-fluorouracil). But it has had very little effect on the significant increase in the survival rate of pancreatic cancer patients. For the standard treatment of the conventional chemotherapy, Gemcitabine is given alone (single agent) or can be given together (combination chemotherapy) with erlotinib, EGFR tyrosine kinase inhibitor. Alternative options are multidrug combination of 5-fluorouracil, leucovorin, irinotecan and oxaliplatin (it is also known as FOLFIRINOX protocol), or the combination of nanoparticle albumin-bound (nab)-paclitaxel plus gemcitabine. The latter showed a superior effect to the monotherapy with gemcitabine (Von Hoff et al., 2013; S3-Leitlinie Exokrines Pankreaskarzinom, 2013). The FDA approved erlotinib, a kinase inhibitor, for the combination therapy with gemcitabine for the patient with the advanced pancreatic cancer who has had no chemotherapy. However, the median overall survival with erlotinib and gemcitabine improved less than 4 weeks (Moore et al., J. Clin. Oncol., 25(15):1960-6 (2007)).

The bile duct is a tube-like structure to carry bile secreted from the liver to the duodenum. In the liver, it becomes thicker by joining bile duct as if each branch of trees is formed of the branches of one. Left and right bile ducts combined to form a common bile duct. The two types of bile duct in the liver are intrahepatic bile ducts within the liver and extrahepatic bile ducts that carry bile outside of the liver, connecting to the duodenum. The gallbladder located at extrahepatic bile ducts temporarily stores and concentrates bile from the liver, and the bile duct consists of bile duct and gallbladder. As a system of vessels that directs the secretions from the liver, the bile duct connects to duodenum while becoming thicker and thicker, like branches. The gallbladder is a location for primary stasis of bile. Biliary tract cancer is a general term for biliary tract cancer and gallbladder cancer, which arises from the epithelial cell of the intrahepatic bile duct. At the time of diagnosis, 70 to 80 percent of patients with the cancer are an advanced cancer. As only 30 to 40 percent of them are treated by surgery, and the five-year survival rate for the cancer is around 7 percent, it is one of the intractable cancers. Although diverse kinds of anticancer drugs have been developed, there is very little cancer to be cured only with the drug. This is because the cancer cells do not react with the anticancer drugs, or the drug is effective to shrink the tumor cells at the early stage of the treatment but lost its effectiveness due to drug-resistant problems during treatment or after treatment. Thus, for the treatment that is effective against cancers, the anticancer drug should overcome drug resistance problems such as resistance of cancer cell to anticancer drug. In the case of biliary tract cancer, such problem frequently occurs at the early period of treatment. Thus, the response rate of the anticancer drug is only 15 percent, and the recurrence rate after surgery is 85 percent. This clearly shows that there is no effective anticancer drug before and after surgery.

Malignancies arise from an organ (such as lung, liver, kidney, stomach, colon, rectum, etc.) and spread from the place where the cancer began to another part of the body. Metastasis means that malignancies spread from the place where the cancer began to another part of the body, which is accompanied with malignant tumor progression. As the malignant tumor cell is grown and the cancer is progressed, it acquires a new genetic character that is necessary for metastasis, invades into blood vessels and lymphatic glands, circulates through them, settles down in another organ, and grows.

Currently, surgery, radiation therapy, and chemotherapy are used for cancer therapy. Among them, chemotherapy is to treat cancer with anticancer drugs. Recently, about 60 kinds of anticancer drugs are used. As much known about the cancer development and cancer cell characteristics, the new anticancer agents have actively developed. However, because the current therapy has focused on death or removal of the cancer cells, there is a lack of research on medications to prevent growth and metastasis of cancer, which is the immediate cause of an increase in the survival rate of the patients with cancers. Therefore, to enhance cancer treatment rate and the survival rate of patients, there is a great need for developing a novel drug with an anticancer activity and inhibitory effects of cancer cell growth and metastasis together.

DISCLOSURE

Technical Problem

The present inventors have confirmed that chlorphenesin, chloroquine, or chloropyrazine has anticancer effects and inhibitory effects of proliferation and metastasis of cancer cells, and their combination has a synergy effect, thereby completing the present invention.

Technical Solution

In order to archive the objects as described above, the present invention provides the pharmaceutical composition for preventing or treating cancer, the composition including at least one selected from the group consisting of chlorphenesin, chloroquine and chloropyrazine or a pharmaceutically acceptable salt thereof as an active ingredient.

Further, the present invention provides the pharmaceutical composition for inhibiting cancer proliferation and metastasis, the composition including at least one selected from the group consisting of chlorphenesin, chloroquine and chloropyrazine, or a pharmaceutically acceptable salt thereof as an active ingredient.

Further, the present invention provides the cancer adjuvant including at least one selected from the group consisting of chlorphenesin, chloroquine and chloropyrazine, or a pharmaceutically acceptable salt thereof as an active ingredient.

Further, the present invention provides a food composition for preventing or ameliorating cancer, the composition including at least one selected from the group consisting of chlorphenesin, chloroquine and chloropyrazine, or a pharmaceutically acceptable salt thereof.

Advantageous Effects

The present invention relates to an anticancer composition for inhibiting the proliferation and metastasis of cancer cells, and it is possible to effectively inhibit proliferation and metastasis by administering chlorphenesin, chloroquine or chloropyrazine alone or in combination.

DESCRIPTION OF DRAWINGS

FIG. 1 is a graph showing cell survival rates of colorectal cancer cell lines CT26, HCT116 and SW480 by chlorphenesin (OC-201).

FIG. 2 is a graph showing cell survival rates of colorectal cancer cell lines CT26, HCT116 and SW480 by chloroquine (OC-202).

FIG. 3 is a graph showing cell survival rates of colorectal cancer cell lines CT26, HCT116 and SW480 by chloropyrazine (OC-203).

FIG. 4 is a graph showing cell survival rates of colorectal cancer cell lines CT26, HCT116 and SW480 by the treatment with chlorphenesin and chloroquine in combination.

FIG. 5 is a graph showing cell survival rates of colorectal cancer cell lines CT26, HCT116 and SW480 by the treatment with chlorphenesin and chloropyrazine in combination.

FIG. 6 is a view showing the degree of migration of SW480 cells according to chlorphenesin concentration.

FIG. 7 is a graph showing the degree of migration of SW480 cells according to chlorphenesin concentration.

FIG. 8 is a view showing the degree of migration of HCT116 cells according to chlorphenesin concentration.

FIG. 9 is a graph showing the degree of migration of HCT116 cells according to chlorphenesin concentration.

FIG. 10 is a view showing the degree of migration of CT26 cells according to chlorphenesin concentration.

FIG. 11 is a graph showing the degree of migration of CT26 cells according to chlorphenesin concentration.

FIG. 12 is a view showing the degree of migration of SW480 cells according to the treatment with chlorphenesin, chloroquine or chloropyrazine alone or in combination.

FIG. 13 is a graph showing the degree of migration of SW480 cells according to the treatment with chlorphenesin, chloroquine or chloropyrazine alone or in combination.

FIG. 14 is a view showing the degree of migration of HCT116 cells according to the treatment with chlorphenesin, chloroquine or chloropyrazine alone or in combination.

FIG. 15 is a graph showing the degree of migration of HCT116 cells according to the treatment with chlorphenesin, chloroquine or chloropyrazine alone or in combination.

FIG. 16 is a view showing the degree of migration of CT26 cells according to the treatment with chlorphenesin, chloroquine or chloropyrazine alone or in combination.

FIG. 17 is a graph showing the degree of migration of CT26 cells according to the treatment with chlorphenesin, chloroquine or chloropyrazine alone or in combination.

FIG. 18 is a view showing a synergy effect on the inhibition of migration of SW480 cells according to the concentration of the treatment with chlorphenesin and chloroquine or chloropyrazine in combination.

FIG. 19 is a view showing a synergy effect on the inhibition of migration of HCT116 cells according to the concentration of the treatment with chlorphenesin and chloroquine or chloropyrazine in combination.

FIG. 20 is a view showing a synergy effect on the inhibition of migration of CT26 cells according to the concentration of the treatment with chlorphenesin and chloroquine or chloropyrazine in combination.

FIG. 21 is a view for confirming the effect on the inhibition of HCT116 cells migration by treating with chlorphenesin alone through a wound healing assay.

FIG. 22 is a view for confirming the effect on the inhibition of HCT116 cells migration by treating with chlorphenesin alone through a wound healing assay.

FIG. 23 is a graph showing results of a wound healing assay of HCT116 by treating with chlorphenesin alone.

FIG. 24 is a view for confirming the effect on the inhibition of HCT116 cells migration by treating with each of chloroquine (OC-202) and chloropyrazine (OC-203) alone through a wound healing assay.

FIG. 25 is a view for confirming the effect on the inhibition of HCT116 cells migration by treating with chlorphenesin and chloroquine or chloropyrazine in combination through a wound healing assay.

FIG. 26 is a graph showing results of a wound healing assay of HCT116 cells by treating with chloroquine or chloropyrazine alone or chlorphenesin and chloroquine or chloropyrazine in combination.

FIG. 27 is a view showing the results of analysis of colony formation of HCT116 cells according to chlorphenesin treatment concentration.

FIG. 28 is a view showing the analysis results of colony formation of HCT116 cells according to chlorphenesin, chloroquine or chloropyrazine single treatment concentration or chlorphenesin and chloroquine or chloropyrazine in combination treatment concentration.

FIG. 29 is a view showing the analysis results of colony formation of CT26 cells according to chlorphenesin, chloroquine or chloropyrazine single treatment concentration or chlorphenesin and chloroquine or chloropyrazine in combination treatment concentration.

FIG. 30 is a graph showing cell survival rates of pancreatic cancer cell lines Aspc-1, MIAPaCA2 and Panc-1 according to chlorphenesin treatment concentration.

FIG. 31 is a graph showing cell survival rates of pancreatic cancer cell lines Aspc-1, MIAPaCA2 and Panc-1 according to chloroquine treatment concentration.

FIG. 32 is a graph showing cell survival rates of pancreatic cancer cell lines Aspc-1, MIAPaCA2 and Panc-1 according to chloropyrazine treatment concentration.

FIG. 33 is a graph showing cell survival rates of pancreatic cancer cell lines Aspc-1, MIAPaCA2 and Panc-1 according to the concentration of combination treatment of 5 µM of chlorphenesin and 1 µM to 50 µM of chloroquine.

FIG. 34 is a graph showing cell survival rates of pancreatic cancer cell lines Aspc-1, MIAPaCA2 and Panc-1 according to the concentration of combination treatment of 0.5 µM of chloroquine and 1 µM to 50 µM of chlorphenesin.

FIG. 35 is a graph showing cell survival rates of pancreatic cancer cell lines Aspc-1, MIAPaCA2 and Panc-1 according to the concentration of combination treatment of 1 µM of chloroquine and 1 µM to 50 µM of chlorphenesin.

FIG. 36 is a graph showing cell survival rates of pancreatic cancer cell lines Aspc-1, MIAPaCA2 and Panc-1 according to the concentration of combination treatment of 5 µM of chloroquine and 1 µM to 50 µM of chlorphenesin.

FIG. 37 is a graph showing cell survival rates of pancreatic cancer cell lines Aspc-1, MIAPaCA2 and Panc-1 according to the concentration of combination treatment of 5 µM of chlorphenesin and 1 µM to 25 µM of chloropyrazine.

FIG. 38 is a view showing the degree of migration of pancreatic cancer cell line Panc-1 according to the treatment with chlorphenesin, chloroquine or chloropyrazine alone or chlorphenesin and chloroquine or chloropyrazine in combination.

FIG. 39 is a view showing a synergy effect on the inhibition of migration of cells according to the combination treatment concentration in pancreatic cancer cell line Panc-1 treated with chlorphenesin and chloroquine or chloropyrazine in combination.

FIG. 40 is a view showing the degree of migration of pancreatic cancer cell line Aspc-1 according to the treatment with chlorphenesin, chloroquine or chloropyrazine alone or chlorphenesin and chloroquine or chloropyrazine in combination.

FIG. 41 is a view showing a synergy effect on the inhibition of migration of cells according to the combination treatment concentration in pancreatic cancer cell line Aspc-1 treated with chlorphenesin and chloroquine or chloropyrazine in combination.

FIG. 42 is a view showing the invasion assay results of the pancreatic cancer cell line Panc-1 treated with chlorphenesin, chloroquine or chloropyrazine alone or chlorphenesin and chloroquine or chloropyrazine in combination.

FIG. 43 is a view showing a synergy effect on the inhibition of invasion of cells according to the combination treatment concentration in pancreatic cancer cell line Panc-1 treated with chlorphenesin and chloroquine or chloropyrazine in combination.

FIG. 44 is a view showing the invasion assay results of pancreatic cancer cell line MIACaPa2 according to the treatment with chlorphenesin, chloroquine or chloropyrazine alone or chlorphenesin and chloroquine or chloropyrazine in combination.

FIG. 45 is a view showing a synergy effect on the inhibition of invasion of cells according to the combination treatment concentration in pancreatic cancer cell line MIACaPa2 treated with chlorphenesin and chloroquine or chloropyrazine in combination.

FIG. 46 is a graph showing cell survival rates of biliary tract cancer cell SNU1079 and SNU308 according to chlorphenesin concentration.

FIG. 47 is a graph showing cell survival rates of biliary tract cancer cell SNU1079 and SNU308 according to chloroquine concentration.

FIG. 48 is a graph showing cell survival rates of biliary tract cancer cell SNU1079 and SNU308 according to chloropyrazine concentration.

FIG. 49 is a graph showing cell survival rates of biliary tract cancer cells SNU1079 and SNU308 according to the combination treatment concentration of chlorphenesin and chloroquine.

FIG. 50 is a graph showing cell survival rates of biliary tract cancer cells SNU1079 and SNU308 according to the combination treatment concentration of chlorphenesin and chloropyrazine.

FIG. 51 is a view showing the degree of the inhibition of migration of biliary tract cancer cell SNU1079 according to the chlorphenesin concentration.

FIG. 52 is a graph showing the degree of the inhibition of migration of biliary tract cancer cell SNU1079 according to the chlorphenesin concentration.

FIG. 53 is a view showing the degree of the inhibition of migration of biliary tract cancer cell SNU1079 treated with chlorphenesin, chloroquine and chloropyrazine alone or chlorphenesin and chloroquine or chloropyrazine in combination.

FIG. 54 is a view showing a synergy effect on the inhibition of migration of cells according to the combination treatment concentration in biliary tract cancer cell line SNU1079 treated with chlorphenesin and chloroquine or chloropyrazine in combination.

FIG. 55 is a view showing an effect on the inhibition of invasion of biliary tract cancer cell SNU1079 treated with chlorphenesin, chloroquine and chloropyrazine alone or chlorphenesin and chloroquine or chloropyrazine in combination.

FIG. 56 is a view showing a synergy effect on the inhibition of invasion of cells according to the combination treatment concentration in biliary tract cancer cell line SNU1079 treated with chlorphenesin and chloroquine or chloropyrazine in combination.

FIG. 57 is a graph showing the evaluation result of the cytotoxicity of chlorphenesin.

FIG. 58 is a staining image of CT26 cells and HCR116 cells treated with or untreated with chlorphenesin.

FIG. 59 is a staining image of a sectional layer of CT26 cells treated with or untreated with chlorphenesin.

FIG. 60 is a graph showing the image of the lungs and the number of nodules occurring in the lungs collected in the cancer metastatic animal model.

FIG. 61 is a graph showing the measurement results of body weight and tumor size in the cancer metastasis animal model.

MODES OF THE INVENTION

Hereinafter, the present invention is described in detail with reference to the accompanying drawings. However, the following Examples are provided by way of illustration of the present invention. When it is determined that the specific description of known techniques or configuration well known to those skilled in the art unnecessarily obscures the subject matter of the present invention, the description may be excluded, and the present invention is not limited thereto. The present invention allows various modifications and applications within the description of the appended claims and the equivalents interpreted therefrom.

Further, terminologies used herein are terms used to properly represent preferred embodiments of the present invention. It may vary depending on the intent of users or operators, or custom in the art to which the present invention belongs. Accordingly, the definitions of these terms should be based on the contents throughout this specification. In the specification, when a part is referred to as "comprising" a component, it means that it may further include other components without excluding other components unless specifically described otherwise.

In an aspect, the present invention relates to the pharmaceutical composition for preventing or treating cancer, in which the composition includes at least one selected from the group consisting of chlorphenesin, chloroquine and chloropyrazine or a pharmaceutically acceptable salt thereof as an active ingredient.

In one embodiment, chlorphenesin may be represented by the following Chemical Formula 1, chloroquine may be represented by the following Chemical Formula 2, and chloropyrazine may be represented by the following Chemical Formula 3:

[Chemical Formula 1]

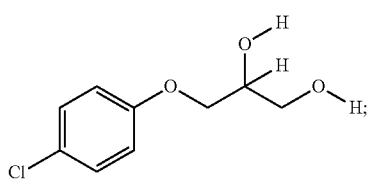

[Chemical Formula 2]

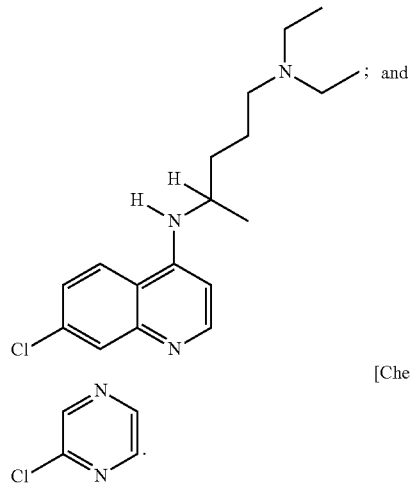

; and

[Chemical Formula 3]

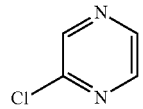.

In one embodiment, the chlorphenesin may be a chlorphenesin carbamate represented by the following Chemical Formula 4:

[Chemical Formula 4]

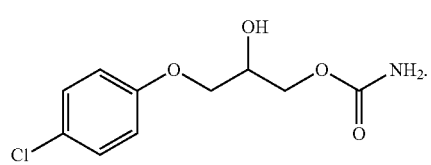

The chlorphenesin carbamate of the present invention is mainly used as a muscle relaxant and is known to have effects of sedation and anxiety relief and antifungal and antibacterial effects.

In one embodiment, the pharmaceutical composition of the present invention may include chlorphenesin and chloroquine, chlorphenesin and chloropyrazine, chloroquine and chloropyrazine, or chlorphenesin, chloroquine and chlorphenesin or a pharmaceutically acceptable salt thereof as an active ingredient. Chlorphenesin and chloroquine or chlorphenesin and chloropyrazine are more preferably included because they have a synergy anticancer effect.

In one embodiment, the pharmaceutical composition of the present invention may include 5 to 500 μM chlorphenesin, 0.5 to 25 μM chloroquine, or 1 to 100 μM chloropyrazine. The pharmaceutical composition may include 5 μM chlorphenesin (fixed concentration) and 0.5 to 25 μM chloroquine when chlorphenesin and chloroquine are included in combination. The pharmaceutical composition may include 5 μM chlorphenesin (fixed concentration) and 25 to 50 μM chloropyrazine when chlorphenesin and chloropyrazine are included in combination. In an example of the present invention, chlorphenesin, chloroquine and/or chloropyrazine of the present invention inhibits the migration and invasion of cancer cells without significant cytotoxicity in the above-described range of concentration in cell experiments.

In one embodiment, the cancer may be at least one selected from the group consisting of brain tumor, melanoma, myeloma, non-small cell lung cancer, oral cancer, liver cancer, gastric cancer, colon cancer, breast cancer, lung cancer, bone cancer, pancreatic cancer, skin cancer, head or neck cancer, cervical cancer, ovarian cancer, colorectal cancer, small intestine cancer, rectal cancer, fallopian tube cancer, anal cancer, endometrial carcinoma, vaginal carcinoma, vulvar carcinoma, Hodgkin's disease, esophageal cancer, lymph node cancer, bladder cancer, biliary tract cancer (gallbladder and biliary tract cancer), endocrine gland cancer, thyroid cancer, parathyroid gland cancer, adrenal cancer, soft tissue sarcoma, urethra cancer, phallus cancer, prostate cancer, chronic or acute leukemia, lymphocytic lymphoma, kidney or ureteral cancer, kidney cell carcinoma, kidney pelvic carcinoma, central nervous system tumors, primary central nervous system lymphoma, spinal cord tumor, brainstem glioma and pituitary adenoma, and preferably is colorectal cancer, pancreatic cancer or biliary tract cancer. One embodiment of the present invention confirmed the anticancer effect of chlorphenesin, chloroquine and chlorphenesin alone, and the anticancer effect by combination treatment according to the combination for mouse-derived colon carcinoma cell line CT26, human-derived colorectal carcinoma cell line HCT116, human-derived colon carcinoma cell line SW480, human-derived pancreatic carcinoma cell line Panc-1, human-derived pancreatic cancer cell line Aspc-1, human-derived pancreatic cancer cell line MIAPaCA2, human-derived gallbladder carcinoma cell line SNU308, and human-derived intrahepatic cholangiocarcinoma cell line SNU1079.

The present invention includes chlorphenesin, chloroquine and chloropyrazine represented by the Chemical Formulas 1 to 3 as well as all their pharmaceutically acceptable salts and possible solvates, hydrates, racemates or stereoisomers thereof.

The chlorphenesin, chloroquine and chloropyrazine represented by the Chemical Formulas 1 to 3 of the present invention may be used in the form of a pharmaceutically acceptable salt, and acid addition salts formed by a pharmaceutically acceptable free acid are useful as a salt. The acid addition salt is obtained from an inorganic acid such as hydrochloric acid, nitric acid, phosphoric acid, sulfuric acid, hydrobromic acid, hydroiodic acid, azilic acid or phosphorous acid, or a non-toxic organic acid such as aliphatic mono or dicarboxylate, phenyl-substituted alkanoate, hydroxyalkanoate and alkanedioate, an aromatic acid, aliphatic and aromatic sulfonic acid. Such pharmaceutically non-toxic salt includes sulfate, pyrosulfate, bisulfate, sulfite, bisulfite, nitrate, phosphate, monohydrogen phosphate, dihydrogen phosphate, metaphosphate, pyrophosphate chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexane-1,6-dioate, benzoate, chlorobenzoate, methylbenzoate, dinitrobenzoate, hydroxybenzoate, methoxybenzoate, phthalate, terephthalate, benzene sulfonate, toluene sulfonate, chlorobenzene sulfonate, xylene sulfonate, phenylacetate, phenylpropionate, phenylbutyrate, citrate, lactate, hydroxybutyrate, glycolate, maleate, tartrate, methanesulfonate, propanesulfonate, naphthalene-1-sulfonate, naphthalene-2-sulfonate, or mandelate.

The acid addition salt according to the present invention can be prepared by the conventional method, for example, by dissolving chlorphenesin, chloroquine and chloropyrazine represented by Chemical Formulas 1 to 3 in an excessive amount of an aqueous acid solution and then precipitating the resulting salts using water-miscible organic solvent, for example, methanol, ethanol, acetone, or acetonitrile. Further, the acid addition salt may be prepared by evaporating a solvent or an excess acid in the mixture followed by performing dry or by suction-filtrating the precipitated salt.

In addition, the pharmaceutically acceptable metal salt may be prepared using a base. An alkali metal or alkali earth metal salt is obtained by, for example, dissolving a compound in an excessive amount of an alkali metal hydroxide or alkali earth metal hydroxide solution, filtering an undissolved compound salt, and evaporating and drying the filtrate. Here, the metal salt considered suitable for pharmaceutical use is a sodium salt, a potassium salt or a calcium salt. Further, a silver salt corresponding thereto is obtained by reacting a salt of an alkali metal or alkali earth metal with a suitable silver salt (e.g., silver nitrate).

The pharmaceutical composition of the present invention may further include known anticancer drugs in addition to chlorphenesin, chloroquine and chloropyrazine as active ingredients, and may be used in combination with other treatments known for the treatment of these diseases. Other treatments include, but are not limited to, chemotherapy, radiation therapy, hormone therapy, bone marrow transplantation, stem cell replacement therapy, other biological therapies, immunotherapy, and the like.

The term "prevention" used herein refers to all types of actions that inhibit or delay the development, spread and recurrence of cancer by administration of the pharmaceutical composition according to the present invention, and the term "treatment" used herein refers to all types of actions that improve or alter the death of cancer cells or symptoms of cancer by the administration of the composition including at least one selected from the group consisting of chlorphenesin, chloroquine and chloropyrazine or a pharmaceutically acceptable salt thereof according to the present invention. Those of ordinary skill in the art can appreciate the exact criteria of the disease on which the compositions herein have effects and determine the extent of improvement, enhancement, and treatment with reference to the data presented by the Korean Academy of Medical Sciences, etc.

The term "therapeutically effective amount" used in combination with the active ingredient in the present invention refers to an amount effective to prevent or treat a subject disease, and the therapeutically effective amount of the composition of the present invention may be determined by various factors, for example, administration method, target site, the patient's condition, and the like. Therefore, the dosage when used in the human body should be determined in appropriate amounts in consideration of safety and efficacy. It is also possible to estimate the amount used in humans from the effective amount determined by animal experiments. These matters to be considered in determining the effective amount are described in, for example, Hardman and Limbird, eds., Goodman and Gilman's The Pharmacological Basis of Therapeutics, 10th ed. (2001), Pergamon Press; and E. W. Martin ed., Remington's Pharmaceutical Sciences, 18th ed. (1990), Mack Publishing Co.

The composition of the present invention is administered in a pharmaceutically effective amount. The term "pharmaceutically effective amount" used herein refers to an amount sufficient to treat the disease at a reasonable benefit/risk ratio applicable for medical treatment and an amount that does not cause side effects. The level of an effective dosage may be determined by parameters including a health status of the patient, the kind of cancer, severity, the activity of a drug, sensitivity to a drug, an administration method, administration time, an administration route and a release rate, duration of treatment, formulated or co-used drugs, and other parameters well known in medical fields. The composition of the present invention may be administered as an individual therapeutic agent or in combination with other therapeutic agents. It may be administered sequentially or simultaneously with a conventional therapeutic agent or administered in a single or multiple dose regime. In consideration of all of the above factors, it is important to administer such a dose as to obtain a maximum effect with a minimal amount without a side effect and the dose may be easily determined by those of ordinary skill in the art.

The pharmaceutical compositions of the present invention may include carriers, diluents, excipients, or a combination of two or more thereof commonly used in biological formulations. The term "pharmaceutically acceptable" as used herein means that the composition is free of toxicity to cells or humans exposed to the composition. The carrier is not particularly limited as long as it is suitable for the delivery of the composition to the living body. For example, compounds, saline solutions, sterile water, Ringer's solution, buffered saline, dextrose solution, maltodextrin solution, glycerol, ethanol disclosed in Merck Index, 13th ed., Merck & Co. Inc. and one or more ingredients thereof may be mixed and used. If necessary, conventional additives such as antioxidants, buffers, bacteriostatic agents may be added. The composition may also be prepared into dosage form for injection such as aqueous solution, suspension, or emulsion, tablet, capsule, powder or pill by additionally including diluents, dispersant, surfactant, binder and lubricant. Further, the composition may be formulated into a desirable form depending on targeting disease or ingredients thereof, using the method disclosed in Remington's Pharmaceutical Science (Mack Publishing Company, Easton Pa., 18th, 1990).

In one embodiment, the pharmaceutical composition may be one or more formulations selected from the group consisting of oral formulations, external preparations, suppositories, sterile injectable solutions and sprays, and more preferably oral formations or injectable formulations.

The term "administration" as used herein means providing a predetermined substance to an individual or a patient by any appropriate method and may be administered orally or parenterally (for example, by applying in injectable formulations intravenously, subcutaneously, intraperitoneally, or topically). The dosage may vary depending on the patient's body weight, age, sex, health condition, diet, administration time, administration method, excretion rate, the severity of the disease and the like. The liquid formulations for oral administration of the composition of the present invention include suspensions, oral liquids, emulsions, syrups and the like. In addition to water and liquid paraffin which are simple diluents commonly used, various excipients such as wetting agents, sweeteners, flavors, preservatives and the like may be included. Formulations for parenteral administration include sterile aqueous solutions, non-aqueous solvents, suspensions, emulsions, freeze-dried formulations, suppositories, and the like. The pharmaceutical composition of the present invention may be administered by any device capable of moving the active substance to target cells. The preferred administration method and formulations include intravenous, subcutaneous, intradermal, intramuscular, drip injections and the like. The injectable solution may be prepared using an aqueous solvent such as a physiological saline solution and Ringer's solution and a non-aqueous solvent such as a vegetable oil, a higher fatty acid ester (e.g., ethyl oleate), an alcohol (e.g., ethanol, benzyl alcohol, propylene glycol, glycerin, etc.) and may include pharmaceutical carriers such as stabilizer to prevent deterioration (e.g., ascorbic acid, sodium hydrogen sulfite, sodium pyrophosphate, BHA, tocopherol, EDTA, etc.), an emulsifier, a buffer for pH control, preservatives for inhibition of microbial growth (e.g., phenylmercuric nitrate, thimerosal, benzalkonium chloride, phenol, cresol, benzyl alcohol, etc.).

The term "individual" as used herein means all animals who have developed the cancer or are capable of developing the cancer, including human, a monkey, a cow, a horse, a sheep, a pig, a chicken, a turkey, a quail, a cat, a dog, a mouse, a rat, a rabbit or a guinea pig. These diseases can be effectively prevented or treated by administering the pharmaceutical composition of the present invention to an individual. The pharmaceutical composition of the present invention can be administered in combination with conventional therapeutic agents.

The pharmaceutical composition of the present invention can further include a pharmaceutically acceptable additive, which is exemplified by starch, gelatinized starch, microcrystalline cellulose, milk sugar, povidone, colloidal silicon dioxide, calcium hydrogen phosphate, lactose, mannitol, taffy, Arabia rubber, pregelatinized starch, corn starch, cellulose powder, hydroxypropyl cellulose, Opadry, sodium starch glycolate, carnauba wax, synthetic aluminum silicate, stearic acid, magnesium stearate, aluminum stearate, calcium stearate, white sugar, dextrose, sorbitol, talc, etc. The pharmaceutically acceptable additive of the present invention is preferably added to the composition in an amount of 0.1 to 90 parts by weight but is not limited thereto.

In an aspect, the present invention relates to the pharmaceutical composition for inhibiting cancer proliferation and metastasis, in which the composition includes at least one selected from the group consisting of chlorphenesin, chloroquine and chloropyrazine, or a pharmaceutically acceptable salt thereof as an active ingredient.

In one embodiment, chlorphenesin may be represented by the following Chemical Formula 1, chloroquine may be represented by the following Chemical Formula 2, and chloropyrazine may be represented by the following Chemical Formula 3:

[Chemical Formula 1]

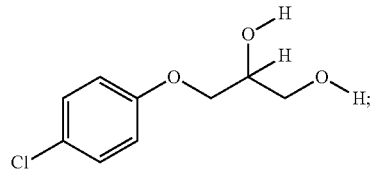

[Chemical Formula 2]

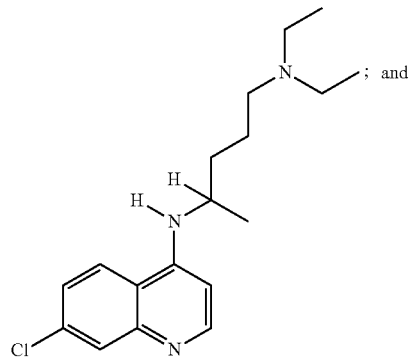

-continued

[Chemical Formula 3]

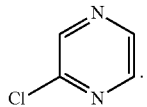

In one embodiment, the chlorphenesin may be a chlorphenesin carbamate represented by the following Chemical Formula 4:

[Chemical Formula 4]

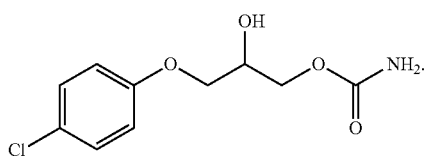

In one embodiment, the pharmaceutical composition of the present invention may include chlorphenesin and chloroquine, chlorphenesin and chloropyrazine, chloroquine and chloropyrazine, or chlorphenesin, chloroquine and chlorphenesin, or a pharmaceutically acceptable salt thereof as an active ingredient. The pharmaceutical composition preferably includes chlorphenesin and chloroquine, or chlorphenesin and chloropyrazine because they have a synergistic inhibition effect of metastasis and invasion.

In one embodiment, the pharmaceutical composition of the present invention may include 5 to 500 µM chlorphenesin, 0.5 to 25 µM chloroquine, or 1 to 100 µM chloropyrazine. The pharmaceutical composition may include 5 µM chlorphenesin (fixed concentration) and 0.5 to 25 µM chloroquine when chlorphenesin and chloroquine are included in combination. The pharmaceutical composition may include 5 µM chlorphenesin (fixed concentration) and 25 to 50 µM chloropyrazine when chlorphenesin and chloropyrazine are included in combination. In an example of the present invention, it inhibits the migration and invasion of cancer cells without significant cytotoxicity in the above-described range of concentration.

The chlorphenesin of the present invention can inhibit only proliferation and metastasis of cancer cells, not the death of cancer cells, at a low concentration of 0.1 µM to 10 mM. For example, the compositions of the present invention may include chlorphenesin having a low concentration of ranging from 1 µM to 1 mM. In the case of chlorphenesin at a concentration of less than 1 µM, the cancer proliferation and metastasis inhibitory effect is reduced compared with 1 µM, and cytotoxicity may be exhibited at concentrations of more than 1 mM, particularly, 10 mM or more.

In an embodiment, the cancer may be colorectal cancer, pancreatic cancer or biliary tract cancer. One embodiment of the present invention confirmed the cancer cell metastasis and invasion inhibitory effect of chlorphenesin, chloroquine and chloropyrazine alone, and the cancer cell metastasis and invasion inhibitory effect by combination treatment according to the combination thereof for mouse-derived colon carcinoma cell line CT26, human-derived colorectal carcinoma cell line HCT116, human-derived colon carcinoma cell line SW480, human-derived pancreatic carcinoma cell line Panc-1, human-derived pancreatic cancer cell line Aspc-1, human-derived pancreatic cancer cell line MIAPaCA2, human-derived gallbladder carcinoma cell line SNU308, and human-derived intrahepatic cholangiocarcinoma cell line SNU1079.

In an aspect, the present invention relates to the cancer adjuvant including at least one selected from the group consisting of chlorphenesin, chloroquine and chloropyrazine, or a pharmaceutically acceptable salt thereof as an active ingredient.

In an embodiment, the chlorphenesin of the present invention can inhibit only proliferation and metastasis of cancer cells, not the death of cancer cells, at a low concentration so that cytotoxicity can be minimized when co-administered with an anticancer drug having cytotoxicity. For example, the compositions of the present invention may include chlorphenesin having a low concentration of ranging from 1 µM to 1 mM. In the case of chlorphenesin at a concentration of less than 1 µM, there is no the cancer proliferation and metastasis inhibitory effect, and cytotoxicity may be exhibited at concentrations of more than 1 mM, particularly, 10 mM or more.

In one embodiment, chlorphenesin and chloroquine, or chlorphenesin and chloropyrazine may be included as active ingredients. In one embodiment of the present invention, it is confirmed that the tumor size and metastasis induced by mouse-derived colon carcinoma cell line CT26 are significantly inhibited by the combination treatment of chlorphenesin and an anticancer agent.

Examples of anticancer agents that may be included in the pharmaceutical composition of the present invention include DNA alkylating agents such as mechloethamine, chlorambucil, phenylalanine, mustard, cyclophosphamide, ifosfamide, carmustine (BCNU), lomustine (CCNU), streptozotocin, busulfan, thiotepa, cisplatin and carboplatin; anticancer antibiotics such as dactinomycin (actinomycin D), doxorubicin (adriamycin), daunorubicin, idarubicin, mitoxantrone, plicamycin, mitomycin C and bleomycin; and plant alkaloids such as vincristine, vinblastine, paclitaxel, docetaxel, etoposide, teniposide, topotecan and iridotecan, but are not limited thereto.

In an aspect, the present invention relates to the food composition for preventing or ameliorating cancer, the composition including at least one selected from the group consisting of chlorphenesin, chloroquine and chloropyrazine.

When the composition of the present invention is used as a food composition, the chlorphenesin, chloroquine or chloropyrazine may be added as it is or may be used together with other food or food ingredients, and may be appropriately used according to a conventional method. The composition may include a sitology-acceptable food-aid additive in addition to the active ingredients, and the mixed amount of the active ingredient may be suitably determined according to the intended use (prevention, health or therapeutic treatment).

The term "food-aid additive" as used herein refers to a component which can be added to foods subsidiarily and may be appropriately selected and used by those skilled in the art as added to the preparation of health functional foods of each formulation. Examples of food-aid additives include various nutrients, vitamins, minerals (electrolytes), flavors such as synthetic flavors and natural flavors, colorants and fillers, pectic acid and its salts, alginic acid and its salts, organic acids, protective colloid thickeners, pH adjusting agents, stabilizers, preservatives, glycerin, alcohols, and carbonating agents used in carbonated drinks. However, the types of food aid additives of the present invention are not limited by these examples.

A health functional food may be included in the food composition of the present invention. The term "health functional food" as used herein refers to a food prepared and processed in the form of tablets, capsules, powders, granules, liquids and pills using raw materials and components having useful functions in the human body. Here, "functional" means to obtain beneficial effects for health use such as controlling nutrients or physiological action for the structure and function of the human body. The health functional food of the present invention can be prepared by a method commonly used in the art and can be prepared by adding raw materials and components which are usually added in the conventional technical fields at the time of the preparation. Further, the formulations of the above health functional foods may also be prepared without limitations as long as formulations recognized as health functional foods. The food composition of the present invention can be prepared in various forms, and unlike general pharmaceuticals, it has the advantage that there is no side effect that may occur when a drug is used for a long period of time, and is excellent in portability, so that the health functional food of the present invention may be ingested as an adjuvant to enhance the effectiveness of anticancer drugs.

There is no limitation on the kind of health food to which the composition of the present invention can be used. Moreover, the composition including chlorphenesin, chloroquine or chloropyrazine of the present invention as an active ingredient may be prepared by mixing other suitable auxiliary ingredients and known additives, which may be contained in health functional foods, according to the selection of a person skilled in the art. Examples of foods that may be added include meat, sausage, bread, chocolates, candies, snacks, confectionery, pizza, ramen, other noodles, gums, dairy products such as ice cream, various soups, beverages, tea, drinks, alcohol drinks, vitamin complex, and the like, and can be prepared by adding to the juice, tea, jelly, and juice prepared from the extract of the present invention as a main component.

In an aspect, the present invention relates to the method for treating cancer, in which the method includes administering at least one selected from the group consisting of chlorphenesin, chloroquine and chloropyrazine, or a pharmaceutically acceptable salt thereof to a subject having cancer in a pharmaceutically effective amount.

In one embodiment, chlorphenesin and chloroquine, chlorphenesin and chloropyrazine, chloroquine and chloropyrazine, or chlorphenesin, chloroquine and chlorpyrazine, or a pharmaceutically acceptable salt thereof may be administered. Chlorphenesin and chloroquine, or chlorphenesin and chloropyrazine may be administered in combination because they have a synergistic anticancer effect.

In one embodiment, the pharmaceutical composition of the present invention may include 5 to 500 µM chlorphenesin, 0.5 to 25 µM chloroquine, or 1 to 100 µM chloropyrazine. The pharmaceutical composition may include 5 µM chlorphenesin (fixed concentration) and 0.5 to 25 µM chloroquine when chlorphenesin and chloroquine are included in combination. The pharmaceutical composition may include 5 µM chlorphenesin (fixed concentration) and 25 to 50 µM chloropyrazine when chlorphenesin and chloropyrazine are included in combination. In an example of the present invention, it inhibits the migration and invasion of cancer cells without significant cytotoxicity in the above-described range of concentration.

In one embodiment, the cancer may be at least one selected from the group consisting of brain tumor, melanoma, myeloma, non-small cell lung cancer, oral cancer, liver cancer, gastric cancer, colon cancer, breast cancer, lung cancer, bone cancer, pancreatic cancer, skin cancer, head or neck cancer, cervical cancer, ovarian cancer, colorectal cancer, small intestine cancer, rectal cancer, fallopian tube cancer, anal cancer, endometrial carcinoma, vaginal carcinoma, vulvar carcinoma, Hodgkin's disease, esophageal cancer, lymph node cancer, bladder cancer, biliary tract cancer (gallbladder and biliary tract cancer), endocrine gland cancer, thyroid cancer, parathyroid gland cancer, adrenal cancer, soft tissue sarcoma, urethra cancer, phallus cancer, prostate cancer, chronic or acute leukemia, lymphocytic lymphoma, kidney or ureteral cancer, kidney cell carcinoma, kidney pelvic carcinoma, central nervous system tumors, primary central nervous system lymphoma, spinal cord tumor, brainstem glioma and pituitary adenoma, and preferably is colorectal cancer, pancreatic cancer or biliary tract cancer.

In an aspect, the present invention relates to a use of at least one selected from the group consisting of chlorphenesin, chloroquine and chloropyrazine, or a pharmaceutically acceptable salt thereof for preparing a pharmaceutical composition for preventing or treating cancer.

The present invention is described in more detail with reference to the following Examples. However, the following Examples are only for the purpose of illustrating the present invention, and thus the present invention is not limited thereto.

Example 1. Confirmation of Anti-Cancer Effect and Metastasis Inhibitory Effect on Colorectal Cancer 1-1. Confirmation of Cell Survival Rate 1-1-1. Confirmation of Cell Survival Rate by Single Administration In order to confirm the effect of chlorphenesin (named as OC-201), chloroquine (named as OC-202) and chloropyrazine (named as OC-203) alone on the survival rate of colorectal cancer cells, cell survival rate was evaluated for the colorectal cancer cell lines CT26, HCT116 and SW480 cell lines by MTT assay (Promega, Ltd.) according to the manufacturer's protocol. Each colorectal cancer cell line was inoculated in a 96-well plate at a density of $5\times10^3$ cells per well and pre-treated with 0 µM (control: DMSO treatment) 10 µM, 25 µM, 50 µM, 100 µM, 250 µM, 500 µM and 1 mM of chlorphenesin (OC-201), chloroquine (OC-202) and chloropyrazine (OC-203) for 24 hours, 48 hours and 72 hours, respectively. The pre-treated cell lines were incubated with 5 mg/mL MTT for 4 hours. Thereafter, the medium was removed, and 150 µL of the solubilization solution and the stop solution were added, followed by incubation at 30° C. for 4 hours. The absorbance of the reaction solution was measured at 570 nm. The cell survival rate was calculated using the following Equation 1.

Cell survival rate=absorbance of experimental group (at 570 nm)/absorbance of control (at 570 nm)× 100(%)  [Equation 1]

As a result, it was confirmed that when OC-201 was more than 500 µM, and OC-202 was more than 10 µM, they showed toxicity, and OC-203 was not to be toxic at 100 µM or less as shown in FIGS. 1 to 3.

1-1-2. Confirmation of Cell Survival Rate by Combination Administration

In order to confirm the cell survival rate of colorectal cancer cell by combination treatment of chlorphenesin (OC-201), chloroquine (OC-202) and chloropyrazine (OC-203), cell survival rate was evaluated for the colorectal cancer cell lines CT26, HCT116 and SW480 by MTT assay (Promega, Ltd.) according to the manufacturer's protocol. Each colorectal cancer cell line was inoculated in a 96-well plate at a density of $5\times10^3$ cells per well and pre-treated with control (DMSO treatment), chlorphenesin (5 µM), chlorphenesin and chloroquine (5 µM+500 nM, 5 µM+1 µM, 5 µM+5 µM, 5 µM+10 µM, 5 µM+25 µM and 5 µM+5004), chlorphenesin and chloropyrazine (5 µM+1 µM, 5 µM+5 µM, 5 µM+10 µM, 5 µM+25 µM, 5 µM+50 µM and 5 µM+100 µM) for 24 hours, 48 hours and 72 hours, respectively. The pre-treated cell lines were incubated with 5 mg/mL MTT for 4 hours. Thereafter, the medium was removed, and 150 µL of the solubilization solution and the stop solution were added, followed by incubation at 30° C. for 4 hours. The absorbance of the reaction solution was measured at 570 nm. The cell survival rate was calculated using the above Equation 1.

As a result, when 5 µM chlorphenesin was used in combination with chloroquine at 25 µM or more, it was toxic to colorectal cancer (FIG. 4). When 5 µM chlorphenesin was used in combination with chloropyrazine at 100 µM or less, it was not toxic to colorectal cancer (FIG. 5).

1-2. Confirmation of Cell Migration
1-2-1. Migration Assay
1-2-1-1. Single Administration by Chlorphenesin Cancer cell metastasis should be based on cell motility. Therefore, the mobility of the colorectal cancer cell lines SW480, HCT116 and CT26 cell lines according to the treatment concentration of chlorphenesin (OC-201) was confirmed by the migration assay. Specifically, the colorectal cancer cell lines CT26, HCT116, and SW480 were suspended in serum-free RPMI and added at $1\times10^5$ cells/well in the upper chamber of a 24 well transwell chamber with a polycarbonate membrane (8.0 µm pore size, Costar). Laminin (10 µg/ml) was placed in the lower well, and each cell was treated with chlorphenesin (OC-201) having 0 µM (control DMSO treatment), 5 µM, 10 µM, 25 µM, 50 µM, 100 µM, 250 µM, 500 µM, 1 mM and 2 mM, respectively. Cells were cultured for 18 hours in a $CO_2$ incubator at 37° C. and allowed to migrate. The cells were then fixed with 70% methyl alcohol in PBS for 30 minutes and washed three times with PBS. The cells were stained with hematoxylin (Sigma) for 10 minutes and washed with distilled water. Unmigrated cells were removed from the top surface of the membrane with a cotton swab. Membranes were removed from the chamber and fixed with Gel Mount (Biomeda, Foster City, Calif., USA). The migrated cells (cells attached to the lower surface of the membrane) were counted in a randomly selected scope in a high power field (×20).

As a result, when SW480 cell line was treated with the chlorphenesin (OC-201) at 25 µM or more, their cell migration was significantly reduced (FIGS. 6 and 7). In addition, in HCT116 cell line, the cell migration was decreased when treated with chlorphenesin (OC-201), specially when treated at 250 µM or more (FIGS. 8 and 9). In addition, in the CT26 cell line, the cell migration was decreased when treated with chlorphenesin (OC-201), specially when treated at 250 µM or more (FIGS. 10 and 11).

1-2-1-2. Combination Administration

The degree of migration of colorectal cancer cell lines CT26, HCT116 and SW480 was observed when treated with chlorphenesin (OC-201), chloroquine (OC-202) and chloropyrazine (OC-203) alone and treated with chlorphenesin and chloroquine or chloropyrazine in combination. Specifically, the colorectal cancer cell lines CT26, HCT116 or SW480 were treated with a control (DMSO treatment), chlorphenesin (5 µM), chloroquine (5 µM, 10 µM or 25 µM), chloropyrazine (25 µM or 50 µM), chlorphenesin and chloroquine (5 µM+5 µM, 5 µM+10 µM, 5 µM+25 µM), and chlorphenesin and chloropyrazine (5 µM+25 µM, 5 µM+50 µM), and the degree of cell migration was then confirmed in the same manner as in the above Examples. In addition, the synergy effect of combination treatment was calculated by the Combination Index (CI) according to the concentration of the combination treatment of chlorphenesin and chloroquine or chloropyrazine using Compusyn software.

Figure 18:
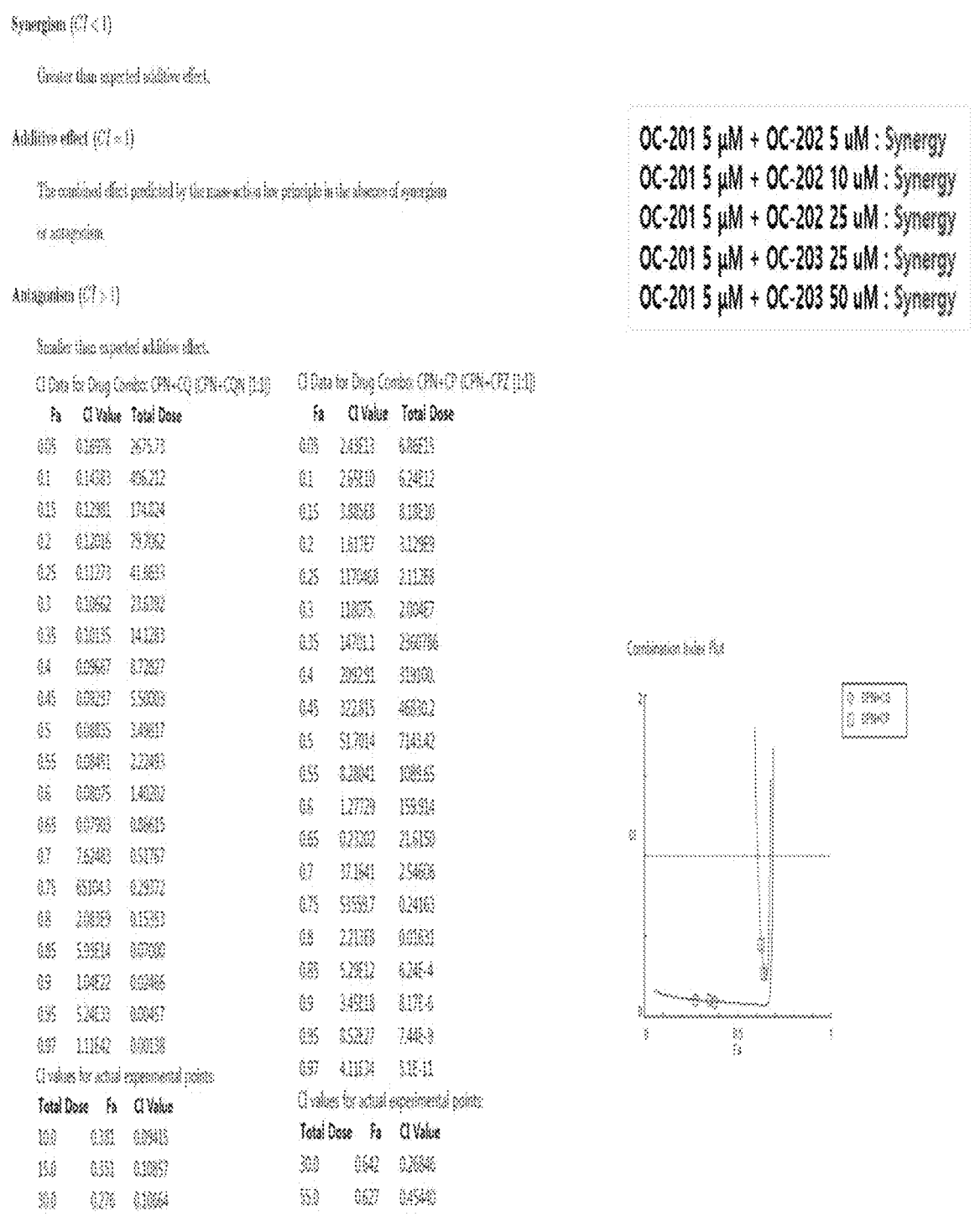

As a result, the migration of all colorectal cancer cell lines CT26, HCT116 and SW480 was decreased when treated with chlorphenesin and chloroquine or chlorphenesin and chloropyrazine in combination than when treated with chloroquine (OC-202) and chloropyrazine (OC-203) alone, respectively (FIGS. 12 to 17). In addition, synergistic action was showed when chlorphenesin was combined with chloroquine or chloropyrazine. In particular, when chlorphenesin and chloroquine were used in combination, the synergistic action was exhibited in all cell lines (FIGS. 18 to 20).

1-2-2. Wound Healing Assay
1-2-2-1. Single Administration by Chlorphenesin

Cancer cell metastasis should be based on cell motility. Therefore, the degree of migration of the colorectal cancer cell line HCT116 according to the treatment of chlorphenesin (OC-201) alone was confirmed by the wound healing assay. Specifically, the colorectal cancer cell line HCT116 was added to RPMI supplemented with 10% FBS. After 24 hours, the cells were inoculated on a 24-well tissue culture plate at the concentration in which 70% to 80% confluence was reached by a monolayer. A scratch was carefully and slowly applied to the monolayer with a new 200 µl yellow pipet tip across the center of the well. The resulting gap distance was equal to the outer diameter of the tips. After scratching, the dish was carefully washed twice with medium to remove the separated cells. Thereafter, the cells were treated with chlorphenesin at 0 µM (DMSO), 5 µM, 10 µM, 25 µM, 50 µM, 250 µM, 500 µM or 1 mM, respectively. After incubated for 0 hour, 8 hours and 24 hours, the cells were observed using a microscope, and the results were graphed.

As a result, when treated with chlorphenesin at 25 µM or more, the migration of colorectal cancer cells was decreased (FIGS. 21 to 23).

1-2-2-2. Combination Administration

The degree of migration of the colorectal cancer cell line HCT116 according to the single treatment with chloroquine (OC-202) and chloropyrazine (OC-203) and the combination treatment with chlorphenesin (OC-201) and chloroquine (OC-202) or chloropyrazine (OC-203) was confirmed. Specifically, the colorectal cancer cell line HCT116 was added to RPMI supplemented with 10% FBS. After 24 hours, the cells were inoculated on a 24-well tissue culture plate at the concentration in which 70% to 80% confluence was reached by a monolayer. A scratch was carefully and slowly applied to the monolayer with a new 200 µl yellow pipet tip across the center of the well. The resulting gap distance was equal to the outer diameter of the tips. After scratching, the dish was carefully washed twice with medium to remove the separated cells. Thereafter, the cells were treated with chloroquine alone (5 µM, 10 µM or 25 µM), chloropyrazine alone (25 µM or 50 µM), chlorphenesin and chloroquine in combination (5 µM+5 µM, 5 µM+10 µM, 5 µM+25 µM), and chlorphenesin and chloropyrazine in combination (5 µM+25 µM, 5 µM+50 µM). After incubated for 0 hour, 8 hours and 24 hours, the degree of cell migration was confirmed in the same manner as in Example 1-2-2-1.

As a result, the migration of colorectal cancer cells was decreased when treated with chlorphenesin and chloroquine (OC-202) or chloropyrazine (OC-203) compared to when treated with chloroquine (OC-202) or chloropyrazine (OC-203) alone, respectively (FIGS. 24 to 26).

1-3. Anchorage Independent Growth Assay 1-3-1. Single Administration by Chlorphenesin Anchorage independent growth is a critical property that distinguishes normal cells from cancer cells. It requires anchorage when normal cells proliferate, but cancer cells may survive and multiply without anchorage. In other words, the normal cells may not proliferate unless the cells adhere to the culture plate, but the cancer cells can proliferate in a floating state without cell anchorage like a soft agar. These properties are utilized to confirm their anchorage independent growth though soft agar colony formation assay. First, a colony formation assay was performed in order to confirm anchorage independent growth of colorectal cancer cell lines through the single administration of chlorphenesin. Specifically, 3,000 colorectal cancer cell lines HCT116 were mixed with a soft agar, and the mixture was divided into 6-well plates and then treated with chlorphenesin at 0 μM (DMSO), 5 μM, 10 μM, 25 μM, 50 μM, 100 μM, 250 μM, 500 μM, 1 mM or 2 mM, respectively. Subsequently, chlorphenesin was supplemented whenever cell culture medium was replaced. After 3 weeks, cells were observed.

As a result, as shown in FIG. 27, when the chlorphenesin was used at 250 μM or more, the colony forming ability was decreased.

1-3-2. Combination Administration

In order to confirm whether the combination administration of chlorphenesin and chloroquine (OC-202) or chloropyrazine (OC-203) inhibits the anchorage independent growth of colorectal cancer cell lines compared to the single administration as described above, colorectal cancer cell lines HCT116 and CT26 were treated with chlorphenesin (5 μM), chloroquine (10 μM or 25 μM), chloropyrazine (10 μM), chlorphenesin and chloroquine (5 μM+10 μM or 5 μM+25 μM), chlorphenesin and chloropyrazine (5 μM+10 μM, 5 μM+25 μM or 5 μM+50 μM), and the colony formation assay was performed.

As a result, the colony formation was decreased when chlorphenesin and chloroquine were used in combination than when chloroquine or chloropyrazine alone, respectively, were treated (FIGS. 28 and 29).

Example 2. Confirmation of Effect on Pancreatic Cancer 2-1. Confirmation of Cell Survival Rate 2-1-1. Confirmation of Cell Survival Rate by Single Administration In order to confirm the effect of single administration of chlorphenesin (OC-201), chloroquine (OC-202) and chloropyrazine (OC-203), respectively, on the survival rate of pancreatic cancer cells, cell survival rate was evaluated for the pancreatic cancer cell lines Aspc-1, MIAPaCA2 and Panc-1 by MTT assay (Promega, Ltd.) according to the manufacturer's protocol. Each pancreatic cancer cell line was inoculated in a 96-well plate at a density of 5×10³ cells per well and pre-treated with 0 μM (control: DMSO treatment), 5 μM, 10 μM, 25 μM, 50 μM, 100 μM, 250 μM, 500 μM and 1 mM (1000 μM) of chlorphenesin (OC-201), 0 μM (control: DMSO treatment), 0.5 μM, 1 μM, 5 μM, 10 μM, 25 μM, 50 μM and 100 μM of chloroquine (OC-202) and 0 μM (control: DMSO treatment), 1 μM, 5 μM, 10 μM, 25 μM, 50 μM and 100 μM of chloropyrazine (OC-203) for 24 hours, 48 hours and 72 hours, respectively. The pre-treated cell lines were incubated with 5 mg/ml MTT for 4 hours. Thereafter, the medium was removed, and 150 μL of the solubilization solution and the stop solution were added, followed by incubation at 30° C. for 4 hours. The absorbance of the reaction solution was measured at 570 nm. The cell survival rate was calculated using the equation 1 as described above.

As a result, as shown in FIGS. 30 to 32, chlorphenesin and chloropyrazine single-administrated group did not show cytotoxicity even at high doses, but chloroquine showed cytotoxicity at concentrations of 50 μM or more.

2-1-2. Confirmation of Cell Survival Rate by Combination Administration

In order to confirm the pancreatic cancer cell survival rate by combination treatment of chlorphenesin (OC-201), chloroquine (OC-202) and chloropyrazine (OC-203), cell survival rate was evaluated for the pancreatic cancer cell lines Aspc-1, MIAPaCA2 and Panc-1 by MTT assay (Promega, Ltd.) according to the manufacturer's protocol. Each pancreatic cancer cell line was inoculated in a 96-well plate at a density of 5×10³ cells per well and pre-treated with control (DMSO treatment), chlorphenesin (5 μM), chlorphenesin and chloroquine (combination treatment with 5 μM of chlorphenesin and 1 μM, 5 μM, 10 μM, 25 μM or 50 μM of chloroquine, respectively, combination treatment with 0.5 μM of chloroquine and 1 μM, 5 μM, 10 μM, 25 μM or 50 μM of chlorphenesin, respectively, combination treatment with 1 μM of chloroquine and 1 μM, 5 μM, 10 μM, 25 μM or 50 μM of chlorphenesin, respectively or combination treatment with 5 μM of chloroquine and 1 μM, 5 μM, 10 μM, 25 μM or 50 μM of chlorphenesin, respectively) or chlorphenesin and chloropyrazine (combination treatment with 5 μM of chlorphenesin and 1 μM, 5 μM, 10 μM, 25 μM or 50 μM of chloropyrazine, respectively) for 24 hours, 48 hours and 72 hours, respectively. The pre-treated cell lines were incubated with 5 mg/ml MTT for 4 hours. Thereafter, the medium was removed, and 150 μL of the solubilization solution and the stop solution were added, followed by incubation at 30° C. for 4 hours. The absorbance of the reaction solution was measured at 570 nm. The cell survival rate was calculated using the above equation 1.

As a result, when 1 μM to 50 μM of chloroquine was treated in combination with 5 μM of chlorphenesin (FIG. 33), when 1 μM to 50 μM of chlorphenesin was treated in combination with 0.5 μM of chloroquine (FIG. 34), 1 μM to 50 μM of chlorphenesin was treated in combination with 1 μM of chloroquine (FIG. 35), when 1 μM to 50 μM of chlorphenesin was treated in combination with 5 μM of chloroquine (FIG. 36), no significant cytotoxicity was observed in the pancreatic cancer cell line for 72 hours. When 5 μM of chlorphenesin was treated in combination with 1 μM to 25 μM of chloropyrazine (FIG. 37), no significant cytotoxicity was observed in the pancreatic cancer cell line for 24 hours.

2-2. Cell Migration Assay 2-2-1. Comparison of Single Administration and Combination Treatment The degree of migration of pancreatic cancer cell lines Panc-1 and Aspc-1 was confirmed as the same manner in Example 1-2-1 when treated with chlorphenesin (OC-201), chloroquine (OC-202) and chloropyrazine (OC-203) alone and treated with chlorphenesin and chloroquine or chloropyrazine in combination. Specifically, the pancreatic cancer cell lines Panc-1 and Aspc-1 were treated with a control (DMSO treatment), chlorphenesin (5 μM), chloroquine (5 μM, 10 μM or 25 μM), chloropyrazine (25 μM or 50 μM), chlorphenesin and chloroquine (5 μM+5 μM, 5 μM+10 μM, 5 μM+25 μM), and chlorphenesin and chloropyrazine (5 μM+25 μM, 5 μM+50 μM), and the degree of cell migration was then confirmed in the same manner as in the above Example 1-2-1. In addition, the synergy effect of combination treatment was calculated by the Combination Index (CI) according to the treatment of the combination concentration of chlorphenesin and chloroquine or chloropyrazine using Compusyn software.

As a result, the migration of Panc-1 cells was decreased in chlorphenesin, chloroquine and chloropyrazine single administrated groups (FIGS. 38 and 39), and in the group treated with 5 μM of chlorphenesin and 10 μM of chloroquine, and 5 μM of chlorphenesin and 25 μM or more of chloropyrazine, synergy effect was observed (FIG. 39). In addition, the migration of cells in the Aspc-1 cell line was also decreased in chlorphenesin, chloroquine and chloropyrazine single administrated groups (FIGS. 40 and 41), and synergy effect on the cell migration decrease was observed in all groups treated with chlorphenesin and chloroquine or chloropyrazine in combination (FIG. 41).

2-3. Invasion Assay

In order to confirm whether the chlorphenesin (OC-201), chloroquine (OC-202) and chloropyrazine (OC-203) of the present invention inhibits the characteristics of cancer cells which pierces thin membrane surrounding the cell's tissues or degrades the extracellular matrix filling the intercellular space to invade and metastasize into other parts, the invasion assay was performed using matrigel simulating extracellular matrix.

Specifically, the pancreatic cancer cell lines Panc-1 and MIACaPa2 were suspended in serum-free RPMI and added at $1 \times 10^5$ cells/well in the upper chamber of a 24 well transwell chamber with a polycarbonate membrane (8.0 μm pore size, Costar). Matrigel (10 μg/ml) was placed in the lower well, and each cell was treated with control (DMSO treatment), chlorphenesin (5 μM), chloroquine (5 μM, 10 μM or 25 μM), chloropyrazine (25 μM or 50 μM), chlorphenesin and chloroquine (5 μM+5 μM, 5 μM+10 μM, 5 μM+25 μM), and chlorphenesin and chloropyrazine (5 μM+25 μM, 5 μM+50 μM), respectively. Cells were then cultured for 18 hours in a $CO_2$ incubator at 37° C. The cells were then fixed with 70% methyl alcohol in PBS for 30 minutes and washed three times with PBS. The cells were stained with hematoxylin (Sigma) for 10 minutes and washed with distilled water. Unmigrated cells were removed from the top surface of the membrane with a cotton swab. Membranes were removed from the chamber and fixed with Gel Mount (Biomeda, Foster City, Calif., USA). The migrated cells (cells attached to the lower surface of the membrane) were counted in a randomly selected scope in a high power field (×20). In addition, the synergy effect of combination treatment was calculated by the Combination Index (CI) according to the concentration of the combination treatment of chlorphenesin and chloroquine or chloropyrazine using Compusyn software.

As a result, invasion of Panc-1 and MIACaPa2 was inhibited in chlorphenesin, chloroquine and chloropyrazine single administered groups as shown in FIGS. 42 and 44. In both pancreatic cancer cell lines, synergy effects by chlorphenesin and chloroquine or chloropyrazine combination treatment were showed (FIGS. 43 and 45).

Example 3. Confirmation of Effect on Biliary Tract Cancer 3-1. Confirmation of Cell Survival Rate 3-1-1. Confirmation of Cell Survival Rate by Single Administration In order to confirm the effect of single administration of chlorphenesin (OC-201), chloroquine (OC-202) and chloropyrazine (OC-203), respectively, on the survival rate of biliary tract cancer cells, cell survival rate was evaluated for the biliary tract cancer cell lines SNU1079 and SNU308 by MTT assay (Promega, Ltd.) according to the manufacturer's protocol. Each biliary tract cancer cell line was inoculated in a 96-well plate at a density of $5 \times 10^3$ cells per well and pre-treated with 0 μM (control: DMSO treatment), 5 μM, 10 μM, 25 μM, 50 μM, 100 μM, 250 μM, 500 μM and 1 mM (1000 μM) of chlorphenesin (OC-201), 0 μM (control: DMSO treatment), 1 μM, 5 μM, 10 μM, 25 μM, 50 μM and 100 μM of chloroquine (OC-202) and 0 μM (control: DMSO treatment), 1 μM, 5 μM, 10 μM, 25 μM, 50 μM and 100 μM of chloropyrazine (OC-203) for 24 hours, 48 hours and 72 hours, respectively. The pre-treated cell lines were incubated with 5 mg/ml MTT for 4 hours. Thereafter, the medium was removed, and 150 μL of the solubilization solution and the stop solution were added, followed by incubation at 30° C. for 4 hours. The absorbance of the reaction solution was measured at 570 nm. The cell survival rate was calculated using equation 1 as described above.

As a result, as shown in FIGS. 46 to 48, chlorphenesin showed apparent cytotoxicity at 1 mM or more after 48 hours, SNU1079 treated with chloroquine showed cytotoxicity at a concentration of 50 μM or more for 24 hours and of 25 μM or more after 48 hours, and SNU 308 cell line showed cytotoxicity at a concentration of 50 μM or more after 48 hours. Chloropyrazine single group did not show cytotoxicity even at high dose.

3-1-2. Confirmation of Cell Survival Rate by Combination Administration

In order to confirm the biliary tract cancer cell survival rate by combination treatment of chlorphenesin (OC-201), chloroquine (OC-202) and chloropyrazine (OC-203), cell survival rate was evaluated for the biliary tract cancer cell lines SNU1079 and SNU308 by MTT assay (Promega, Ltd.) according to the manufacturer's protocol. Each biliary tract cancer cell line was inoculated in a 96-well plate at a density of $5 \times 10^3$ cells per well and pre-treated with control (DMSO treatment), chlorphenesin (OC-201) (5 μM), chlorphenesin and chloroquine (OC-202) in combination (combination treatment with 5 μM chlorphenesin and 1 μM, 5 μM, 10 μM, 25 μM or 50 μM of chloroquine, respectively), or chlorphenesin and chloropyrazine (OC-203) in combination (combination treatment with 5 μM chlorphenesin and 1 μM, 5 μM, 10 μM, 25 μM, 50 μM, or 100 μM of chloropyrazine, respectively) for 24 hours, 48 hours and 72 hours, respectively. The pre-treated cell lines were incubated with 5 mg/ml MTT for 4 hours. Thereafter, the medium was removed, and 150 μL of the solubilization solution and the stop solution were added, followed by incubation at 30° C. for 4 hours. The absorbance of the reaction solution was measured at 570 nm. The cell survival rate was calculated using the above equation 1.

As a result, the cytotoxicity was observed in the biliary tract cancer cell line when 5 μM of chlorphenesin and 50 μM or more of chloroquine were combined (FIG. 49) and 5 μM of chlorphenesin and 100 μM of chloropyrazine were combined (FIG. 50).

3-2. Confirmation of Cell Migration 3-2-1. Single Administration by Chlorphenesin The mobility of the biliary tract cancer cell line SNU1079 according to the treatment concentration of chlorphenesin (OC-201) was confirmed by the migration assay. Specifically, the biliary tract cancer cell line SNU1079 was suspended in serum-free RPMI and added at $1 \times 10^5$ cells/well in the upper chamber of a 24 well transwell chamber with a polycarbonate membrane (8.0 μm pore size, Costar). Laminin (10 μg/ml) was placed in the lower well, and cells were treated with 5 μM, 10 μM, 25 μM, 50 μM, 100 μM, 250 μM, 500 μM, 1 mM or 2 mM of chlorphenesin. Cells were then cultured for 18 hours in a $CO_2$ incubator at 37° C. The cells were then fixed with 70% methyl alcohol in PBS for 30 minutes and washed three times with PBS. The cells were stained with hematoxylin (Sigma) for 10 minutes and washed with distilled water. Unmigrated cells were removed from the top surface of the membrane with a cotton swab. Membranes were removed from the chamber and fixed with Gel Mount (Biomeda, Foster City, Calif., USA). The migrated cells (cells attached to the lower surface of the membrane) were counted in a randomly selected scope in a high power field (×20).

As a result, the migration of the biliary tract cancer cells treated with 25 μM or more of chlorphenesin was decreased, and in particular, the decrease of cell migration was remarkable at concentrations of 100 μM or more (FIGS. 51 and 52).

3-2-2. Combination Administration

The mobility of the biliary tract cancer cell line SNU1079 was confirmed by the migration assay when cells were treated with chlorphenesin and chloroquine or chloropyrazine in combination. The biliary tract cancer cell line SNU1079 was treated with control (DMSO), chlorphenesin (5 μM), chloroquine (5 μM, 10 μM or 25 μM), chloropyrazine (25 μM or 50 μM), chlorphenesin and chloroquine (5 μM+5 μM, 5 μM+10 μM, 5 μM+25 μM), and chlorphenesin and chloropyrazine (5 μM+25 μM, 5 μM+50 μM). The degree of cell migration was then confirmed in the same manner as in Example 3-2-1. In addition, the synergy effect of combination treatment was calculated using the Combination Index (CI) according to the concentration of the combination treatment of chlorphenesin and chloroquine or chloropyrazine using Compusyn software.

As a result, the inhibition of migration of biliary tract cancer cells synergistically increased (synergy effect) when treated 5 μM of chlorphenesin and 5 μM or 10 μM of chloroquine in combination (FIGS. 53 and 54).

3-3. Invasion Assay

In order to confirm whether single or combination treatment of the chlorphenesin (OC-201), chloroquine (OC-202) and chloropyrazine (OC-203) of the present invention inhibits the characteristics of cancer cells which invade and metastasize into other parts, the biliary tract cancer cell line SNU1079 was treated with control (DMSO), chlorphenesin (5 μM), chloroquine (5 μM, 10 μM or 25 μM), chloropyrazine (25 μM or 50 μM), chlorphenesin and chloroquine (5 μM+5 μM, 5 μM+10 μM, 5 μM+25 μM), and chlorphenesin and chloropyrazine (5 μM+25 μM, 5 μM+50 μM), and the invasion assay was performed by the manner described in Example 2-3. In addition, the synergy effect of combination treatment was calculated using the Combination Index (CI) according to the combination treatment concentration of chlorphenesin and chloroquine or chloropyrazine using Compusyn software.

As a result, it was confirmed that the invasion of biliary tract cancer cells was inhibited as shown in FIG. 55, and in particular, when chlorphenesin and chloroquine were used in combination, the synergy effect was shown (FIG. 56).

Example 4. Confirmation of Cancer Metastasis Inhibitory Effect at Low Concentration In order to determine the concentration of non-cytotoxic chlorphenesin, cell survival rate was assessed by MTT assay (Promega, Ltd.) according to the manufacturer's protocol. CT26 cell line and HCT-116 cell line were inoculated in a 96 well plate at a density of $5 \times 10^3$ cells per well. After pre-treatment or no-treatment with chlorphenesin (100 ppm, 1 μM, 10 μM, 100 μM, 1 mM and 10 mM), the cells were incubated with 5 mg/mL MTT for 4 hours. Then, the medium was removed, and 150 μL of the solubilization solution and the stop solution were added, followed by incubation at 30° C. for 4 hours. The absorbance of the reaction solution was measured at 570 nm. The cell survival rate was calculated by the above equation 1. As shown in FIG. 57, it was confirmed that both CT26 cells and HCT-116 cells were non-cytotoxic in the concentration range of 1 μM to 1 mM.

Even though 1 μM of chlorphenesin is less than the concentration showing muscle relaxation effect, it is not cytotoxic. Thus, in order to evaluate whether chlorphenesin with the low concentration having no anticancer activity has inhibited cancer cell metastasis inhibitory effects, the following experiments were performed.

4-1-1. Confirmation of Inhibition of Cell Migration 4-1-1-1. Migration as Say

Cell migration assay was performed using a 24 well transwell chamber with a polycarbonate membrane (8.0 μm pore size, Costar). The colorectal cancer cells CT26 and HCT116 were suspended in serum-free RPMI and added at $1 \times 10^5$ cells/well in the upper chamber. Laminin (10 μg/ml) was placed in the lower well, and cells were cultured for 8 hours in a $CO_2$ incubator at 37° C. and allowed to migrate. The cells were then fixed with 70% methyl alcohol in PBS for 30 minutes and washed three times with PBS. The cells were stained with hematoxylin (Sigma) for 10 minutes and washed with distilled water. Unmigrated cells were removed from the top surface of the membrane with a cotton swab. Membranes were removed from the chamber and fixed with Gel Mount (Biomeda, Foster City, Calif., USA). The migrated cells (cells attached to the lower surface of the membrane) were counted in a randomly selected scope in a high power field (×20).

As a result, as shown in FIG. 58, it was confirmed that when treated with chlorphenesin at a low concentration (1 μM), the invasion ability and migration ability of the cells was significantly reduced compared to the control.

4-1-1-2. Wound Healing Assay

Wound healing analysis was performed to measure cell motility. First, the colorectal cancer cell line CT26 was added to RPMI supplemented with 10% FBS. After 24 hours, the cells were inoculated on a 24-well tissue culture plate at the concentration in which 70% to 80% confluence was reached by a monolayer. A scratch was carefully and slowly applied to the monolayer with a new 200 μl yellow pipet tip across the center of the well. The resulting gap distance was equal to the outer diameter of the tips. After scratching, the dish was carefully washed twice with medium to remove the separated cells. After incubation of the cells for 24 hours in the presence or absence of chlorphenesin (1 μM), a photograph of the dyed monolayers was taken with a microscope.

As a result, as shown in FIG. 59, it was confirmed that the mobility of the CT26 cell line was reduced by treatment with chlorphenesin (1 µM). This is the result of proving that it affects the inhibition of cancer cell metastasis even at a low concentration which is incapable of killing cancer cells.

4-1-2. Confirmation of In Vivo Inhibition of Cancer Metastasis

The inhibitory effect of chlorphenesin on tumor proliferation was confirmed by animal experiments. Specifically, 60 Balb/c mice were subcutaneously inoculated once with 100 µL of CT26 cell suspension ($1\times10^7$ cells/mL) to induce tumors, thereby producing a xenograft animal model. For 5 weeks from 3 days after the inoculation of the cancer cells, chlorphenesin was administered alone or in combination with fluorouracil (5' FU), which is an anticancer drug. First, for the combination administration with fluorouracil, 11 animal models were abdominally administered with 25 mg/kg fluorouracil (5 times a week) and 10 mg/kg chlorphenesin (3 times a week) in combination for 5 weeks. For the chlorphenesin single administration, 10 animal models were abdominally administered with 10 mg/kg chlorphenesin (3 times a week) for 5 weeks or 14 animal models were orally administered with 20 mg/kg chlorphenesin (5 times a week) for 5 weeks. 14 animal models were administered with the same dose of PBS as chlorphenesin as a negative control. 14 animal models were administered with 25 mg/kg fluorouracil, anticancer agent, alone (5 times a week) as a positive control. The body weight of the animal models was measured once a week, and the tumor size was measured once a week from the day of drug administration. After 6 weeks, animal models were anesthetized with ether, and tumors and lungs were collected.

As a result, as shown in FIG. 60, it was confirmed that the chlorphenesin-treated group showed no cancer metastasis to lungs compared to control groups. In addition, as shown in FIG. 61, it was confirmed that the chlorphenesin-treated group showed a reduction in the tumor size in the animals treated with chlorphenesin at 20 mg/kg compared with the control groups. These suggest that chlorphenesin is a negative regulator of both tumor growth and metastatic potential.

In this specification, exemplary embodiments of the present invention have been classified into the first, second and third exemplary embodiments and described for conciseness. However, the respective steps or functions of an exemplary embodiment may be combined with those of another exemplary embodiment to implement still another exemplary embodiment of the present invention.

The invention claimed is:

1. A method for inhibiting cancer proliferation and metastasis, comprising administering a composition comprising (i) chlorphenesin and chloroquine, or (ii) chlorphenesin and chloropyrazine, or a pharmaceutically acceptable salt of any of them as an active ingredient to a subject in need thereof, wherein the cancer is colorectal cancer, pancreatic cancer or biliary tract cancer, and wherein the method does not comprise administering 5-fluorouracil.

2. A method for treating cancer, comprising administering a composition comprising (i) chlorphenesin and chloroquine, or (ii) chlorphenesin and chloropyrazine, or a pharmaceutically acceptable salt of any of them in a pharmaceutical effective amount to a subject in need thereof, wherein the cancer is colorectal cancer, pancreatic cancer or biliary tract cancer, and wherein the method does not comprise administering 5-fluorouracil.

3. A method for treating cancer, comprising administering a composition comprising (i) chlorphenesin carbamate and chloroquine or a pharmaceutically acceptable salt thereof, or (ii) chlorphenesin carbamate and chloropyrazine or a pharmaceutically acceptable salt thereof, in a pharmaceutical effective amount to a subject in need thereof, wherein the cancer is colorectal cancer, pancreatic cancer or biliary tract cancer, and wherein the method does not comprise administering 5-fluorouracil.

4. A method for treating cancer, comprising
administering a composition comprising chlorphenesin and chloroquine, or a pharmaceutically acceptable salt thereof in a pharmaceutical effective amount to a subject in need thereof,
wherein the cancer is colorectal cancer, pancreatic cancer or biliary tract cancer.

5. A method for treating cancer, comprising administering a composition comprising at least one selected from the group consisting of chlorphenesin carbamate, chloroquine and chloropyrazine, or a pharmaceutically acceptable salt thereof in a pharmaceutical effective amount to a subject in need thereof, wherein the cancer is colorectal cancer, pancreatic cancer or biliary tract cancer.

* * * * *